United States Patent
Chalothorn et al.

(10) Patent No.: US 12,304,969 B2
(45) Date of Patent: May 20, 2025

(54) FACTOR XI A2 DOMAIN-BINDING ANTIBODIES AND METHODS OF USE THEREOF

(71) Applicant: Regeneron Pharmaceuticals, Inc., Tarrytown, NY (US)

(72) Inventors: Dan Chalothorn, New York, NY (US); Lori C. Morton, Chappaqua, NY (US); KehDih Lai, Yardley, PA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 15 days.

(21) Appl. No.: 18/048,644

(22) Filed: Oct. 21, 2022

(65) Prior Publication Data

US 2023/0131338 A1    Apr. 27, 2023

Related U.S. Application Data

(60) Provisional application No. 63/270,629, filed on Oct. 22, 2021.

(51) Int. Cl.
  *C07K 16/36* (2006.01)
  *A61P 7/02* (2006.01)
  *A61K 39/00* (2006.01)

(52) U.S. Cl.
  CPC ............... *C07K 16/36* (2013.01); *A61P 7/02* (2018.01); *A61K 2039/505* (2013.01); *A61K 2039/545* (2013.01); *C07K 2317/21* (2013.01); *C07K 2317/565* (2013.01); *C07K 2317/76* (2013.01); *C07K 2317/92* (2013.01)

(58) Field of Classification Search
  CPC ............... C07K 16/36; C07K 2317/21; C07K 2317/565; C07K 2317/76; C07K 2317/92; A61P 7/02; A61K 2039/505; A61K 2039/545
  USPC ....................................... 424/139.1
  See application file for complete search history.

(56) References Cited

FOREIGN PATENT DOCUMENTS

WO    2017/127468 A1    7/2017
WO    2020/154234 A1    7/2020

OTHER PUBLICATIONS

Orentz et al., Contact Activation Inhibitor and Factor XI Antibody, AB023, Produces Safe, Dose-Dependent Anticoagulation in a Phase 1 First-In-Human Trial. Arterioscler Thromb Vasc Biol. Apr. 2019, 39(4):799-809.
Rudikoff et al., Single amino acid substitution altering antigen-binding specificity. Proc Natl Acad Sci U S A. Mar. 1982;79(6):1979-83.
Invitation to Pay Additional Fees for Application No. PCT/US2022/078530, dated Mar. 14, 2023, 23 pages.

*Primary Examiner* — Yan Xiao
(74) *Attorney, Agent, or Firm* — McCarter & English, LLP; Marcie B. Clarke, Esq.

(57) ABSTRACT

The present disclosure provides antibodies that bind to the A2 domain of Factor XI (FXI) and methods of using the same. According to certain embodiments, the antibodies are antagonist antibodies that inhibit blood clot formation via the intrinsic pathway without affecting hemostasis, as shown by their effect on prolonging aPTT without affecting PT. As such, these antagonist antibodies may be used to treat blood clotting diseases or disorders or treatment regimens that have clot formation as a risk factor, such as, but not limited to atrial fibrillation. In certain embodiments, the disclosure includes antibodies that bind FXI and mediate clot formation or thrombogenesis. The antibodies of the disclosure may be fully human, non-naturally occurring antibodies.

20 Claims, 12 Drawing Sheets

Specification includes a Sequence Listing.

REGN9933
TGA Induced by EA in Human Plasma

IgG4$^P$ Isotype Control
TGA Induced by EA in Human Plasma

REGN9933
TGA Induced by TF in Human Plasma

IgG4$^P$ Isotype Control
TGA Induced by TF in Human Plasma

FACTOR XI A2 DOMAIN-BINDING ANTIBODIES AND METHODS OF USE THEREOF

RELATED APPLICATIONS

The instant application claims the benefit of priority to U.S. Provisional Application No. 63/270,629, filed on Oct. 22, 2021, the contents of which are expressly incorporated herein by reference in their entirety.

SEQUENCE LISTING

The instant application contains a Sequence Listing which has been submitted electronically in XML format and is hereby incorporated by reference in its entirety. Said XML copy, created on Oct. 21, 2022 is named 118003-01002.XML and is 45,441 bytes in size.

FIELD

The present disclosure relates to antibodies that bind to the apple 2 (A2) domain of Factor XI (FXI), compositions comprising these antibodies, and methods of use thereof.

BACKGROUND

The formation of blood clots (i.e., thrombi) is initiated either through (a) the contact pathway or through (b) the extrinsic pathway. Both pathways converge through (c) the common pathway to activate thrombin, which acts as a serine protease to convert soluble fibrinogen into insoluble strands of fibrin. Cross-linked fibrin protein is a major component of blood clots, along with aggregated platelets and red blood cells.

The extrinsic pathway moderates hemostasis at vascular injury. Here, exposed tissue factor (TF) activates factor VII (FVII) to form the FVIIa-TF complex, which activates factor X (FX) in the common pathway to generate prothrombinase, which generates thrombin and subsequent clot formation.

The contact pathway is distinct from the extrinsic pathway in that it is less involved in hemostasis but nonetheless effects clot formation. Here, coagulation is initiated by intrinsic events, such as the release of polyphosphate from platelets, or the extrusion of histone and DNA-laden neutrophil extracellular traps (NETs) from neutrophils, which activate factor XII (FXII). Activated FXII (i.e., FXIIa) further activates factor XI (FXI) to form FXIa, which leads to the generation of thrombin via the common pathway. Thrombin and platelet-produced polyphosphate also activate FXI in a feed-forward manner to amplify clot formation.

FXI is a zymogen of the plasma protease FXIa, which sustains thrombin generation via FIX activation. FXI is a 160 kDa disulfide-linked homodimer, in which each subunit consists of, from N-terminus to C-terminus, apple domains A1-A4 and a catalytic domain (CD). The disulfide bond is between the A4 domains of each subunit. FXI subunits are activated by cleavage of one or both of the Arg-Ile bonds located between the A4 and CD domains to form FXIa. It is generally believed that cleavage of the Arg-Ile bond is catalyzed by FXIIa and/or thrombin.

BRIEF SUMMARY

Provided herein are isolated monoclonal antibodies and antigen-binding fragments thereof that bind, e.g., specifically bind, to the A2 domain of Factor XI (FXI). In any of the embodiments disclosed herein, the antibody, or antigen-binding fragment thereof, may specifically bind the A2 domain of FXI. The isolated antibodies and antigen-binding fragments of the disclosure are useful for treating diseases and disorders associated with FXI activity or expression.

In its broadest aspect, the disclosure provides anti-FXI antibodies, which block FXI activity or activation and reduce blood clot formation. These antibodies may be used to prevent, treat, reduce the incidence of, or reduce the negative effects of blood clot formation in the blood stream or tissue in a patient in need thereof. Preferably, anti-FXI antibodies attenuate thrombosis without perturbing hemostasis.

In certain embodiments, the anti-FXI antibodies may be useful to treat various blood clotting disorders or diseases where the treatment the disease involves the use of anticoagulant therapy and where there is a risk to the patient of bleeding due to the use of anticoagulant therapy. Those indications, disorders or diseases include high risk atrial fibrillation, primary venous thromboembolism (VTE) prophylaxis, extended VTE treatment, prevention of recurrent ischemia after acute coronary syndrome, end-stage renal disease, medical devices (e.g., mechanical heart valves, ventricular assist devices, small caliber grafts, central venous catheters, and the like), extracorporeal circuits, and the like.

The antibodies of the disclosure can be full-length (for example, an IgG1 or IgG4 antibody) or may comprise only an antigen-binding portion (for example, a Fab, F(ab')2 or scFv fragment), and may be modified to affect functionality, e.g., to eliminate residual effector functions (Reddy et al., 2000, J. Immunol. 164:1925-1933).

An exemplary anti-FXI antibody of the present disclosure is listed in Table 1 herein. Table 1 sets forth the amino acid sequence identifiers and the nucleic acid sequence identifiers of exemplary heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-FXI antibody. Table 1 also sets forth the nucleic acid sequence identifiers of exemplary HCVRs, LCVRs, HCDR1, HCDR2 HCDR3, LCDR1, LCDR2 and LCDR3 of an exemplary anti-FXI antibody.

The present disclosure provides antibodies or antigen-binding fragments thereof that bind FXI, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present disclosure also provides antibodies or antigen-binding fragments thereof that bind FXI, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present disclosure also provides antibodies or antigen-binding fragments thereof that bind FXI, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/

LCVR amino acid sequence pair contained within any of the exemplary anti-FXI antibodies listed in Table 1.

Accordingly, in a first aspect, the disclosure provides an isolated antibody, or antigen-binding fragment thereof, that binds to serum clotting factor XI (FXI), wherein the antibody, or antigen-binding fragment thereof, comprises three heavy chain complementarity determining regions (CDRs) (HCDR1, HCDR2 and HCDR3) contained within a heavy chain variable region (HCVR) comprising an amino acid sequence as set forth in Table 1, or a substantially similar sequence thereof having at least 90% sequence identity thereto; and three light chain CDRs (LCDR1, LCDR2 and LCDR3) contained within a light chain variable region (LCVR) comprising an amino acid sequence as set forth in Table 1, or a substantially similar sequence thereof having at least 90% sequence identity thereto.

In one embodiment, the anti-FXI antibody, or antigen-binding fragment thereof, exhibits one or more properties selected from the group consisting of:
(a) is an antagonist antibody;
(b) binds human FXI with a $K_D$ of less than about 35 pM as measured by surface plasmon resonance at 25° C. or at 37° C.;
(c) binds human FXIa with a $K_D$ of less than about 765 pM as measured by surface plasmon resonance at 25° C. or at 37° C.;
(d) binds human FXI with a dissociative half-life (t½) of greater than about 1,000 minutes as measured by surface plasmon resonance at 25° C. or at 37° C.;
(e) binds human FXIa with a dissociative half-life (t½) of greater than about 23 minutes as measured by surface plasmon resonance at 25° C. or at 37° C.;
(f) inhibits activation of Factor Xa (FXa) by FXI in normal dilute plasma by at least about 85% at an IC50 of less than about 39 pM;
(g) inhibits activation of Factor Xa (FXa) by FXIa in normal dilute plasma by at least about 25% at an IC50 of less than about 10 nM;
(h) preferentially binds to the PKA2 domain (i.e., apple domain 2 or A2) relative to full length FXI, PKA1, PKA3, and PKA4 as determined by label-free biolayer interferometry;
(i) competes for binding to FXI with an antibody that specifically binds to epitopes of within and overlapping with the FXI PKA2 domain;
(j) increases by at least two-fold activated partial thromboplastin time (aPTT), which is a measure of intrinsic clotting time, in a primate in vivo without measurably affecting prothrombin time (PT), which is a measure of extrinsic clotting time;
(k) inhibits by 5%-15% intrinsic pathway peak thrombin activity in a primate in vivo;
(l) prolongs aPTT about two-fold in human plasma in vitro at a concentration of about ≤33 nM without doubling PT; and/or
m) inhibits intrinsic pathway thrombin production in human plasma in vitro at a concentration of about ≥31 nM with no effect on extrinsic pathway thrombin production with a dose up to about 500 nM.

In one embodiment, the disclosure provides an antibody, or antigen-binding fragment thereof, that binds Factor XI (FXI), wherein the antibody, or antigen-binding fragment thereof, comprises: (a) the complementarity determining regions (CDRs) of a heavy chain variable region (HCVR) comprising an amino acid sequence as set forth in Table 1; and (b) the CDRs of a light chain variable region (LCVR) comprising an amino acid sequence as set forth in Table 1.

In one embodiment, the antibody, or antigen-binding fragment thereof, that binds FXI comprises three heavy chain CDRs (HCDR1, HCDR2 and HCDR3) contained within a HCVR sequence of SEQ ID NO: 3 or SEQ ID NO: 31, or a substantially similar sequence thereof having at least 90% sequence identity thereto; and three light chain CDRs (LCDR1, LCDR2 and LCDR3) contained within a LCVR sequence of SEQ ID NO: 13, or a substantially similar sequence thereof having at least 90% sequence identity thereto.

In one embodiment, the isolated antibody, or antigen-binding fragment thereof, that binds FXI comprises a HCVR having an amino acid sequence of SEQ ID NO: 3 or SEQ ID NO:31.

In one embodiment, the isolated antibody, or antigen-binding fragment thereof, that binds FXI further comprises a LCVR having an amino acid sequence of SEQ ID NO: 13.

In one embodiment, the isolated antibody, or antigen-binding fragment thereof, that binds FXI comprises a HCVR having an amino acid sequence of SEQ ID NO: 3 or SEQ ID NO:31; and a LCVR having an amino acid sequence of SEQ ID NO: 13.

In one embodiment, the isolated antibody, or antigen-binding fragment thereof, that binds FXI comprises the CDRs of a HCVR/LCVR amino acid sequence pair of SEQ ID NOs: 3/13 or SEQ ID NOs: 31/13.

The present disclosure also provides antibodies or antigen-binding fragments thereof that bind FXI, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity thereto.

The present disclosure also provides antibodies or antigen-binding fragments thereof that bind FXI, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-FXI antibodies listed in Table 1. In certain embodiments, the HCDR3/LCDR3 amino acid sequence pair is SEQ ID Nos: 9/19 or SEQ ID NOs: 37/19.

The present disclosure also provides antibodies or antigen-binding fragments thereof that bind FXI, comprising a set of six CDRs (i.e., HCDR1, HCDR2, HCDR3, LCDR1, LCDR2, LCDR3) contained within any of the exemplary anti-FXI antibodies listed in Table 1. In certain embodiments, the HCDR1, HCDR2, HCDR3, LCDR1, LCDR2, LCDR3 amino acid sequence set is SEQ ID NOs: 5, 7, 9, 15, 17, and 19 or SEQ ID NOs: 33, 35, 37, 15, 17 and 19.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In one embodiment, the disclosure provides an isolated antibody, or antigen-binding fragment thereof, that binds FXI comprising:
(a) a HCDR1 domain having an amino acid sequence of SEQ ID NO: 5;
(b) a HCDR2 domain having an amino acid sequence of SEQ ID NO: 7;
(c) a HCDR3 domain having an amino acid sequence of SEQ ID NO: 9;
(d) a LCDR1 domain having an amino acid sequence of SEQ ID NO: 15;
(e) a LCDR2 domain having an amino acid sequence of SEQ ID NO: 17; and
(f) a LCDR3 domain having an amino acid sequence of SEQ ID NO: 19.

In one embodiment, the isolated antibody, or antigen-binding fragment thereof, comprises a set of six CDRs (HCDR1-HCDR2-HCDR3-LCDR1-LCDR2-LCDR3) of SEQ ID NOs: 5-7-9-15-17-19.

In one embodiment, the disclosure provides an isolated antibody, or antigen-binding fragment thereof, that binds FXI comprising:
(a) a HCDR1 domain having an amino acid sequence of SEQ ID NO: 33;
(b) a HCDR2 domain having an amino acid sequence of SEQ ID NO: 35;
(c) a HCDR3 domain having an amino acid sequence of SEQ ID NO: 37;
(d) a LCDR1 domain having an amino acid sequence of SEQ ID NO: 15;
(e) a LCDR2 domain having an amino acid sequence of SEQ ID NO: 17; and
(f) a LCDR3 domain having an amino acid sequence of SEQ ID NO: 19.

In one embodiment, the isolated antibody, or antigen-binding fragment thereof, comprises a set of six CDRs (HCDR1-HCDR2-HCDR3-LCDR1-LCDR2-LCDR3) of SEQ ID NOs: 33-35-37-15-17-19.

In one embodiment, the isolated antibody, or antigen-binding fragment thereof, that binds to FXI comprises an antibody, or antigen-binding fragment thereof, that competes for binding to FXI with a reference antibody, wherein the reference antibody preferentially binds to the Apple 2 (A2 or PKA2) of FXI.

In one embodiment, the isolated antibody, or antigen-binding fragment thereof, that binds to FXI comprises an antibody, or antigen-binding fragment thereof, that binds to the same epitope as a reference antibody, wherein the reference antibody preferentially binds to the Apple 2 (A2 or PKA2) of FXI.

In one embodiment, the isolated antibody, or antigen-binding fragment thereof, binds human FXI with a $K_D$ of less than about 1,000 pM as measured by surface plasmon resonance at 25° C. or 37° C.

In one embodiment, the isolated antibody, or antigen-binding fragment thereof, binds human FXI with a $K_D$ of less than about 500 pM as measured by surface plasmon resonance at 25° C. or 37° C.

In one embodiment, the isolated antibody, or antigen-binding fragment thereof, binds human FXI with a $K_D$ of less than about 250 pM as measured by surface plasmon resonance at 25° C. or 37° C.

In one embodiment, the isolated antibody, or antigen-binding fragment thereof, binds human FXI with a $K_D$ of less than about 100 pM as measured by surface plasmon resonance at 25° C. or 37° C.

In one embodiment, the isolated antibody, or antigen-binding fragment thereof, binds human FXI with a $K_D$ of less than about 50 pM as measured by surface plasmon resonance at 25° C. or 37° C.

In one embodiment, the isolated antibody, or antigen-binding fragment thereof, binds human FXI with a $K_D$ of less than about 25 pM as measured by surface plasmon resonance at 25° C. or 37° C.

In one embodiment, the isolated antibody, or antigen-binding fragment thereof, binds human FXI with a dissociative half-life (t½) of greater than about 10 minutes as measured by surface plasmon resonance at 25° C. or 37° C.

In one embodiment, the isolated antibody, or antigen-binding fragment thereof, binds human FXI with a t½ of greater than about 20 minutes as measured by surface plasmon resonance at 25° C. or 37° C.

In one embodiment, the isolated antibody, or antigen-binding fragment thereof, binds human FXI with a t½ of greater than about 60 minutes as measured by surface plasmon resonance at 25° C. or 37° C.

In one embodiment, the isolated antibody, or antigen-binding fragment thereof, binds human FXI with a t½ of greater than about 2 hours as measured by surface plasmon resonance at 25° C. or 37° C.

In one embodiment, the isolated antibody, or antigen-binding fragment thereof, binds human FXI with a t½ of greater than about 5 hours as measured by surface plasmon resonance at 25° C. or 37° C.

In one embodiment, the isolated antibody, or antigen-binding fragment thereof, binds human FXI with a t½ of greater than about 10 hours as measured by surface plasmon resonance at 25° C. or 37° C.

In one embodiment, the isolated antibody, or antigen-binding fragment thereof, binds human FXI with a t½ of greater than about 15 hours as measured by surface plasmon resonance at 25° C. or 37° C.

In one embodiment, the isolated antibody, or antigen-binding fragment thereof, binds human FXI with a t½ of greater than about 16 hours as measured by surface plasmon resonance at 25° C. or 37° C.

In one embodiment, the isolated antibody, or antigen-binding fragment thereof, binds human FXI with a t½ of greater than about 1,000 minutes as measured by surface plasmon resonance at 25° C. or 37° C.

In one embodiment, the isolated antibody, or antigen-binding fragment thereof, binds human FXIa with a $K_D$ of less than about 100 nM as measured by surface plasmon resonance at 25° C. or 37° C.

In one embodiment, the isolated antibody, or antigen-binding fragment thereof, binds human FXIa with a $K_D$ of less than about 10 nM as measured by surface plasmon resonance at 25° C. or 37° C.

In one embodiment, the isolated antibody, or antigen-binding fragment thereof, binds human FXIa with a $K_D$ of less than about 1,000 pM as measured by surface plasmon resonance at 25° C. or 37° C.

In one embodiment, the isolated antibody, or antigen-binding fragment thereof, binds human FXIa with a $K_D$ of less than about 500 pM as measured by surface plasmon resonance at 25° C. or 37° C.

In one embodiment, the isolated antibody, or antigen-binding fragment thereof, binds human FXIa with a dissociative half-life (t½) of greater than about 5 minutes as measured by surface plasmon resonance at 25° C. or 37° C.

In one embodiment, the isolated antibody, or antigen-binding fragment thereof, binds human FXIa with a t½ of greater than about 10 minutes as measured by surface plasmon resonance at 25° C. or 37° C.

In one embodiment, the isolated antibody, or antigen-binding fragment thereof, binds human FXI with a t½ of greater than about 15 minutes as measured by surface plasmon resonance at 25° C. or 37° C.

In one embodiment, the isolated antibody, or antigen-binding fragment thereof, binds human FXIa with a t½ of greater than about 20 minutes as measured by surface plasmon resonance at 25° C. or 37° C.

In one embodiment, the isolated antibody, or antigen-binding fragment thereof, binds human FXIa with a t½ of greater than about 25 minutes as measured by surface plasmon resonance at 25° C. or 37° C.

In one embodiment, the isolated antibody, or antigen-binding fragment thereof, that binds to FXI inhibits activation of Factor Xa (FXa) by FXI in normal dilute serum by at least about 85% at an IC50 of less than about 39 pM.

In one embodiment, the isolated antibody, or antigen-binding fragment thereof, that binds to FXI inhibits activation of Factor Xa (FXa) by FXIa in normal dilute serum by at least about 25% at an IC50 of less than about 10 nM.

In one embodiment, the isolated antibody, or antigen-binding fragment thereof, that binds to FXI preferentially binds to the PKA2 domain (i.e., apple domain 2 or A2) relative to full length FXI, PKA1, PKA3, and PKA4 as determined by label-free biolayer interferometry.

In one embodiment, the isolated antibody, or antigen-binding fragment thereof, that binds to FXI competes for binding to FXI with an antibody that specifically binds to epitopes of within and overlapping with the FXI PKA2.

In one embodiment, the isolated antibody, or antigen-binding fragment thereof, that binds to FXI increases by at least two-fold activated partial thromboplastin time (aPTT), which is a measure of intrinsic clotting time, in a primate in vivo without measurably affecting prothrombin time (PT), which is a measure of extrinsic clotting time.

In one embodiment, the isolated antibody, or antigen-binding fragment thereof, that binds to FXI inhibits intrinsic pathway peak thrombin activity in a primate in vivo by about 5%-15%, about 1%-20%, about 0.5%-25%, about 3%-5%, about 4%-6%, about 5%-7%, about 6%-8%, about 7%-9%, about 8%-10%, about 9%-11%, about 10%-12%, about 11%-13%, about 12%-14%, about 13%-15%, about 14%-16%, about 15%-17%, about 16%-18%, about 17%-19%, or about 18%-20%.

In one embodiment, the isolated antibody, or antigen-binding fragment thereof, that binds to FXI prolongs aPTT about two-fold in human plasma in vitro at a concentration of about 100 pM-100 nM, about 1 nM-50 nM, about 5 nM-40 nM, about 10 nM-35 nM, ≤60 nM, ≤55 nM, ≤50 nM, ≤45 nM, ≤40 nM, ≤39 nM, ≤38 nM, ≤37 nM, ≤36 nM, ≤35 nM, ≤34 nM, ≤33 nM, ≤32 nM, ≤31 nM, ≤30 nM, ≤25 nM, or ≤20 nM. Here, the anti-FXI prolongs aPTT about two-fold without doubling the PT.

In one embodiment, the isolated antibody, or antigen-binding fragment thereof, that binds to FXI inhibits intrinsic pathway thrombin production in human plasma in vitro at a concentration of about 10 nM-100 nM, about 15 nM-500 nM, about 20 nM-60 nM, about 25 nM-50 nM, ≥25 nM, ≥26 nM, ≥27 nM, ≥28 nM, ≥29 nM, ≥30 nM, ≥31 nM, ≥32 nM, ≥33 nM, ≥34 nM, ≥35 nM, ≥36 nM, ≥37 nM, ≥38 nM, ≥39 nM, or ≥40 nM. Here, the anti-FXI inhibits the intrinsic pathway thrombin production with no effect on extrinsic pathway thrombin production with a dose up to about 500 nM.

In a second aspect, the present disclosure provides nucleic acid molecules encoding anti-FXI antibodies or portions thereof. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto.

The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 1, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 1, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 1, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 1, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 1, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 1, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 1, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-FXI antibodies listed in Table 1.

The present disclosure also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-FXI antibodies listed in Table 1.

The present disclosure also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-FXI antibody listed in Table 1.

In a third aspect, the present disclosure provides recombinant expression vectors capable of expressing a polypeptide comprising a heavy or light chain variable region of an anti-FXI antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes anti-FXI antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the disclosure provides a pharmaceutical composition comprising at least one antibody of the disclosure, or an antigen binding fragment thereof, which specifically binds FXI and a pharmaceutically acceptable carrier.

In a related aspect, the disclosure features a composition, which is a combination of an anti-FXI antibody and a second therapeutic agent. In one embodiment, the second therapeutic agent is any agent that is advantageously combined with an anti-FXI antibody. The second therapeutic agent may be useful for alleviating at least one symptom of a disease or disorder.

In a fifth aspect, the disclosure provides a method for enhancing a biological activity mediated by FXI, the method comprising contacting FXI with a biologically effective amount of an antagonist anti-FXI antibody of Table 1, or contacting FXI with a pharmaceutical composition containing a biologically effective amount of an antagonist anti-FXI antibody of Table 1.

In certain embodiments, the biological activity is blood clotting or blood clotting as a result of the intrinsic clotting pathway and not blood clotting as a result of the extrinsic (i.e., e.g., tissue factor induced) pathway; and blood clotting or blood clotting as a result of the intrinsic clotting pathway and not blood clotting as a result of the extrinsic pathway is inhibited or otherwise reduced upon contact of FXI or FXIa with an antagonist anti-FXI antibody.

In a sixth aspect, the disclosure provides therapeutic methods for treating a disease or disorder associated with FXI activity or expression, or at least one symptom associated with the disease or disorder, using an anti-FXI antibody or antigen-binding portion of an antibody of the disclosure. The therapeutic methods according to this aspect of the disclosure comprise administering a therapeutically effective amount of a pharmaceutical composition comprising an antibody or antigen-binding fragment of an antibody of the disclosure to a subject in need thereof. The disorder treated is any disease or condition which is improved, ameliorated, inhibited or prevented by targeting FXI and/or by inactivating FXI-mediated blood clotting.

In one embodiment, the anti-FXI antibodies of the disclosure may provide a method of treating pathological intrinsic clotting, without adversely affecting hemostasis. In one embodiment, the anti-FXI antibodies of the disclosure may provide a method of treating diseases, disorders, clotting side effects, indirect clotting effects of any one of Factor V Leiden, prothrombin gene mutation, deficiencies of natural proteins that prevent clotting (such as antithrombin, protein C and protein S), elevated levels of homocysteine, elevated levels of fibrinogen or dysfunctional fibrinogen (dysfibrinogenemia), elevated levels of factor VIII, factor IX, and/or XI, abnormal fibrinolytic system, including hypoplasminogenemia, dysplasminogenemia and elevation in levels of plasminogen activator inhibitor (PAI-1), atrial fibrillation, cancer, side effects of some medications used to treat cancer, such as tamoxifen, bevacizumab, thalidomide and lenalidomide, recent trauma or surgery, central venous catheter placement, obesity, pregnancy, supplemental estrogen use, including oral contraceptive pills (birth control pills), hormone replacement therapy, prolonged bed rest or immobility, heart attack, congestive heart failure, stroke and other illnesses that lead to decreased activity, heparin-induced thrombocytopenia (decreased platelets in the blood due to heparin or low molecular weight heparin preparations), lengthy airplane travel, antiphospholipid antibody syndrome, deep vein thrombosis or pulmonary embolism, myeloproliferative disorders such as polycythemia vera or essential thrombocytosis, paroxysmal nocturnal hemoglobinuria, inflammatory bowel syndrome, HIV/AIDS, nephrotic syndrome, COVID-19 infection or spike protein immunization effects, and the like.

A seventh aspect of the disclosure provides for a method of preventing thrombosis in a subject without adversely affecting hemostasis, the method comprising administering a therapeutically effective amount of a FXI antagonist antibody of Table 1, or a pharmaceutical composition comprising a therapeutically effective amount of the antibody or antigen-binding fragment thereof, to the subject.

In one embodiment, the methods described above may be achieved by administering an antagonist anti-FXI antibody, or antigen-binding fragment thereof, to a subject in need thereof, wherein the antagonist anti-FXI antibody comprises three heavy chain complementarity determining regions (CDRs) (HCDR1, HCDR2 and HCDR3) contained within a heavy chain variable region (HCVR) comprising an amino acid sequence as set forth in Table 1, or a substantially similar sequence thereof having at least 90% sequence identity thereto; and three light chain CDRs (LCDR1, LCDR2 and LCDR3) contained within a light chain variable region (LCVR) comprising an amino acid sequence as set forth in Table 1, or a substantially similar sequence thereof having at least 90% sequence identity thereto.

In one embodiment, the methods of the disclosure may be achieved by administering an antagonist FXI antibody of the disclosure, wherein the antibody, or antigen-binding fragment thereof, comprises three heavy chain CDRs (HCDR1, HCDR2 and HCDR3) contained within the HCVR sequence of SEQ ID NO: 3 or SEQ ID NO: 31, or a substantially similar sequence thereof having at least 90% sequence identity thereto; and three light chain CDRs (LCDR1, LCDR2 and LCDR3) contained within the LCVR sequence of SEQ ID NO: 13, or a substantially similar sequence thereof having at least 90% sequence identity thereto.

In one embodiment, the antibody, or antigen-binding fragment thereof, comprises a HCVR having an amino acid sequence of SEQ ID NO: 3 or SEQ ID NO: 31.

In one embodiment, the antibody, or antigen-binding fragment thereof, comprises a LCVR having an amino acid sequence of SEQ ID NO: 13.

In one embodiment, the antibody, or antigen-binding fragment thereof, comprises a HCVR having an amino acid sequence of SEQ ID NO: 3; and a LCVR having an amino acid sequence of SEQ ID NO: 13. In one embodiment, the antibody, or antigen-binding fragment thereof, comprises a HCVR having an amino acid sequence of SEQ ID NO: 31; and a LCVR having an amino acid sequence of SEQ ID NO: 13.

In one embodiment, the antibody, or antigen-binding fragment thereof, comprises the CDRs of a HCVR/LCVR amino acid sequence pair of SEQ ID NOs: 3/13, or SEQ ID NOs: 31/13.

In one embodiment, the antibody, or antigen-binding fragment thereof, comprises a HCVR/LCVR amino acid sequence pair of SEQ ID NOs: 3/13, or SEQ ID NOs: 31/13.

In one embodiment, the antibody, or antigen-binding fragment thereof, comprises:
 (a) a HCDR1 domain having an amino acid sequence of SEQ ID NO: 5;
 (b) a HCDR2 domain having an amino acid sequence of SEQ ID NO: 7;
 (c) a HCDR3 domain having an amino acid sequence of SEQ ID NO: 9;
 (d) a LCDR1 domain having an amino acid sequence of SEQ ID NO: 15;
 (e) a LCDR2 domain having an amino acid sequence of SEQ ID NO: 17; and
 (f) a LCDR3 domain having an amino acid sequence of SEQ ID NO: 19.

In one embodiment, the antibody, or antigen-binding fragment thereof, comprises a set of six CDRs (HCDR1-HCDR2-HCDR3-LCDR1-LCDR2-LCDR3) having amino acid sequences of SEQ ID NOs: 5-7-9-15-17-19.

In one embodiment, the antibody, or antigen-binding fragment thereof, comprises:
 (a) a HCDR1 domain having an amino acid sequence of SEQ ID NO: 33;
 (b) a HCDR2 domain having an amino acid sequence of SEQ ID NO: 35;
 (c) a HCDR3 domain having an amino acid sequence of SEQ ID NO: 37;
 (d) a LCDR1 domain having an amino acid sequence of SEQ ID NO: 15;
 (e) a LCDR2 domain having an amino acid sequence of SEQ ID NO: 17; and
 (f) a LCDR3 domain having an amino acid sequence of SEQ ID NO: 19.

In one embodiment, the antibody, or antigen-binding fragment thereof, comprises a set of six CDRs (HCDR1-HCDR2-HCDR3-LCDR1-LCDR2-LCDR3) having amino acid sequences of SEQ ID NOs: 33-35-37-15-17-19.

In one embodiment, the antibody, or antigen-binding fragment thereof, specifically binds human FXI.

In one embodiment, the disease or disorder to be treated with an anti-FXI antibody of the disclosure is thrombosis, and any complication resulting from thrombosis.

It is envisioned that any disease or disorder associated with FXI activity or expression is amenable to treatment with an antibody of the disclosure. These disorders may include any disease or condition in which harmful clot formation is a risk, especially, but not limited to, those conditions in which intrinsic clotting and hemostasis are a risk to the patient.

Other embodiments will become apparent from a review of the ensuing detailed description.

BRIEF DESCRIPTION OF THE FIGURES

FIG. 8B shows overlapping lines for REGN9933 and the IgG4P isotype control for the PT clotting assay; therefore, these lines cannot be distinguished. Changes in aPTT and PT compared to baseline (i.e., no-antibody control) were determined; the average change of duplicate samples is plotted for each antibody concentration tested.

FIG. 10A depicts a line graph showing total REGN9933 in serum measured in an enzyme-linked immunosorbent assay (ELISA) using a mouse anti-human IgG Fc monoclonal antibody (mAb). FIG. 10 Pharm sum at 2.1.1 depicts a line graph showing total FXI in plasma measured using an ELISA using a goat anti-human FXI mAb; fold changes in total FXI (compared to baseline) are reported. Data are expressed as the group mean±standard error of the mean (SEM).

FIG. 11A depicts a line graph showing EA mediated aPTT as a function of fold change of aPTT (compared to baseline) over time. FIG. 11B depicts a line graph showing TF mediated PT as a function of fold change of PT (compared to baseline) over time. Data are expressed as the group mean±standard error of the mean (SEM).

FIG. 12A depicts a line graph showing EA mediated aPTT as a function of fold change of Endogenous Thrombin Potential (ETP) (compared to baseline) over time. FIG. 12B depicts a line graph showing TF mediated PT as a function of fold change of ETP (compared to baseline) over time. Data are expressed as the group mean±standard error of the mean (SEM).

DETAILED DESCRIPTION

Figure 1:
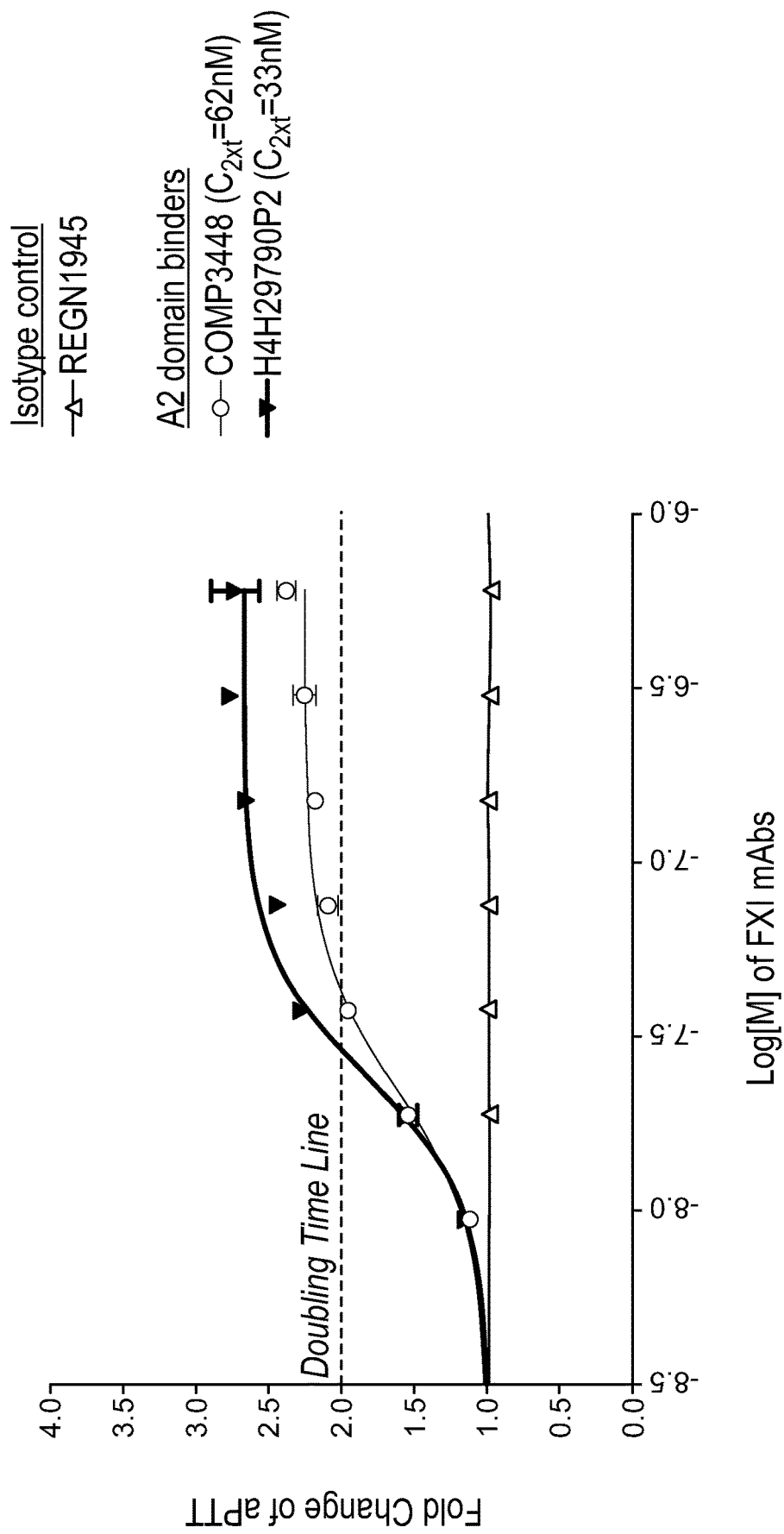
FIG. 1 depicts a line graph showing fold change in aPTT as a function of log concentration of antibody. Filled pyramids depict either an isotype control antibody (apex at top) or an FXI A2 antibody of the invention, REGN9933 (apex at bottom, labeled as H4H29790P2). Filled circles depict a comparator antibody that binds FXI A2.

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, the preferred methods and materials are now described. All patents, applications and non-patent publications mentioned in this specification are incorporated herein by reference in their entireties.

Definitions

The expression "FXI," and the like, also known as "coagulation factor XI" or "Factor XI", refers to the human plasma serine protease (unless designated as being from another species) comprising the amino acid sequence as set forth in amino acid residues 19 through 625 of accession number NP_000119.1 (SEQ ID NO: 21). Human FXI containing a myc-myc-hexahistidine tag is shown as SEQ ID NO: 22 (with amino acid residues 1-607 being human FXI and amino acid residues 608-635 being the myc-myc-hexahistidine tag).

In certain instances, cell lines were prepared that expressed the FXI proteins, subunits of the FXI protein, and chimera proteins containing one or more FXI subunits, tag sequences, and plasma kallikrein protein sequences. For example, SEQ ID NO: 23 (construct hFXI_PKA1) is a chimera containing, at amino acids 1-85, the apple 1 domain (PKA1) of human kallikrein B1 (amino acids G20-C104 of human kallikrein B1 [SEQ ID NO: 28]), at amino acids 86-606, amino acids H105-V625 of human FXI (hFXI), and at amino acids 607-634, the myc-myc-hexagistidine tag.

For example, SEQ ID NO: 24 (construct hFXI_PKA2) is a chimera containing, at amino acids 1-90, amino acids E19-S108 of hFXI, at amino acids 91-174, the apple 2 domain (PKA2, also referred to as "A2") of hKLKB1 (amino acids C111-C193 SEQ ID NO: 28), at amino acids 175-605, amino acids A195-V625 of hFXI, and at amino acids 606-633, the myc-myc-hexagistidine tag.

For example, SEQ ID NO: 25 (construct hFXI_PKA3) is a chimera containing, at amino acids 1-180, amino acids E19-L198 of hFXI, at amino acids 181-264, the apple 3 domain (PKA3) of hKLKB1 (amino acids C201-C284 SEQ ID NO: 28), at amino acids 265-605, amino acids H285-V625 of hFXI, and at amino acids 606-633, the myc-myc-hexagistidine tag.

For example, SEQ ID NO: 26 (construct hFXI_PKA4) is a chimera containing, at amino acids 1-271, amino acids E19-V289 of hFXI, at amino acids 272-355, the apple 4 domain (PKA4) of hKLKB1 (amino acids C292-C375 SEQ ID NO: 28), at amino acids 356-605, amino acids M376-V625 of hFXI, and at amino acids 606-633, the myc-myc-hexagistidine tag.

For example, SEQ ID NO: 27 (construct hKLKB1.mmh) is a chimera containing, at amino acids 1-619, amino acids G20-A638 of hKLKB1, and at amino acids 620-647, the myc-myc-hexagistidine tag.

As used herein, the expression "anti-FXI antibody" includes both monovalent antibodies with a single specificity, as well as bispecific antibodies comprising a first arm that binds FXI and a second arm that binds a second (target) antigen, wherein the anti-FXI arm comprises any of the HCVR/LCVR or CDR sequences as set forth in Table 1 herein. The expression "anti-FXI antibody" also includes antibody-drug conjugates (ADCs) comprising an anti-FXI antibody or antigen-binding portion thereof conjugated to a drug or toxin (i.e., cytotoxic agent). The expression "anti-FXI antibody" also includes antibody-radionuclide conjugates (ARCs) comprising an anti-FXI antibody or antigen-binding portion thereof conjugated to a radionuclide.

The term "anti-FXI antibody", as used herein, means any antigen-binding molecule or molecular complex comprising at least one complementarity determining region (CDR) that specifically binds to or interacts with FXI or a portion of FXI or an apple 2 domain of FXI or an epitope within an apple 2 domain of FXI. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-FXI antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full length antibody molecules. The terms "antigen-binding portion" of an antibody, "antigen-binding fragment" of an antibody, and the like, as used herein, include any enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

In certain instances, it may be desirable to antagonize FXI, for example, for inhibiting the formation of blood clots. However, the antibodies of the present disclosure act as antagonist antibodies, which serve as inhibitors of FXI or FXIa activity and concomitantly serve as inhibitors of intrinsic pathway thrombosis/clot formation. The antibodies of the present disclosure may function by preventing the interaction between FXI and its upstream activators coagulation factor XII (FXII) and/or coagulation faction II (FII or thrombin). The antibodies of the present disclosure may also function by preventing the interaction between FXI and its downstream target coagulation factor IX (FIX). The antibodies of the present disclosure may also function by sequestering FXI from the blood stream of a patient.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies of the disclosure may, in some embodiments, be recombinant and/or non-naturally occurring human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region, which may be desirable, for example, in production, to improve the yield of the desired antibody form.

The term "specifically binds", or "binds specifically to", or the like, means that an antibody, or antigen-binding fragment thereof, forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to FXI. Moreover, multi-specific antibodies that bind to FXI protein and one or more additional antigens or a bi-specific that binds to two different regions of FXI are nonetheless considered antibodies that "specifically bind", as used herein.

The antibodies of the disclosure may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-FXI antibodies disclosed herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or antagonistic biological properties (as the case may be), reduced immunogenicity, etc. Antibodies and antigen-binding fragments obtained in this general manner are encompassed within the present disclosure.

The present disclosure also includes anti-FXI antibodies comprising variants of any of the HCVR, LCVR, and/or CDR amino acid sequences disclosed herein having one or more conservative substitutions. For example, the present disclosure includes anti-FXI antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Characteristics of the Antibodies

The present disclosure includes anti-FXI antibodies that bind the A2 domain of human FXI with a $K_D$ of less than about 500 pM as measured by surface plasmon resonance at 25° C., or at 37° C. According to certain embodiments, the disclosure includes anti-FXI antibodies that bind human FXI with a $K_D$ of less than about 400 pM, less than about 300 pM, less than about 200 pM, less than about 150 pM, less than about 100 pM, less than about 80 pM, less than about 50 pM, less than about 40 pM, less than about 30 pM, less than about 20 pM, less than about 10 pM, less than about 5 pM, less than about 3 pM, or less than about 1 pM.

The present disclosure includes anti-FXI antibodies that bind activated human FXI (FXIa) with a $K_D$ of less than about 1,000 pM as measured by surface plasmon resonance at 25° C., or at 37° C. According to certain embodiments, the disclosure includes anti-FXI antibodies that bind human FXI with a $K_D$ of less than about 900 pM, less than about 800 pM, less than about 700 pM, less than about 500 pM, less than about 250 pM, less than about 100 pM, less than about 80 pM, less than about 50 pM, less than about 40 pM, less than about 30 pM, less than about 20 pM, less than about 10 pM, less than about 5 pM, less than about 3 pM, or less than about 1 pM.

The present disclosure includes anti-FXI antibodies that bind human FXI with a dissociative half life (t½) of greater than about 10 minutes as measured by surface plasmon resonance at 25° C., or 37° C. According to certain embodiments, the disclosure includes anti-FXI antibodies that bind human FXI with a t½ of greater than about 20 minutes, greater than about 50 minutes, greater than about 100 minutes, greater than about 120 minutes, greater than about 150 minutes, greater than about 300 minutes, greater than about 350 minutes, greater than about 400 minutes, greater than about 450 minutes, greater than about 500 minutes, greater than about 550 minutes, greater than about 600 minutes, greater than about 700 minutes, greater than about 800 minutes, greater than about 900 minutes, greater than about 1000 minutes, greater than about 1100 minutes, or greater than about 1200 minutes.

The present disclosure includes anti-FXI antibodies that bind human FXIa with a dissociative half life (t½) of greater than about 10 minutes as measured by surface plasmon resonance at 25° C., or 37° C. According to certain embodiments, the disclosure includes anti-FXI antibodies that bind human FXI with a t½ of greater than about 20 minutes, greater than about 50 minutes, greater than about 100 minutes, greater than about 120 minutes, greater than about 150 minutes, greater than about 300 minutes, greater than about 350 minutes, greater than about 400 minutes, greater than about 450 minutes, greater than about 500 minutes, greater than about 550 minutes, greater than about 600 minutes, greater than about 700 minutes, greater than about 800 minutes, greater than about 900 minutes, greater than about 1000 minutes, greater than about 1100 minutes, or greater than about 1200 minutes.

The present disclosure includes anti-FXI antibodies that may or may not bind non-human FXI. As used herein, an antibody "does not bind" a particular antigen (e.g., monkey, mouse or rat FXI if the antibody, when tested in an antigen binding assay such as surface plasmon resonance exhibits a $K_D$ of greater than about 1000 nM, or does not exhibit any antigen binding, in such an assay. Another assay format that can be used to determine whether an antibody binds or does not bind a particular antigen, according to this aspect of the disclosure, is ELISA.

It is generally known in the art that activated FXI (FXIa) activates Factor IX by selectively cleaving arg-ala and arg-val peptide bonds. Factor IXa, in turn, forms a complex with Factor VIIIa (FIXa-FVIIIa) and activates Factor X. The present disclosure includes anti-FXI antibodies that inhibit FXI-mediated activation of human FX in plasma by at least about 85% with an $IC_{50}$ of less than about 100 pM. Using an assay format described in Example 4, or a substantially similar assay format, an $IC_{50}$ value can be calculated as the concentration of antibody required to activate FXI-mediated signaling to the half-maximal signal observed. Thus, according to certain embodiments, the disclosure includes anti-FXI antibodies that mediate human FXI-mediated activation of human FX in plasma by at least about 85% with an $IC_{50}$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, or less than about 5 pM, as measured using the assay format described in Example 4 herein or a substantially similar assay.

The present disclosure also includes anti-FXI antibodies that inhibit FXIa-mediated activation of human FX in plasma by at least about 25% with an $IC_{50}$ of less than about 50 pM. Using an assay format described in Example 4, or a substantially similar assay format, an $IC_{50}$ value can be calculated as the concentration of antibody required to activate FXIa-mediated signaling to the half-maximal signal observed. Thus, according to certain embodiments, the disclosure includes anti-FXI antibodies that mediate human FXIa-mediated activation of human FX in plasma by at least about 25% with an $IC_{50}$ of less than about 200 pM, less than about 300 pM, less than about 200 pM, less than about 100 pM, less than about 50 pM, less than about 40 pM, less than about 30 pM, less than about 20 pM, less than about 10 pM, less than about 9 pM, less than about 8 pM, less than about 7 pM, less than about 6 pM, less than about 5 pM, less than about 4 pM, less than about 3 pM, less than about 2 pM, or less than about 1 pM, as measured using the assay format described in Example 4 herein or a substantially similar assay.

The present disclosure includes anti-FXI antibodies that preferentially bind to the apple 2 domain (A2) as demonstrated by direct binding to A2 domain constructs or by competing with one or more specific A2-binding antibodies as shown in Example 5 and Example 6 respectively. In one embodiment, the antibodies, or antigen-binding fragments thereof, disclosed herein do not bind the catalytic domain of FXI.

The present disclosure includes anti-FXI antibodies that prolong the activated partial thromboplastin time (aPTT), which is a measure of intrinsic pathway thrombogenesis, while having no measureable effect on prothrombin time (PT), which is a measure of extrinsic pathway thrombogenesis, in human plasma. In one embodiment, the aPTT is measured in pooled human plasma treated with ellagic acid and the PT is measured in pooled human plasma treated with tissue factor using a hemostasis analyzer as exemplified in Example 7. It is generally known in the art that ellagic acid stimulates the intrinsic pathway of thrombogenesis in vitro and tissue factor stimulates the extrinsic pathway of thrombogenesis. Here, the anti-FXI antibody prolongs aPTT about two-fold at a concentration of less than 100 nM, less than 90 nM, less than 80 nM, less than 70 nM, less than 60 nM, less than 50 nM, less than 40 nM, less than 30 nM, less than 20 nM, less than 10 nM, 1 nM-100 nM, 1 nM-100 nM, 1 nM-50 nM, 100 pM-50 nM, 5 nM-50 nM, 5 nM-40 nM, 5 nM-15 nM, 10 nM-20 nM, 15 nM-25 nM, 20 nM-30 nM, 25 nM-35 nM, 30 nM-40 nM, 35 nM-45 nM, 40 nM-50 nM, 45 nM-55 nM, 50 nM-60 nM, 55 nM-65 nM, 60 nM-100 nM, 65 nM-75 nM, 70 nM-80 nM, 75 nM-85 nM, 80 nM-90 nM, 85 nM-95 nM, 90 nM-100 nM, or 95 nM-105 nM, without doubling PT.

The present disclosure includes anti-FXI antibodies that inhibit the production of thrombin via the intrinsic pathway (intrinsic thrombin) in human plasma in vitro with little to no effect on the production of thrombin via the extrinsic pathway (extrinsic thrombin). In one embodiment, pathway-specific thrombin production is determined in vitro by a thrombin generation assay using a calibrated automated thrombogram as exemplified in Example 7. Here, a thrombin generation profile is generated and peak thrombin concentration is determined in ellagic acid treated plasma and in tissue factor treated plasma with and without an anti-FXI antibody. Thus, in one embodiment, anti-FXI antibodies inhibit the production of intrinsic thrombin at a concentration of 0.1 nM-100 nM, 1 nM-100 nM, 5 nM-500 nM, 5 nM-100 nM, 10 nM-100 nM, 10 nM-50 nM, 5 nM-15 nM, 10 nM-20 nM, 25 nM-35 nM, 30 nM-40 nM, 35 nM-45 nM, 40 nM-50 nM, 45 nM-55 nM, 50 nM-60 nM, 55 nM-65 nM, 60 nM-65 nM, ≥20 nM, ≥25 nM, ≥30 nM, ≥35 nM, ≥40 nM, ≥45 nM, ≥50 nM, ≥55 nM, ≥5 nM, ≥10 nM, or ≥15 nM. Here, the anti-FXI antibodies have no effect on the production of extrinsic thrombin with any concentration up to 500 nM.

The present disclosure includes anti-FXI antibodies that increase by at least two-fold activated partial thromboplastin time (aPTT) in a primate in vivo without measurably affecting prothrombin time (PT). Here, a primate is administered an anti-FXI antibody, plasma is obtained from the primate, the plasma is contacted with ellagic acid or tissue factor, and then the aPTT or PT respectively is determined in an assay as exemplified in Example 8. In one embodiment, the primate is a human. In one embodiment, the primate is a monkey.

In one embodiment, the anti-FXI antibody is administered parenterally at a dose of 0.01 mg/kg-20 mg/kg, 0.1 mg/kg-10 mg/kg, 1 mg/kg-10 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, or about 15 mg/kg.

In one embodiment, the aPTT is prolonged with the anti-FXI treatment relative to no anti-FXI treatment at least 1.5-fold, at least 2-fold, at least 2.5-fold, at least 3-fold, at least 3.5-fold, at least 4-fold, at least 4.5-fold, at least 5-fold, at least 5.5-fold, or at least 6-fold.

In one embodiment, the anti-FXI-mediated aPTT prolongation effect persists in the subject after receiving a dose of the anti-FXI antibody for at least 1 week, at least 2 weeks, at least 3 weeks, at least 4 weeks, at least 5 weeks, at least 6 weeks, at least 7 weeks, at least 8 weeks, at least 3 months, at least 4 months, at least 5 months, or at least 6 months.

The present disclosure includes anti-FXI antibodies that inhibit intrinsic pathway peak thrombin activity in a primate in vivo without measurably affecting extrinsic pathway peak thrombin activity. Here, a primate is administered an anti-FXI antibody, plasma is obtained from the primate, the plasma is contacted with ellagic acid or tissue factor, and then the generation of intrinsic thrombin or extrinsic thrombin respectively is determined in a thrombin generation assay as exemplified in Example 8. In one embodiment, the primate is a human. In one embodiment, the primate is a monkey.

In one embodiment, the anti-FXI antibody is administered parenterally at a dose of 0.01 mg/kg-20 mg/kg, 0.1 mg/kg-10 mg/kg, 1 mg/kg-10 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, or about 15 mg/kg.

In one embodiment, the peak intrinsic thrombin (i.e., the thrombin generated via ellagic acid) activity in the anti-FXI treatment relative to no anti-FXI treatment is inhibited by 1%-100%, 5%-95%, 10%-90%, 20%-80%, 1%-10%, 5%-20%, 10%-30%, 15%-40%, 20%-50%, 25%-60%, 5%-15%, 10%-20%, 15%-25%, 20%-30%, 25%-35%, 30%-40%, 35%-45%, 40%-50%, 45%-55%, 50%-60%, 55%-65%, 60%-70%, 65%-75%, 70%-80%, 75%-85%, 80%-90%, 85%-95%, 90%-100%, 95%-105%, or ≥100%.

In one embodiment, the anti-FXI-mediated inhibition of peak intrinsic thrombin activity persists in the subject after receiving a dose of the anti-FXI antibody for at least 1 week, at least 2 weeks, at least 3 weeks, at least 4 weeks, at least 5 weeks, at least 6 weeks, at least 7 weeks, at least 8 weeks, at least 3 months, at least 4 months, at least 5 months, or at least 6 months.

A binding characteristic of an antibody of the disclosure (e.g., any of the binding characteristics mentioned herein above), when disclosed in term of being "measured by surface plasmon resonance" means that the relevant binding characteristic pertaining to the interaction between the antibody and the antigen are measured using a surface plasmon resonance instrument (e.g., a Biacore® instrument, GE Healthcare) using standard Biacore assay conditions as illustrated in Example 3 herein, or substantially similar assay format. In certain embodiments, the binding parameters are measured at 25° C., while in other embodiments, the binding parameters are measured at 37° C.

The present disclosure includes antibodies or antigen-binding fragments thereof that specifically bind FXI, comprising an HCVR and/or an LCVR comprising an amino acid sequence selected from any of the HCVR and/or LCVR amino acid sequences listed in Table 1.

The antibodies of the present disclosure may possess one or more of the aforementioned biological characteristics, or any combination thereof. The foregoing list of biological characteristics of the antibodies of the disclosure is not intended to be exhaustive. Other biological characteristics of the antibodies of the present disclosure will be evident to a person of ordinary skill in the art from a review of the present disclosure including the working Examples herein.

Epitope Mapping and Related Technologies

The epitope to which the antibodies of the present disclosure bind may consist of a single contiguous sequence of 3 or more (e.g., 3, 4, 5, 6, 7, 8, 9, 10, 11, 12, 13, 14, 15, 16, 17, 18, 19, 20 or more) amino acids of a FXI protein. Alternatively, the epitope may consist of a plurality of non-contiguous amino acids (or amino acid sequences) of FXI. In some embodiments, the epitope is located on or near a surface of FXI, for example, in the domain that interacts with any one of its ligands, e.g., FXIIa, thrombin, and FIX. In other embodiments, the epitope is located on or near a surface of FXI that does not interact with the FXI ligand, e.g., at a location on the surface of FXI at which an antibody, when bound to such an epitope, does not interfere with the interaction between FXI and its ligand.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present disclosure includes anti-FXI antibodies that bind to the same epitope as any of the specific exemplary antibodies described herein (e.g. antibodies comprising any of the amino acid sequences as set forth in Table 1 herein). Likewise, the present disclosure also includes anti-FXI antibodies that compete for binding to FXI with any of the specific exemplary antibodies described herein (e.g. antibodies comprising any of the amino acid sequences as set forth in Table 1 herein).

One can easily determine whether an antibody binds to the same epitope as, or competes for binding with, a reference anti-FXI antibody by using routine methods known in the art and exemplified herein. For example, to determine if a test antibody binds to the same epitope as a reference anti-FXI antibody of the disclosure, the reference antibody is allowed to bind to an FXI protein. Next, the ability of a test antibody to bind to the FXI molecule is assessed. If the test antibody is able to bind to FXI following saturation binding with the reference anti-FXI antibody, it can be concluded that the test antibody binds to a different epitope than the reference anti-FXI antibody. On the other hand, if the test antibody is not able to bind to the FXI molecule following saturation binding with the reference anti-FXI antibody, then the test antibody may bind to the same epitope as the epitope bound by the reference anti-FXI antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-FXI antibody, the above-described binding methodology is performed in two orientations: In a first orientation, the reference antibody is allowed to bind to an FXI protein under saturating conditions followed by assessment of binding of the test antibody to the FXI molecule. In a second orientation, the test antibody is allowed to bind to a FXI molecule under saturating conditions followed by assessment of binding of the reference antibody to the FXI molecule. If, in both orientations, only the first (saturating) antibody is capable of binding to the FXI molecule, then it is concluded that the test antibody and the reference antibody compete for binding to FXI (see, e.g., the assay format described in the Examples herein, in which FXI protein is captured onto sensor tips and the FXI-coated sensor tips are treated with a reference antibody [mAb-1] and a test anti-FXI antibody [mAb-2] sequentially and in both binding orders). As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-FXI antibodies of the present disclosure can be fully human but non-naturally occurring, antibodies. Methods for generating monoclonal antibodies, including fully human monoclonal antibodies are known in the art. Any such known methods can be used in the context of the present disclosure to make human antibodies that specifically bind to human FXI.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to an allergen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

As described in the experimental section below, the high affinity chimeric antibodies, which are isolated having a human variable region and a mouse constant region, are characterized and selected for desirable characteristics, including affinity, selectivity, epitope, etc. The mouse constant regions are then replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

In certain embodiments, it may be desirable to test antihuman FXI antibodies in mice or rats that have been engineered to express a human FXI receptor. These mice or rats may be beneficial in circumstances wherein the anti-FXI antibodies may only bind human FXI, but will not cross react with mouse or rat FXI. Any method known to those skilled in the art may be used for generating such FXI humanized mice and rats.

In general, the antibodies of the instant disclosure possess very high affinities, typically possessing $K_D$ of from about $10^{-12}$ through about $10^{-9}$ M, when measured by binding to antigen either immobilized on solid phase or in solution phase.

Bioequivalents

The anti-FXI antibodies and antibody fragments of the present disclosure encompass proteins having amino acid sequences that vary from those of the described antibodies but that retain the ability to bind human FXI. Such variant antibodies and antibody fragments comprise one or more additions, deletions, or substitutions of amino acids when compared to parent sequence, but exhibit biological activity that is essentially equivalent to that of the described antibodies. Likewise, the anti-FXI antibody-encoding DNA sequences of the present disclosure encompass sequences that comprise one or more additions, deletions, or substitutions of nucleotides when compared to the disclosed sequence, but that encode an anti-FXI antibody or antibody fragment that is essentially bioequivalent to an anti-FXI antibody or antibody fragment of the disclosure. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-FXI antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-FXI antibody variants comprising amino acid changes which modify the glycosylation characteristics of the antibodies, e.g., mutations which eliminate or remove glycosylation.

Species Selectivity and Species Cross-Reactivity

The present disclosure, according to certain embodiments, provides anti-FXI antibodies that bind to human FXI but not to FXI from other species. The present disclosure also includes anti-FXI antibodies that bind to human FXI and to FXI from one or more non-human species. For example, the anti-FXI antibodies of the disclosure may bind to human FXI and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee FXI. According to certain exemplary embodiments of the present disclosure, anti-FXI antibodies are provided which specifically bind human FXI but do not bind, or bind only weakly, to mouse or rat FXI.

Multispecific Antibodies

The antibodies of the present disclosure may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-FXI antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present disclosure includes bispecific antibodies wherein one arm of an immunoglobulin binds human FXI, and the other arm of the immunoglobulin is specific for a second antigen. The FXI-binding arm can comprise any of the HCVR/LCVR or CDR amino acid sequences as set forth in Table 1 herein.

An exemplary bispecific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab² bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulations and Administration

The disclosure provides pharmaceutical compositions comprising the anti-FXI antibodies or antigen-binding fragments thereof of the present disclosure. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-FXI antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intravitreal, intraocular, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, intravitreal, intraocular, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present disclosure includes methods comprising administering to a subject in need thereof a therapeutic composition comprising an anti-FXI antibody (e.g., an anti-FXI antibody comprising any of the HCVR/LCVR or CDR sequences as set forth in Table 1 herein). The therapeutic composition can comprise any one or more of the anti-FXI antibodies or antigen-binding fragments thereof disclosed herein, and a pharmaceutically acceptable carrier or diluent.

The antibodies of the disclosure are useful, inter alia, for the treatment, prevention and/or amelioration of any disease or disorder associated with or mediated by FXI expression or activity. The FXI antagonist antibodies of the disclosure may be used to treat or prevent thrombosis, especially thrombosis of the intrinsic pathway, while minimizing negatively impacting hemostasis and clot formation via the extrinsic pathway.

The present disclosure includes methods of treating or preventing thrombosis by administering to a patient in need of such treatment an anti-FXI antibody, or antigen-binding fragment thereof, as disclosed elsewhere herein.

In one embodiment, the anti-FXI antibodies of the disclosure may provide a method of treating or preventing thrombosis associated with any one or more of Factor V Leiden, prothrombin gene mutation, deficiencies of natural proteins that prevent clotting (such as antithrombin, protein C and protein S), elevated levels of homocysteine, elevated levels of fibrinogen or dysfunctional fibrinogen (dysfibrinogenemia), elevated levels of factor VIII, factor IX, and/or XI, abnormal fibrinolytic system, including hypoplasminogenemia, dysplasminogenemia and elevation in levels of plasminogen activator inhibitor (PAI-1), atrial fibrillation, cancer, side effects of some medications used to treat cancer, such as tamoxifen, bevacizumab, thalidomide and lenalidomide, recent trauma or surgery, central venous catheter placement, obesity, pregnancy, supplemental estrogen use, including oral contraceptive pills (birth control pills), hormone replacement therapy, prolonged bed rest or immobility, heart attack, congestive heart failure, stroke and other illnesses that lead to decreased activity, heparin-induced thrombocytopenia (decreased platelets in the blood due to heparin or low molecular weight heparin preparations), lengthy airplane travel, antiphospholipid antibody syndrome, deep vein thrombosis or pulmonary embolism, myeloproliferative disorders such as polycythemia vera or essential thrombocytosis, paroxysmal nocturnal hemoglobinuria, inflammatory bowel syndrome, HIV/AIDS, nephrotic syndrome, COVID-19 infection or spike protein immunization effects, and the like.

In the context of the methods of treatment described herein, the anti-FXI antibody may be administered as a monotherapy (i.e., as the only therapeutic agent) or in combination with one or more additional therapeutic agents.

Combination Therapies and Formulations

The present disclosure includes compositions and therapeutic formulations comprising any of the anti-FXI antibodies described herein in combination with one or more additional therapeutically active components, and methods of treatment comprising administering such combinations to subjects in need thereof.

The anti-FXI antibodies of the present disclosure may be co-formulated with one or more drugs used to treat Factor V Leiden, prothrombin gene mutation, deficiencies of natural proteins that prevent clotting (such as antithrombin, protein C and protein S), elevated levels of homocysteine, elevated levels of fibrinogen or dysfunctional fibrinogen (dysfibrinogenemia), elevated levels of factor VIII, factor IX, and/or XI, abnormal fibrinolytic system, including hypoplasminogenemia, dysplasminogenemia and elevation in levels of plasminogen activator inhibitor (PAI-1), atrial fibrillation, cancer, side effects of some medications used to treat cancer, such as tamoxifen, bevacizumab, thalidomide and lenalidomide, recent trauma or surgery, central venous catheter placement, obesity, pregnancy, supplemental estrogen use, including oral contraceptive pills (birth control pills), hormone replacement therapy, prolonged bed rest or immobility, heart attack, congestive heart failure, stroke and other illnesses that lead to decreased activity, heparin-induced thrombocytopenia (decreased platelets in the blood due to heparin or low molecular weight heparin preparations), lengthy airplane travel, antiphospholipid antibody syndrome, deep vein thrombosis or pulmonary embolism, myeloproliferative disorders such as polycythemia vera or essential thrombocytosis, paroxysmal nocturnal hemoglobinuria, inflammatory bowel syndrome, HIV/AIDS, nephrotic syndrome, COVID-19 infection or spike protein immunization effects, and the like.

The anti-FXI antibodies of the disclosure may also be administered and/or co-formulated in combination with antivirals, antibiotics, analgesics, antioxidants, COX inhibitors, and/or NSAIDs. The anti-FXI antibodies may also be used in conjunction with other types of therapy including stem cell therapy, glaucoma filtration surgery, laser surgery, or gene therapy.

The additional therapeutically active component(s), e.g., any of the agents listed above or derivatives thereof, may be administered just prior to, concurrent with, or shortly after the administration of an anti-FXI antibody of the present disclosure; (for purposes of the present disclosure, such administration regimens are considered the administration of an anti-FXI antibody "in combination with" an additional therapeutically active component). The present disclosure includes pharmaceutical compositions in which an anti-FXI antibody of the present disclosure is co-formulated with one or more of the additional therapeutically active component(s) as described elsewhere herein.

Administration Regimens

According to certain embodiments of the present disclosure, multiple doses of an anti-FXI antibody (or a pharmaceutical composition comprising a combination of an anti-FXI antibody and any of the additional therapeutically active agents mentioned herein) may be administered to a subject over a defined time course. The methods according to this aspect of the disclosure comprise sequentially administering to a subject multiple doses of an anti-FXI antibody of the disclosure. As used herein, "sequentially administering" means that each dose of anti-FXI antibody is administered to the subject at a different point in time, e.g., on different days separated by a predetermined interval (e.g., hours, days, weeks or months). The present disclosure includes methods which comprise sequentially administering to the patient a single initial dose of an anti-FXI antibody, followed by one or more secondary doses of the anti-FXI antibody, and optionally followed by one or more tertiary doses of the anti-FXI antibody.

The terms "initial dose," "secondary doses," and "tertiary doses," refer to the temporal sequence of administration of the anti-FXI antibody of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-FXI antibody, but generally may differ from one another in terms of frequency of administration. In certain embodiments, however, the amount of anti-FXI antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-FXI antibody, which is administered to a patient prior to the administration of the very next dose in the sequence with no intervening doses.

The methods according to this aspect of the disclosure may comprise administering to a patient any number of secondary and/or tertiary doses of an anti-FXI antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

Diagnostic Uses of the Antibodies

The anti-FXI antibodies of the present disclosure may also be used to detect and/or measure FXI, or FXI—expressing cells in a sample, e.g., for diagnostic purposes. For example, an anti-FXI antibody, or fragment thereof, may be used to diagnose a condition or disease characterized by aberrant expression (e.g., over-expression, under-expression, lack of expression, etc.) of FXI. Exemplary diagnostic assays for FXI may comprise, e.g., contacting a sample, obtained from a patient, with an anti-FXI antibody of the disclosure, wherein the anti-FXI antibody is labeled with a detectable label or reporter molecule. Alternatively, an unlabeled anti-FXI antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure FXI in a sample include enzyme-linked immunosorbent assay (ELISA), radioimmunoassay (RIA), and fluorescence-activated cell sorting (FACS).

Samples that can be used in FXI diagnostic assays according to the present disclosure include any tissue or fluid sample obtainable from a patient, which contains detectable quantities of FXI protein, or fragments thereof, under normal or pathological conditions. Generally, levels of FXI in a particular sample obtained from a healthy patient (e.g., a patient not afflicted with a disease or condition associated with abnormal FXI levels or activity) will be measured to initially establish a baseline, or standard, level of FXI. This baseline level of FXI can then be compared against the levels of FXI measured in samples obtained from individuals suspected of having a FXI related disease or condition.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to the A2 Domain of FXI

Human antibodies to the A2 Domain of FXI were generated in a mouse comprising DNA encoding human immunoglobulin heavy and kappa light chain variable regions. In one embodiment, the human antibodies were generated in a VELOCIMMUNE® mouse. In one embodiment, VelocImmune® (VI) mice were immunized with human FXI. The antibody immune response was monitored by FXI specific immunoassay. For example, sera were assayed for specific antibody titers to purified full-length FXI. Antibody-producing clones were isolated using both B-cell Sorting Technology (BST) and hybridoma methods. For example, when a desired immune response was achieved, splenocytes were harvested and fused with mouse myeloma cells to preserve their viability and form hybridoma cell lines. The hybridoma cell lines were screened and selected to identify cell lines that produce FXI-specific antibodies.

Anti-FXI antibodies were also isolated directly from antigen-positive mouse B cells without fusion to myeloma cells, as described in U.S. Pat. No. 7,582,298, herein specifically incorporated by reference in its entirety. Using this method, several fully human anti-FXI antibodies (i.e., antibodies possessing human variable domains and human constant domains) were obtained.

The biological properties of the exemplary antibody generated in accordance with the methods of this Example, controls, and comparators are described in detail in the Examples set forth below.

Example 2: Heavy and Light Chain Variable Region Sequences

Table 1, columns 2 and 4 set forth the amino acid sequence identifiers of the heavy and light chain variable regions and CDRs of exemplary anti-FXI antibodies of the disclosure. The corresponding nucleic acid sequence identifiers for the exemplar anti-FXI antibodies of the disclosure is set forth in Table 1, columns 3 and 5.

TABLE 1

Anti-FXI Antibody Sequence Identifiers

| Antibody Part | REGN9933 Amino Acid SEQ ID NO | REGN9933 Nucleic Acid SEQ ID NO | H4H29801P2 Amino Acid SEQ ID NO | H4H29801P2 Nucleic Acid SEQ ID NO |
|---|---|---|---|---|
| Full Length Heavy Chain (HC) | 1 | 2 | 29 | 30 |
| Heavy Chain Variable Region (HCVR) | 3 | 4 | 31 | 32 |
| HCDR1 | 5 | 6 | 33 | 34 |
| HCDR2 | 7 | 8 | 35 | 36 |
| HCDR3 | 9 | 10 | 37 | 38 |
| Full Length Light Chain | 11 | 12 | 11 | 12 |
| Light Chain Variable Region (LCVR) | 13 | 14 | 13 | 14 |
| LCDR1 | 15 | 16 | 15 | 16 |
| LCDR2 | 17 | 18 | 17 | 18 |
| LCDR3 | 19 | 20 | 19 | 20 |

SEQ ID NO: 17 comprises the following one-letter amino acid sequence: AAS.

SEQ ID NO: 18 comprises the following nucleotide sequence: GCTGCATCC.

The exemplary full length anti-FXI antibody contains fully human Fc gamma 4 heavy chain (i.e., IgG4 Fc) and fully human light chain sequences. However, as will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain Control Construct Used in the Following Examples The control construct (anti-FXI A2 domain antibody) labeled as COMP3448 was included in the experiments disclosed herein, for comparative purposes: "a monoclonal antibody specific for fXI" having VH/VL sequences of antibody "14E11" according to U.S. Pat. No. 8,388,959, the entire contents of which are expressly incorporated herein by reference in their entirety.

Example 3: Biacore Binding Kinetics of Anti-FXI Monoclonal Antibodies Binding to Different FXI Reagents Measured at 25° C. and 37° C.

Equilibrium dissociation constant ($K_D$) for different FXI reagents binding to purified anti-FXI monoclonal antibodies were determined using a real-time surface plasmon resonance based Biacore 8K biosensor. All binding studies were performed in 10 mM HEPES, 300 mM NaCl, and 0.05% v/v Surfactant Tween-20, pH 7.4 (HBS-P) running buffer at 25° C. and 37° C. The Biacore CM5 sensor chip surface was first derivatized by amine coupling with the mouse anti-human Fc specific monoclonal antibody (Regeneron, Tarrytown) to capture anti-FXI monoclonal antibodies. Binding studies were performed on human FXI (zymogen; Factor XI protein, human plasma, Enzyme Research Laboratories, South Bend, IN, cat. HFXI 1111) and FXIa (activated; Factor XIa protein, human plasma, Enzyme Research Laboratories, South Bend, IN, cat. HFXIa 1111a). Different concentrations of hFXI and hFXIa (25 nM-0.39 nM; 4-fold serial dilution) (were first prepared in HBS-P running buffer and were injected over anti-human Fc captured anti-FXI monoclonal antibody surface for 3 minutes at a flow rate of 30 µL/minute, while the dissociation of monoclonal antibody bound FXI reagent was monitored for 10 minutes in HBS-P running buffer. The association rate ($k_a$) and dissociation rate ($k_d$) were determined by fitting the real-time binding sensorgrams to a 1:1 binding model with mass transport limitation using Scrubber 2.0 c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2}{60*kd} \qquad \text{Eq. 1}$$

Binding kinetics parameters for hFXI or hFXIa binding to the subject anti-FXI monoclonal antibody of the disclosure and an isotype control at 25° C. and 37° C. are shown in Table 2 and Table 3.

At 25° C., anti-FXI monoclonal antibodies bound to hFXI with KD values ranging from 35.1 pM to 7.53 pM, as shown in Table 2. At 37° C., anti-hFXI monoclonal antibodies bound to hFXI with KD values ranging from 13.7 pM to 48.3 pM, as shown in Table 2.

At 25° C., anti-FXI monoclonal antibodies bound to hFXIa with KD values ranging from 257 pM to 269 pM, as shown in Table 3. At 37° C., anti-FXI monoclonal antibodies bound to hFXIa with KD values ranging from 763 pM to 893 pM, as shown in Table 3.

TABLE 2

Binding kinetics parameters of hFXI to anti-FXI monoclonal antibodies and an isotype control.

| Target/ Temp (° C.) | mAb Captured | mAb Capture Level (RU) | 25 nM Ag Bound (RU) | $k_a$ (1/Ms) | $k_d$ (1/s) | KD (M) | t½ (min) |
|---|---|---|---|---|---|---|---|
| hFXI (25° C.) | REGN9933 | 347.8 ± 1.2 | 195 | 3.26E+05 | 1.15E−05 | 3.51E−11 | 1008 |
|  | H4H29801P2 | 373.5 ± 0.7 | 188.1 | 2.57E+05 | 1.94E−05 | 7.53E−11 | 596.4 |
|  | Isotype control [REGN1945] | 413.0 ± 0.6 | 1.3 | NB | NB | NB | NB |
| hFXI (37° C.) | REGN9933 | 445.4 ± 1.5 | 266.8 | 7.29E+05 | ≤1.00E−05 | 1.37E−11 | ≥1155 |
|  | H4H29801P2 | 470.7 ± 0.9 | 247 | 4.90E+05 | 2.37E−05 | 4.83E−11 | 488 |
|  | Isotype control [REGN1945] | 614.8 ± 0.8 | 3.2 | NB | NB | NB | NB |

NB: No binding;
IC: Inconclusive

TABLE 3

Binding kinetics parameters of hFXIa to anti-FXI monoclonal antibodies and an isotype control.

| Target/ Temp (° C.) | mAb Captured | mAb Capture Level (RU) | 25 nM Ag Bound (RU) | $k_a$ (1/Ms) | $k_d$ (1/s) | KD (M) | t½ (min) |
|---|---|---|---|---|---|---|---|
| hFXIa (25° C.) | REGN9933 | 346.7 ± 1.6 | 247.1 | 5.91E+05 | 1.52E−04 | 2.57E−10 | 76 |
|  | H4H29801P2 | 372.0 ± 1.5 | 249.3 | 4.40E+05 | 1.18E−04 | 2.69E−10 | 97.7 |
|  | Isotype control [REGN1945] | 70.5 ± 33.5 | −1.4 | NB | NB | NB | NB |
| hFXIa (37° C.) | REGN9933 | 425.1 ± 13.9 | 227.3 | 6.38E+05 | 4.87E−04 | 7.63E−10 | 23.7 |
|  | H4H29801P2 | 450.4 ± 13.1 | 211.1 | 6.03E+05 | 5.39E−04 | 8.93E−10 | 21.4 |
|  | Isotype control [REGN1945] | 612.7 ± 1.8 | 0.3 | NB | NB | NB | NB |

NB: No binding;
IC: Inconclusive

Example 4: Activated Partial Thromboplastin Time Bioassay

Experimental Procedure:

A BIOPHEN Factor XIa kit (HYPHEN BioMed, Neuville-sur-Oise, FR, cat. #220412) was used to assess the capacity of the anti-FXI antibody of disclosure to inhibit the activity of the zymogen Factor FXI (FXI) or pre-activated FXIa leading to the generation of active Factor Xa (FXa). Inhibition by the antibodies of the disclosure was determined by measuring a decrease in the amount of chromogenic substrate converted by FXa (BIOPHEN kit component R3). All the reagents in the BIOPHEN kit were used in the assay except for except Reagent 1B (Human Factor IX) and the FXIa calibrator (Cal).

$$\% \text{ Inhibition} = 100 \times \frac{Absorbance_{Dilute\ plasma} - Absorbance_{Inhibition}}{Absorbance_{Dilute\ plasma} - Absorbance_{No\ Plasma\ control}} \quad \text{Eq. 2}$$

In this equation, "$Absorbance_{Dilute\ plasma}$" refers to the absorbance measurement at 405 nm of dilute plasma (either 0.13% or 0.15% plasma) that has been activated with 0.32 µM aPTT-XL Ellagic Acid to cleave FXI to FXIa without any added antibody. "$Absorbance_{Inhibition}$" refers to the minimum absorbance measurement at 405 nm from a dose response of a particular antibody with dilute plasma, activated by 0.32 µM Ellagic Acid. "$Absorbance_{No\ Plasma\ control}$" refers to the absorbance measurement at 405 nm of Tris-BSA buffer alone in the absence of any plasma.

TABLE 4

Anti-FXI/FXIa antibody inhibition of FXI activation to FXIa or preactivated FXIa activity in aPTT-XL Ellagic Acid Assay.

| | 0.13% Plasma | | | | 0.15% Plasma | | | |
| --- | --- | --- | --- | --- | --- | --- | --- | --- |
| | FXI | | FXIa | | FXI | | FXIa | |
| Antibody | % Inhibition | IC50 [M] | % Inhibition | IC50 [M] | % Inhibition | IC50 [M] | % Inhibition | IC50 [M] |
| REGN9933 | 85 | 3.9E−11 | 25 | >1.0E−08 | not tested | not tested | not tested | not tested |
| H4H29801P | 87 | 2.2E−10 | 22 | 6.8E−10 | not tested | not tested | not tested | not tested |
| Comp mAb [REGN3448] | 86 | 2.7E−11 | 35 | >1.0E−08 | 108 | 2.9E−11 | 38 | >5.0E−08 (38%) |
| Isotype Control mAb [REGN1945] | 58 | >1.0E−07 | no inhibition | no inhibition | 102 | 1.2E−07 | no inhibition | no inhibition |

To test the dose-dependent activity of FXI or FXIa, normal human plasma was initially diluted to 0.65% plasma in provided Tris-BSA buffer (used as dilution buffer for assay) and then serially diluted down to 0.021% plasma, along with a no plasma control. Normal human plasma was also diluted to either 0.13% or 0.15% plasma. The antibodies (anti-FXI, controls, and comparators) were serially diluted from a starting concentration of either 500 nM or 300 nM to a concentration of 5.1 pM with a buffer alone sample. For inhibition of zymogen FXI, the anti-FXI antibody was preincubated for 30 minutes at 25° C. with diluted plasma followed by another 30-minute incubation with 0.32 µM aPTT-XL ellagic acid at 25° C. For inhibition of active FXIa, diluted plasma was pre-activated with 0.32 µM aPTT-XL ellagic acid for 30 minutes at 25° C., followed by incubation with the anti-FXI antibody for 30 minutes at 25° C.

After incubations of the plasma with ellagic acid and antibody, Reagent 1A (Human FX, FVIII:C, fibrin polymerization inhibitor) was added and incubated for 5 minutes at 37° C. Then, Reagent 2 (thrombin, phospholipids, and calcium) was added and incubated for 5 minutes at 37° C. Finally, Reagent 3 (SXa-11 FXa substrate) was added and incubated for 30 minutes at 37° C. Absorbance was measured on the FLEXSTATION 3 Plate Reader (Molecular Devices, Sunnyvale, CA) at a wavelength of 405 nm. The results were analyzed using nonlinear regression (4-parameter logistics) with PRISM®6 software (GraphPad, La Jolla, CA) to obtain $EC_{50}$ and $IC_{50}$ values. The percent inhibition was calculated based on Equation 2 below:

As shown in Table 4, the anti-FXI/FXIa antibody showed inhibition of FXI in dilute normal plasma with $IC_{50}$ values ranging from 39 to 220 pM (in one example, 39 pM) with maximum inhibition ranging from 85 to 87% (in one example, 85%). The anti-FXI/FXIa antibody of the disclosure also inhibited FXIa in dilute plasma with $IC_{50}$ values ranging from 680 pM to greater than 10 nM (in one example, 10 nM) with maximum inhibition ranging from 22% to 25% in one example, 25%). The comparator mAb showed inhibition of FXI with $IC_{50}$ values ranging from 27 pM to 29 pM with maximum inhibition ranging from 86% to 106%. Comparator mAb also showed inhibition of FXIa with $IC_{50}$ values ranging from >10 nM to >5 nM with maximum inhibition ranging from 35% to 38%. Isotype Control mAb showed no inhibition of FXIa, but showed inhibition of FXI at high concentration of the antibody with $IC_{50}$ values ranging from >100 nM-120 nm with maximum inhibition ranging from 58-102% inhibition.

Example 5: Anti-FXI Binding Specificity to FXI Subunits

Binding specificity of various anti-FXI monoclonal antibodies to different truncated apple domains of human FXI was determined using a real time, label-free bio-layer interferometry assay on an OCTETHTX biosensor (Pall ForteBio Corp., Port Washington, NY). The experiment was performed at 25° C. in 10 mM HEPES, 150 mM NaCl, 3 mM EDTA, and 0.05% v/v surfactant TWEEN-20, 1 mg/mL bovine serum albumin (BSA), pH7.4 (HBS-EBT) buffer with the plate shaking at the speed of 1000 rpm. The binding of the anti-FXI monoclonal antibodies to their respective epitopes on recombinant human FXI proteins was tested using human FXI expressed with a C-terminal myc-myc-hexahistidine tag (hFXI-mmh; SEQ ID NO: 22), human FXI PKA1 domain expressed with a C-terminal myc-myc-hexahistidine tag (hFXI-PKA1-mmh; SEQ ID NO: 23), human FXI PKA2 domain expressed with a C-terminal myc-myc-hexahistidine tag (hFXI-PKA2-mmh; SEQ ID NO: 24), human FXI PKA3 domain expressed with a C-terminal myc-myc-hexahistidine tag (hFXI-PKA3-mmh; SEQ ID NO: 25), and human FXI PKA4 domain expressed with a C-terminal myc-myc-hexahistidine tag (hFXI-PKA4-mmh; SEQ ID NO: 26), collectively the FXI-mmh reagents. FXI-mmh reagents marked with PK (plasma kallikrein) have had the identified apple domain replaced by the corresponding PK apple domain, meaning that binding specificity is determined by non-binding to an antibody's respective epitope on the recombinant human FXI proteins described herein. For example, as hFXI-PKA2-mmh expresses plasma kallikrein apple domain 2, the subject mAb is postulated to bind only to hFXI-PKA1-mmh, hFXI-PKA3-mmh, and hFXI-PKA4-mmh, not hFXI-PKA2-mmh.

The FXI-mmh reagents were individually first captured onto anti-Penta-His antibody coated OCTET biosensor tips (Pall Fortebio Inc, cat. #18-5122) by submerging the biosensor tips for 2 minutes in wells each containing 100 nM solution of a human FXI-mmh reagent. The resultant antigen captured biosensor tips were then saturated individually with each anti-FXI monoclonal antibody by dipping into wells containing 133 nM solution of anti-FXI monoclonal antibody for 180 seconds. The biosensor tips were then washed in HBS-ETB buffer in between every step of the experiment. The real-time binding response was monitored during the entire course of the experiment and the binding response at the end of every step was recorded. The binding specificity response of anti-FXI monoclonal antibody was compared to different truncated FXI-mmh reagents as shown in Table 5.

anti-human FXI monoclonal antibody was first captured onto anti-hFc antibody coated (AHC) OCTET biosensor tips (Pall ForteBio Corp., #18-5060, Port Washington, NY) by submerging the tips for 5 minutes into wells containing a 50 µg/mL solution of anti-human FXI monoclonal antibody (subsequently referred to as the first mAb). The antibody captured biosensor tips were then saturated with a blocking H4H isotype (human IgG4) control monoclonal antibody (subsequently referred to as blocking mAb) by dipping into wells containing 50 µg/mL solution of blocking mAb for 4 minutes. The biosensor tips were then subsequently dipped into wells containing a co-complexed solution of 25 nM hFXI (ERL, #HFXI 1111) and 1 µM of a second anti-human FXI monoclonal antibody (subsequently referred to as the second mAb), that had been pre-incubated for 2 hours. The biosensor tips were washed in Octet HBS-P buffer in between every step of the experiment.

The real-time binding response was monitored during the course of the experiment and the binding response at the end of every step was recorded. The response of human FXI pre-complexed second mAb binding to the first mAb was corrected for background binding, compared and competitive/non-competitive behavior of different anti-FXI monoclonal antibodies was determined.

Table 6 explicitly defines the relationships of antibodies competing in both directions, independent of the order of binding. Here, the anti-FXI mAb REGN9933 competes for binding to plasma-derived hFXI with H4H29801P2, which is known to bind the A2 (apple 2) domain of FXI.

TABLE 5

Anti-FXI monoclonal antibodies binding to different human FXI domain proteins.

| | Binding Response to human FXI proteins with Addition of Antibody (nm) | | | | |
|---|---|---|---|---|---|
| Anti-FXI mAb | hFXI.mmh | hFXI PKA1.mmh | hFXI PKA2.mmh | hFXI PKA3.mmh | hFXI PKA4.mmh |
| REGN9933 | 0.83 | 0.28 | −0.12 | 0.48 | 0.29 |
| H4H29801P2 | 0.85 | 0.31 | −0.08 | 0.52 | 0.31 |
| iso-type negative control [REGN1945] | −0.01 | 0.04 | −0.11 | 0.03 | 0.02 |
| Comp mAb [COMP3448] | 0.86 | 0.26 | −0.13 | 0.44 | 0.27 |

Example 6: Competition Assays

6.1: Apple 2 Domain Competitive Binding

Binding competition between anti-FXI monoclonal antibodies was determined using a real time, label-free bio-layer interferometry assay on an OCTETHTX biosensor (Pall ForteBio Corp., Port Washington, NY). The entire experiment was performed at 25° C. in 0.01 M HEPES pH7.4, 0.15M NaCl, 0.05% v/v Surfactant Tween-20, 1 mg/mL BSA (Octet HBS-P buffer) with the plate shaking at the speed of 1000 rpm. To assess whether any 2 antibodies are able to compete with one another for binding to their respective epitopes on a human FXI (ERL) (Factor XI protein from human plasma, Ensyme Research Laboratories, South Bend, IN, cat. #HFXI 1111) around 1.5-2.8 nM of

TABLE 6

Antibody Cross-Competition Matrix

| First mAh Captured using AHC OCTET Biosensors | Second mAb Antibodies Shown to Compete with First mAb |
|---|---|
| Subject anti-FXI mAb [REGN9933] mAb-2 (FXI A3-A4 binder) | H4H29801P2 (A2 binder) |
| H4H29801P2 (A2 binder) | Subject anti-FXI mAb [REGN9933] |

6.2: FXI Competitive Binding

A second binding competition between anti-FXI monoclonal antibodies and a negative isotype control was conducted using the following materials and methods.

Materials
  Instrument used: Octet HTX 384 RED
  Temp: 25° C.
  Running Buffer: HBS-P+1 mg/ml BSA, pH 7.4
  Sensor type: ForteBIO Anti-hFc
  Capture flowrate/time: 1000 rpm, 300 sec (mAb-1), 300 sec association (Ag mAb-2 premix) 180 sec dissociation mAb-2

Methods

Approximately 1.5-2.8 nm of α-human FXI mAbs was captured by dipping α-hFc coated Octet biosensors in wells containing 50 µg/mL of α-human FXI mAbs for 5 minutes. H4H hFc (iso-type control) were used as negative controls. The unoccupied α-hFc Octet sensors were saturated by dipping in wells containing blocking mAb solution (50 µg/mL of H4H human Fc (iso-type control) 1) for 4 minutes. 25 nM of hFXI (ERL) was pre-incubated with 1 uM of α-FXI mAbs in buffer containing 50 µg/mL H4H hFc for at least 1 hour. Then blocking mAb saturated Octet biosensors were dipped in wells containing the pre-mix of αC5 mAb and hC5 for 5 minutes. At the end of each cycle, the α-hFc Octet sensors were regenerated in 10 mM HCl. During the analysis, self-self background signal (mAb binding to capture surface) was subtracted from entire column. Binding responses of mAb-1 were recorded and the competing/non-competing mAbs were binned based on their respective mAb-2 binding response.

Results and Discussion

The subject mAb REGN9933 and H4H29801P2 cross competed bidirectionally.

Example 7: Functional Plasma Assays for Clotting Time and Thrombin Generation (TGA)

Coagulation factors, along with platelets, are blood components relevant in the process of haemostasis during vessel injury. It is well-established that these components are drivers of thrombosis when imbalances occur in regulation (i.e., production and/or activity). Thrombotic diseases were believed to primarily arise from aberrant activation in the extrinsic pathway (via tissue factor), but more recently, clinical studies using anti-sense oligonucleotides to F11 prior knee arthroplasty was found to prevent post-operative venous thrombosis (Büller H R, Bethune C, Bhanot S, Gailani D, Monia B P, Raskob G E, Segers A, Verhamme P, Weitz J I. Factor XI antisense oligonucleotide for prevention of venous thrombosis. N Engl J Med. 2015 Jan. 15; 372(3): 232-40). Thus, inhibition of FXI activity is important for reduction of thrombotic coagulation (Weitz J I. Factor XI and factor XII as targets for new anticoagulants. Thromb Res. 2016 May; 141 Suppl 2: S40-5).

This example demonstrates that the anti-FXI antibody binds and inhibits the activity of human FXI in four functional plasma assays: 1) Activated Partial Thromboplastin Time (aPTT), 2) Prothrombin Time (PT), 3) Thrombin Generation Assay (TGA) triggered by ellagic acid and 4) TGA triggered by Tissue Factor. The aPTT test evaluates all clotting factors of the Intrinsic and Common pathways of the coagulation cascade by measuring time for a clot to form after the addition of calcium and ellagic acid, whereas the PT test evaluates all clotting factors of the Extrinsic and Common pathways of the coagulation cascade after the addition of calcium and Tissue Factor. The TGA triggered by

TABLE 7 hFXI (ERL) cross-competition on 4 lead anti-FXI BST using pre-mix format (5 × 5 matrix)

| mAb PID | binding domain | KD (M) | t1/2 (min) | capture | block | Subject mAb [REGN9933] | mab-1 [H4H29801P2] | mab-2 [A3/A4 binder] | Control [REGN1945] |
|---|---|---|---|---|---|---|---|---|---|
| Subject mAb [REGN9933] | A2 | 3.51E−11 | 1008.0 | 1.97 ± 0.07 | 0.43 ± 0.01 | 0.3 | 0.3* | 0.8 | 0.7 |
| H4H29801P2 | A2 | 4.10E−11 | ≥1155 | 2.52 ± 0.04 | 0.46 ± 0.01 | 0.1* | 0.2 | 0.9 | 0.7 |
| mAb-2** [A3/A4 binder] | A3-A4** | 1.18E−10 | 88.9 | 2.08 ± 0.06 | 0.42 ± 0.01 | 1.2 | 1.4 | 0.3 | 0.9 |
| Control [REGN1945] | none | NB | NB | 1.59 ± 0.06 | 0.62 ± 0.02 | 0.3 | 0.3 | 0.3 | 0.2 |

*Competition - Bidirectional
**Competition - Unidirectional

TABLE 8

Summary of binding interactions in cross competition study

| mAb PID | Binding domain | overlapping features | unique epitope bin | Comments |
|---|---|---|---|---|
| Subject mAb [REGN9933] | A2 | 1 | A | mAbs share one unique bin and an overlapping feature with comparator (data not shown) |
| H4H29801P2 | A2 | 1 | | (data not shown) |
| mAb-2 [A3/A4 binder] | A3-A4 | 5 | F | mAb shares one unique bin and an overlapping feature with comparator (data not shown) | ellagic acid measures the rate and amount of thrombin generated via the Intrinsic and Common pathways whereas TGA triggered by Tissue Factor measures the rate and amount of thrombin generated via the Extrinsic and Common pathways.

Experimental Procedure:

The aPTT was determined on Diagnostica STAGO START4 Hemostasis Analyzer (Daignostica Stago, Parsippany, NJ) in the following manner: A total of 50 μl of pooled normal human plasma was added to a cuvette at 37° C. After 1 minute, 5 μl of a 2× serially diluted test article (antibody or small molecule inhibitor) in PBS was added to the cuvette and allowed to incubate for 5 minutes. Then 50 μl of APPT-XL Ellagic Acid (Thermo Scientific, Waltham, MA) was added and allowed to incubate for 300 seconds before 50 μl of 20 mM calcium chloride (Thermo Scientific, Waltham, MA) was added to start the reaction. The measured clot time for the test article concentration was normalized to baseline (no drug) plasma clot time and plotted against log molar concentration of the test article. The results were analyzed using nonlinear regression (4-parameter logistics) with PRISM 5 software (GraphPad, La Jolla, CA) to obtain doubling time concentration.

The PT was determined on Diagnostica Stago START4 Hemostasis Analyzer (Daignostica Stago, Parsippany, NJ) in the following manner A total of 50 μl of pooled normal human plasma was added to a cuvette at 37° C. After 1 minute, 5 μl of a 2× serially diluted test article (antibody or small molecule inhibitor) in PBS was added to the cuvette and allowed to incubate for 5 min. Then 100 ul of Tissue Factor (TriniCLOT PT Excel, Diagnostica Stago, Parsippany, NJ, cat. #T1106) was added to start the reaction. The measured clot time for the test article concentration was normalized to baseline (no drug) plasma clot time and plotted against log molar concentration of the test article. The results were analyzed using nonlinear regression (4-parameter logistics) with PRISM 5 software (GraphPad, La Jolla, CA) to obtain doubling time concentration.

The thrombin generation profile under the intrinsic clotting pathway was determined in a Diagnostica Stago Calibrated Automated Thrombogram (Stago, Parsippany, NJ) in the following manner: A total of 55 μl of pooled normal human plasma was added to a well of a microplate at 37° C. Then 5 μl of a 2× serially diluted test article (antibody or small molecule inhibitor) in PBS was added to the well of the microplate and allowed to incubate for 30 min. 15 ul of APPT-XL Ellagic Acid (Thermo Scientific, Waltham, MA, cat. #95059-804) was diluted in microparticle (MP) reagent (Diagnostica Stago, cat. #86222) then added to the well and allowed to incubate for 45 minutes. Then 15 μl of Fluo Flu Cal substrate (Diagnostica Stago, cat. #86197) was added immediately before a continuous 90 min reading of the microplate. The measured real-time thrombin concentration values were plotted against time to yield a thrombogram profile for each concentration of the test article used.

The thrombin generation profile under the extrinsic clotting pathway was determined in a Diagnostica Stago Calibrated Automated Thrombogram (Diagnostica Stago, Parsippany, NJ) in the following manner: A total of 55 μl of pooled normal human plasma was added to a well of a microplate at 37° C. Then 5 μl of a 2× serially diluted test article (antibody or small molecule inhibitor) in PBS was added to the well of the microplate and allowed to incubate for 30 minutes. 15 μl of Tissue Factor PPP Reagent (Diagnostica Stago, cat. #86194) was added to the well and allowed to incubate for 45 min. Then 15 μl of Fluo Flu Cal substrate (Diagnostica Stago, cat. #86197) was added immediately before a continuous 90 minute reading of the microplate. The measured real-time thrombin concentration values were plotted against time to yield a thrombogram profile for each concentration of the test article used.

Results Summary and Conclusions:

Dose response curves were generated to determine the effect of each drug on plasma aPTT and PT. The IgG4 isotype control mAb (control mAb exerted no effect on aPTT (FIG. 1) or PT. REGN9933 prolonged the aPTT (FIG. 1) without increasing PT (not shown). An FXI-A2-binding comparator mAb (comp mAb) COMP3448 also prolonged the aPTT without increasing PT.

The efficiency of the drug to inhibit coagulation activity is indexed by an arbitrary "doubling time" concentration or C2xt, which is the concentration of drug required to prolong the clotting time by two-fold over the baseline value. These extrapolated C2xt values (i.e., curves cross the "Doubling Time Line") for the drugs and control discussed below. REGN9933 reached a C2xt with ≤33 nM for aPTT (intrinsic pathway). REGN9933 was not found to double the PT clotting time (extrinsic pathway) at the maximal 4 μM tested. The comp mAb COMP3448 required 62 nM to reach the aPTT C2xt but did not reach the PT C2xt with 4 μM. These data show the superiority of REGN9933 at achieving C2xt with a significantly lower concentration of antibody as compared to COMP3448.

Figure 2:
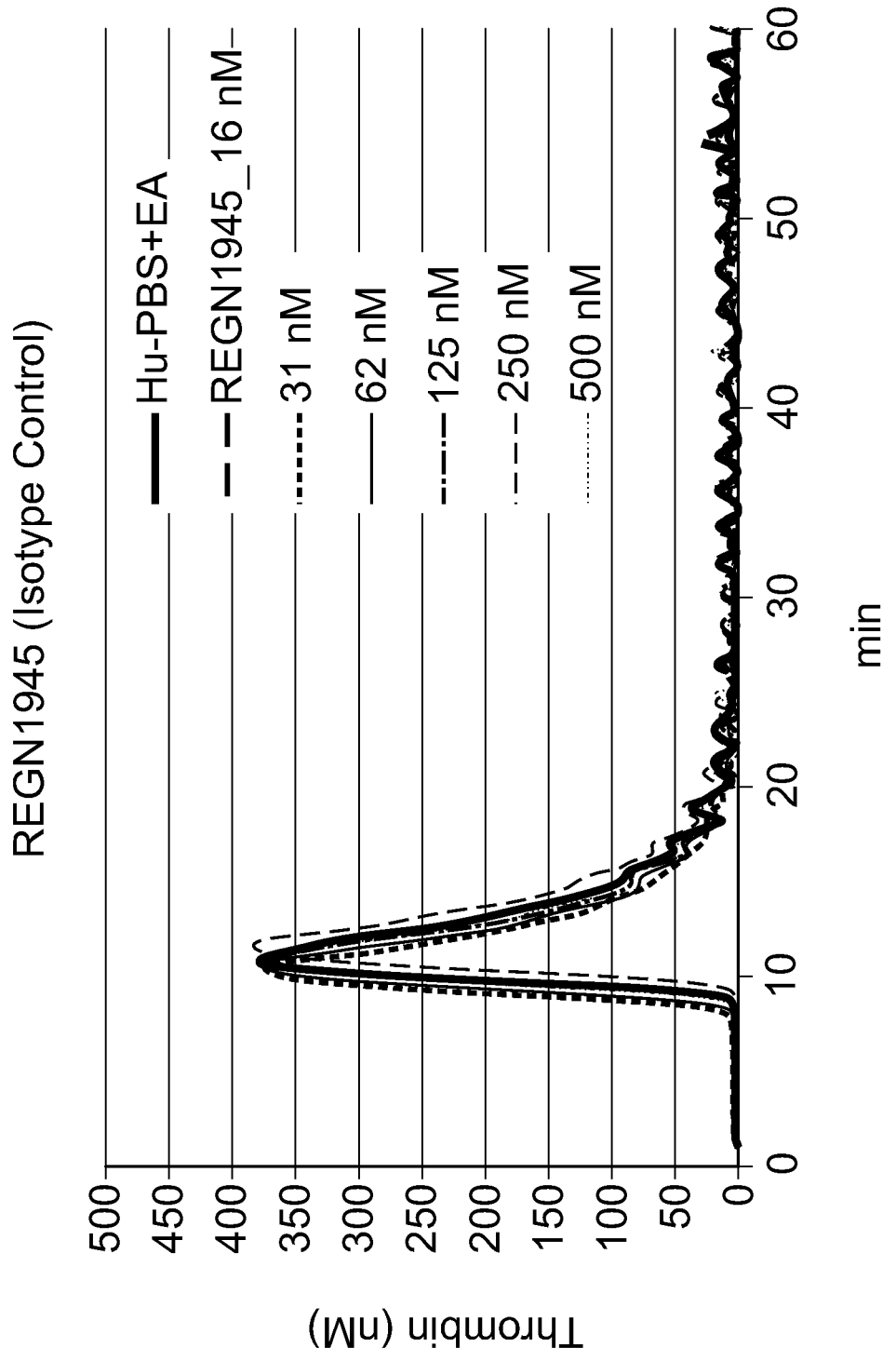
FIG. 2 depicts a line graph showing thrombin activity as a function of concentration of isotype control antibody (REGN1945) over time.
Figure 3:
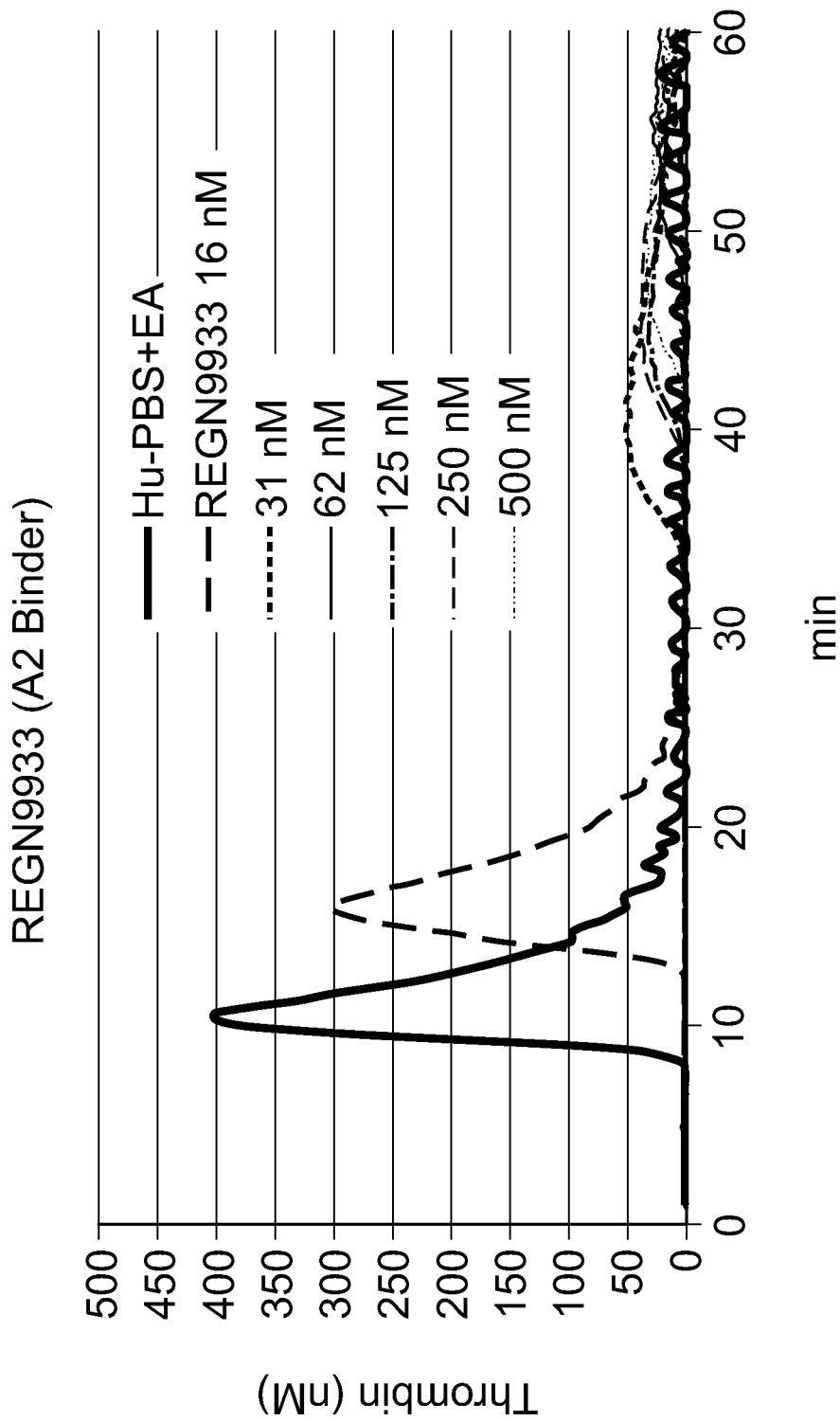
FIG. 3 depicts a line graph showing thrombin activity as a function of concentration of subject antibody (REGN9933) that binds FXI A2 over time.
Figure 4:
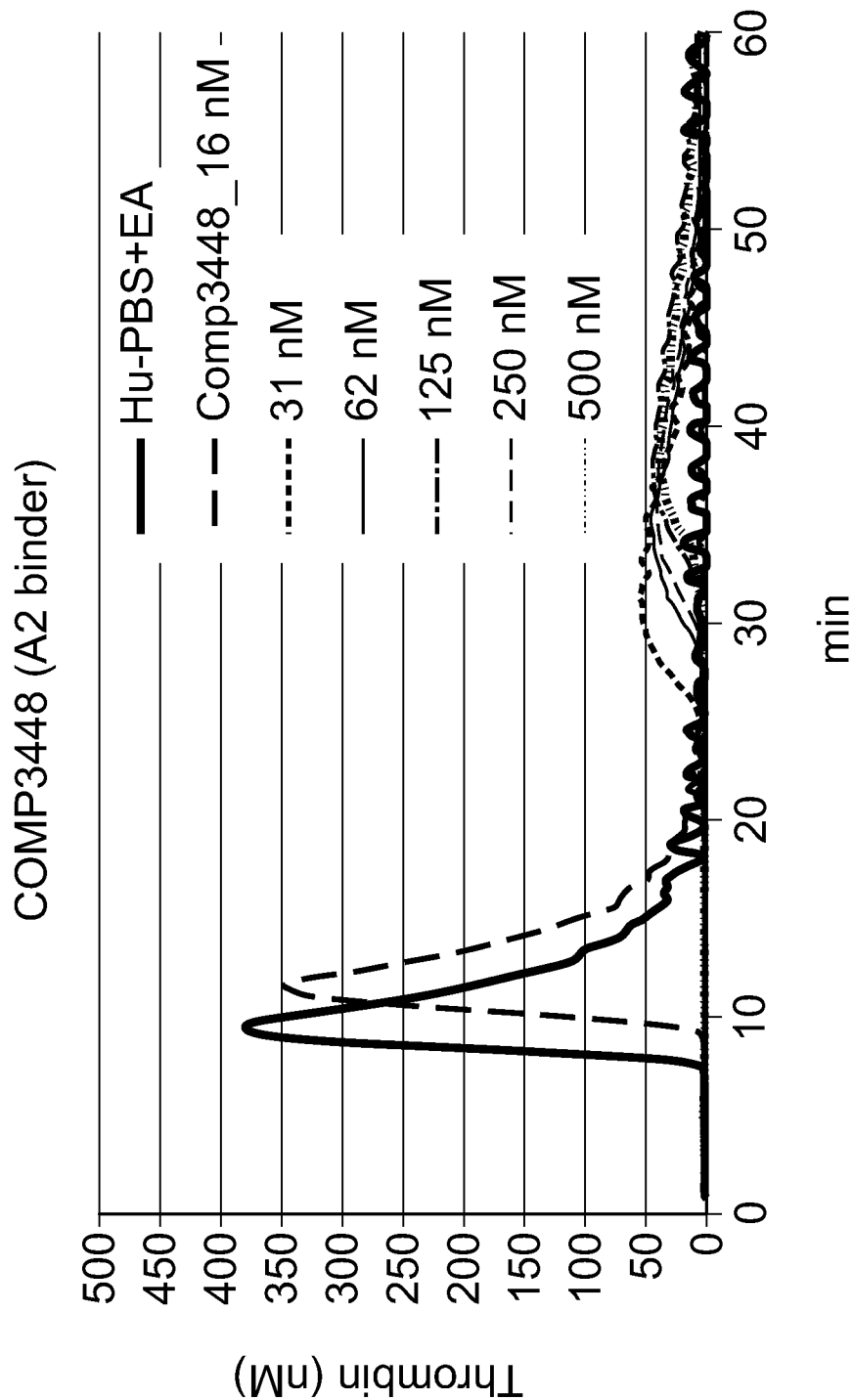
FIG. 4 depicts a line graph showing thrombin activity as a function of concentration of comparator antibody (COMP3448) that binds FXI A2 over time.

The effects of these mAbs were evaluated for their ability to inhibit thrombin generation (i.e., prolonged time to detection of thrombin=lag time, reduction in thrombin peak and reduction in total amount of thrombin generated=endogenous thrombin potential) when plasma was triggered by ellagic acid or Tissue Factor. The control mAb had no effect on thrombin generation (FIG. 2). The subject anti-FXI/FXIa mAb showed a slight reduction in thrombin generation at 16 nM but significantly or completely inhibited thrombin production at concentrations≥31 nM (FIG. 3), indicating that the subject anti-FXI mAb suppresses the intrinsic pathway activation that in turn prevents thrombin generation. The comp mAb showed a similar response as the subject anti-FXI/FXIa mAb on thrombin generation with a near complete inhibition at ≥31 nM (FIG. 4).

Figure 5:
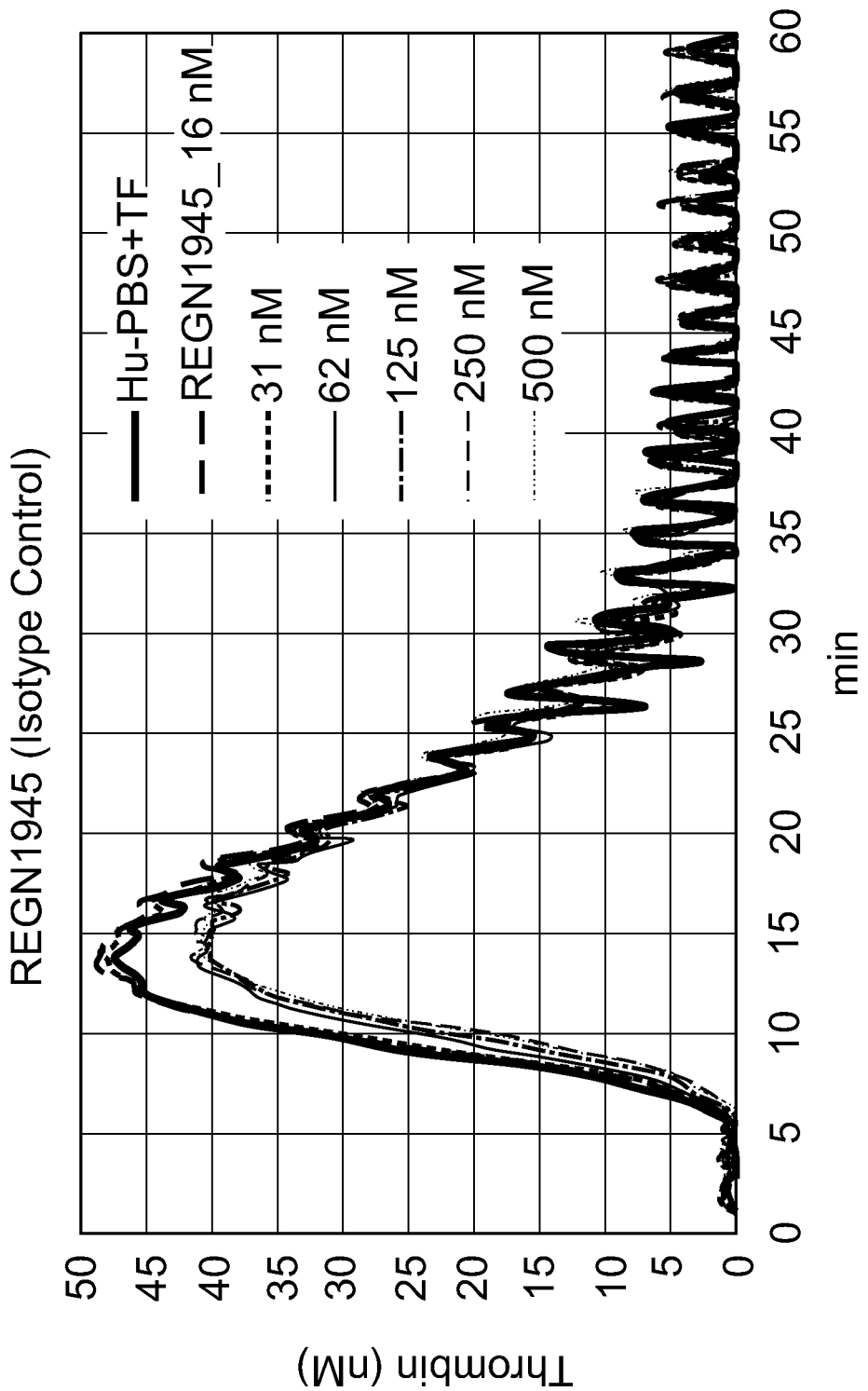
FIG. 5 depicts a line graph showing thrombin activity as a function of concentration of isotype control antibody (REGN1945) over time.
Figure 6:
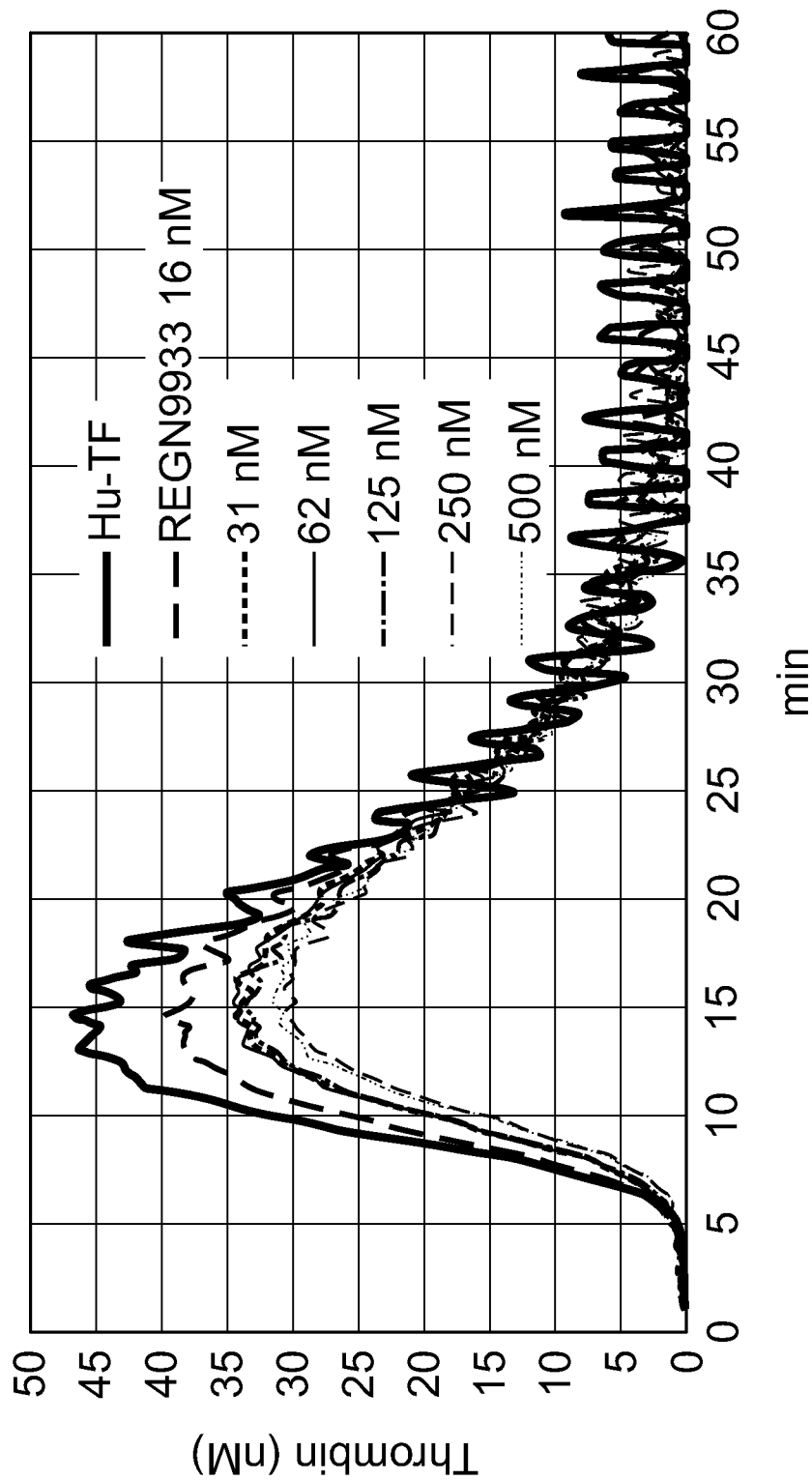
FIG. 6 depicts a line graph showing thrombin activity as a function of concentration of subject antibody (REGN9933) that binds FXI A2 over time.
Figure 7:
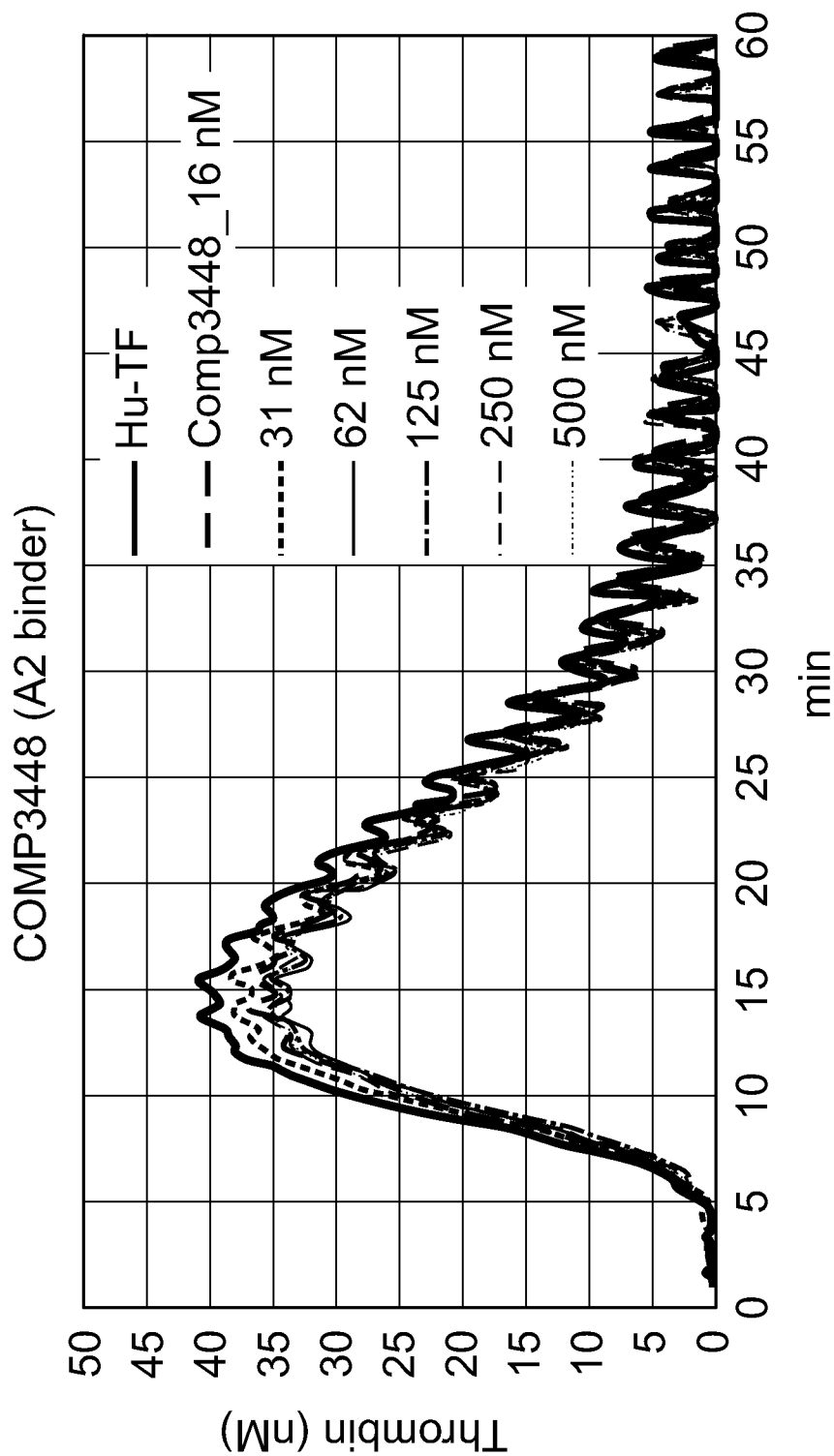
FIG. 7 depicts a line graph showing thrombin activity as a function of concentration of comparator antibody (COMP3448) that binds FXI A2 over time.

Thrombin generation triggered by Tissue Factor was not affected by the control isotype mAb (FIG. 5). The subject anti-FXI/FXIa mAb REGN9933 had a slight to mild inhibitory effect on thrombin generation triggered by Tissue Factor (FIG. 6). Comp mAb COMP3448 had the least effect on thrombin generation triggered by Tissue Factor (FIG. 7).

The concentrations of test article required to extend the lag time by two-fold, reduce the thrombin peak and total amount of thrombin generation by half when coagulation is activated by ellagic acid or Tissue Factor are summarized in Table 9.

TABLE 9

Concentration of drug required to delay and reduce thrombin generation

| | Intrinsic Pathway Activation with Ellagic Acid | | | Extrinsic Pathway Activation with Tissue Factor | | |
|---|---|---|---|---|---|---|
| | ↑ lag time by 2x | ↓ endogenous thrombin potential by ½ | ↓ thrombin peak by ½ | ↑ lag time by 2x | ↓ endogenous thrombin potential by ½ | ↓ thrombin peak by ½ |
| Control mAb | — | — | — | — | — | — |
| Subject anti-FXI mAb REGN9933 | 31 nM | 31 nM | 31 nM | — | — | — |
| Comp mAb COMP3448 | 31 nM | 31 nM | 31 nM | — | — | — |

(—) = no effect on thrombin generation with a dose up to 500 nM

Example 8: Pharmacokinetic Study of Subject Anti-FXI Antibody Drug Substance in Cynomolgus Monkeys The objective of this study was to determine the intravenous single-dose pharmacodynamic/pharmacokinetic (PK/PD) parameters of anti-FXI monoclonal antibodies (mAbs) in cynomolgus monkeys over a period of 8 weeks.

Female cynomolgus monkeys (n=39) of 2-4 years of age weighing 2-4 kg were acclimated to laboratory housing for at least 2 weeks prior to initiation of mAb dosing. Animals were assigned to a dosing group based on established social groups where a stratified randomization schemed was used to incorporate body weight from one animal from each social unit to assign animals to study groups (Table 8). Animals were housed under standard conditions (Temperatures of 18° C. to 29° C.; relative humidity of 30% to 70%, respectively) and a 12 hour light/12 hour dark cycle was maintained. Food (PMI LABDIET FIBER-PLUS Monkey Diet 5049 biscuits, LabDiet, St. Louis, MO) was provided twice daily and water was provided ad libitum.

TABLE 10

Summary of Doses and Dose Groups

| Group No. | Test or Control Article | Dose Level (mg/kg) | Number of female animals |
|---|---|---|---|
| 1 | Saline | 0 | 3 |
| 2 | Comp mAb | 1 | 3 |
| 3 | COMP3448 | 3 | 3 |
| 4 | | 10 | 3 |
| 5 | REGN9933 | 1 | 3 |
| 6 | | 3 | 3 |
| 7 | | 10 | 3 |

The control group (Group 1) was administered a vehicle (10 mM histidine, pH 6.0) intravenously at a volume of 2 mL/kg. Groups 2-7 were administered the appropriate mAb (subject and comparator) intravenously at 1, 3 or 10 mg/kg. The dose volume of 2 mL/kg for each animal was based on the most recent body weight measurement. Blood samples were collected (venous draw) before and multiple times over the 8-week study period. The blood was processed for serum to measure the drug levels and for plasma to measure both the target levels and coagulation activity.

Drug levels were measured in serum using an Enzyme-linked Immunosorbent Assay (ELISA) with a mouse anti-human IgG Fc as the capture mAb and a biotinylated anti-human Ig kappa light chain specific as the detection mAb. A NeutrAvidin conjugated with horseradish peroxidase (NeutrAvidin-HRP) was used to convert a luminol-based substrate into a signal proportional to the concentration of the total FXI mAb concentration.

The target (FXI) levels were measured in plasmas using the Affinity Biologicals Factor XI ELISA kit (FXI-AG) (Ancaster, ON), which crosses to monkey FXI. The manufacturer's protocol was followed for determining monkey FXI concentrations.

The coagulation activity of plasma was determined in functional assays that measured clotting time and thrombin generation. Clotting time was determined using the Diagnostica Stago START 4 Hemostasis Analyzer (Diagnostica Stago, Parsippany, NJ) to measure the activated partial thromboplastin time (aPTT) that measures clotting activated by an intrinsic pathway activator (ellagic acid) and Prothrombin Time (PT) that measures clotting activated by an extrinsic pathway activator (tissue factor). The times to clotting were reported as fold change to baseline. Thrombin generation was measured on a Stago Diagnostica Calibrated Automated Thrombogram (CAT) (Diagnostica Stago, Parsippany, NJ). The thrombin generation assay (TGA) was conducted with the intrinsic pathway activator ellagic acid (EA) or the extrinsic pathway activator tissue factor (TF). Data for TGA are reported as percentage change from baseline for the following parameters: Lag time, peak thrombin concentration and total thrombin concentration.

Results Summary and Conclusions:

The pharmacokinetic (PK) parameters were estimated using non-compartmental analysis and population compartmental analysis. The mAb concentration-time profiles following intravenous bolus were characterized by an initial brief distribution phase followed by a linear beta elimination phase and a terminal target-mediated elimination phase (Tables 11 and 12). Dose-proportional increases in mAb $C_{max}$ were observed with intravenous administration (Table 13), and dose-normalized $C_{max}$ ($C_{max}$/Dose) were found to be comparable across mAb dosing groups. Drug exposure ($AUC_{inf}$) when normalized to dose ($AUC_{inf}$/Dose) was found to increase at higher doses, indicating a greater than dose-proportional increase in exposure across groups, which would be consistent with non-linear kinetics for the mAb. These observations are consistent with parallel linear and non-linear target-mediated clearance (TMC), in which the observed decrease in clearance is a function of increasing dose. The target (FXI) in plasma was increased approximately 2- to 3-fold from baseline in all animals except those receiving comp mAb COMP3448 (an A2 binder) (Tables 14 and 15). Higher doses of the mAb did not exhibit a dose dependent retention of target FXI concentrations.

The inhibitory activities of the anti-FXI mAb (subject and comparator) were assessed with functional assays measuring plasma clotting time or thrombin generation. At each time point, an aliquot of the plasma was used to determine clotting time as assessed by activated partial thromboplastin time (aPTT) and prothrombin time (PT) assays that measures clotting activity of the intrinsic and extrinsic coagulation activity, respectively. Data are shown as clotting time relative to baseline clotting time for aPTT (Tables 16 and 17) and for PT (Tables 18 and 19). The comp mAb and the subject anti-FXI mAb showed similar 2-fold prolongation (i.e., inhibitory effect) on aPTT clotting time. The change from baseline of the PT clotting times were not affected with any mAbs tested or with increasing doses of any mAbs.

Coagulation activity was also assessed by measuring the profile of thrombin generation when activated by an intrinsic pathway activator (ellagic acid) or by an extrinsic pathway activator (tissue factor). One measured parameter from the thrombin generation curve was lag time, which assesses time required to generate thrombin after the activator is added to plasma. Data were expressed a fold change from baseline lag time value. The 1 mg/kg dose of mAb extended lag time approximately by 2-fold for about 7 days in plasmas activated with ellagic acid (Tables 20 and 21). Lag time was extended ~3-to-4 fold that of baseline time for up to about 3 weeks for doses of 3 and 10 mg/kg for the mAbs when activated with ellagic acid. The lag time was not extended when tissue factor was used as the activator of coagulation (Tables 22 and 23).

The second parameter measured in the thrombin generation assay was peak thrombin, which assesses the concentration when generation of thrombin peaks. Data were expressed as percentage of baseline thrombin peak. The mAbs were able to significantly inhibit thrombin peak concentrations (when induced by ellagic acid) to about 5-15% of baseline at the three concentrations of mAb used; however, the effect was found to be short-lived (~5 days) with the 1 mg/kg dose (Tables 24 and 25). The 3 mg/kg reduced for up to 2 weeks while the 10 mg/kg mAb dose for about 4 weeks. The effect of mAb on peak thrombin when tissue factor was used as the activator was variable as it increased and decreased peak thrombin concentrations by 50% (Tables 26 and 27).

The third parameter measured in the thrombin generation assay was endogenous thrombin potential, which assesses total concentration of thrombin generated during the activity. Data were expressed as percentage of baseline total thrombin generation. The mAbs showed a similar effect on inhibition of total thrombin generation as they did with peak thrombin inhibition when ellagic acid was used to activate coagulation (Tables 28 and 29). Similarly, the results were variable when tissue factor was used at the activator (Tables 30 and 31).

TABLE 11

Measured plasma concentration of comp mAb COMP3448

|  | 1 mg/kg | | 3 mg/kg | | 10 mg/kg | |
|---|---|---|---|---|---|---|
|  | Conc (ug/ml) | SEM | Conc (ug/ml) | SEM | Conc (ug/ml) | SEM |
| 5 min | 30.37 | 1.25 | 97.93 | 10.08 | 302.33 | 9.70 |
| 6 hr | 26.17 | 1.59 | 80.53 | 5.80 | 262.33 | 15.90 |
| 1 d | 19.57 | 0.03 | 59.33 | 3.07 | 187.00 | 14.57 |
| 2 d | 13.97 | 0.34 | 49.03 | 2.92 | 152.67 | 13.02 |
| 3 d | 11.13 | 0.29 | 40.57 | 2.39 | 137.33 | 18.98 |
| 5 d | 6.06 | 0.76 | 34.27 | 0.67 | 116.03 | 11.24 |
| 7 d | 3.80 | 0.51 | 29.43 | 1.43 | 102.53 | 13.58 |
| 10 d | 1.98 | 0.31 | 24.30 | 1.90 | 89.00 | 9.53 |
| 14 d | 0.86 | 0.19 | 15.43 | 1.83 | 75.37 | 7.70 |
| 22 d | 0.20 | 0.06 | 4.14 | 0.47 | 50.90 | 5.52 |
| 29 d | 0.10 | 0.00 | 0.75 | 0.22 | 35.40 | 6.20 |
| 36 d | BLQ | BLQ | 0.29 | 0.04 | 22.03 | 5.79 |
| 43 d | BLQ | BLQ | 0.12 | 0.02 | 10.95 | 5.53 |
| 50 d | BLQ | BLQ | 0.56 | 0.00 | 5.63 | 4.24 |
| 57 d | BLQ | BLQ | BLQ | BLQ | 4.10 | 3.30 |

BLQ = Below Limit of Quantification

TABLE 12

Measured plasma concentration of subject anti-FXI mAb REGN9933

|  | 1 mg/kg | | 3 mg/kg | | 10 mg/kg | |
|---|---|---|---|---|---|---|
|  | Conc (ug/ml) | SEM | Conc (ug/ml) | SEM | Conc (ug/ml) | SEM |
| 5 min | 27.47 | 0.59 | 81.10 | 5.75 | 284.33 | 4.18 |
| 6 hr | 21.73 | 0.94 | 64.17 | 5.40 | 237.33 | 7.33 |
| 1 d | 15.57 | 0.59 | 48.97 | 4.54 | 180.67 | 2.03 |
| 2 d | 11.77 | 0.41 | 40.67 | 2.96 | 155.67 | 3.28 |
| 3 d | 9.60 | 0.36 | 34.90 | 2.80 | 137.00 | 1.00 |
| 5 d | 6.58 | 0.42 | 27.57 | 2.34 | 116.00 | 2.52 |
| 7 d | 4.83 | 0.29 | 24.63 | 2.98 | 102.70 | 6.71 |
| 10 d | 3.13 | 0.26 | 18.80 | 3.55 | 89.80 | 6.91 |
| 14 d | 2.10 | 0.25 | 13.21 | 3.35 | 76.90 | 7.61 |
| 22 d | 1.06 | 0.18 | 7.24 | 2.65 | 56.37 | 7.45 |
| 29 d | 0.60 | 0.11 | 3.61 | 1.42 | 37.80 | 6.85 |
| 36 d | 0.39 | 0.07 | 1.95 | 0.65 | 25.20 | 6.57 |
| 43 d | 0.28 | 0.05 | 1.35 | 0.45 | 14.93 | 5.76 |
| 50 d | 0.25 | 0.05 | 1.03 | 0.35 | 10.52 | 4.35 |
| 57 d | 0.20 | 0.04 | 0.77 | 0.26 | 6.72 | 2.77 |

TABLE 13

Calculated PK parameters for each mAb administered i.v.

| Parameter | Unit | COMP3448 1 mg/kg | | | | COMP3448 3 mg/kg | | | | COMP3448 10 mg/kg | | | |
|---|---|---|---|---|---|---|---|---|---|---|---|---|---|
|  |  | N | Mean | SD | CV % | N | Mean | SD | CV % | N | Mean | SD | CV % |
| $C_{max}$ | μg/mL | 3 | 30.4 | 2.16 | 7.10 | 3 | 97.9 | 17.5 | 17.8 | 3 | 302 | 16.8 | 5.56 |
| $C_{max}$/Dose | (μg/mL)/ (mg/kg) | 3 | 30.4 | 2.16 | 7.10 | 3 | 32.6 | 5.82 | 17.8 | 3 | 30.2 | 1.68 | 5.56 |
| $AUC_{inf}$ |  | 3 | 99.7 | 7.47 | 7.50 | 3 | 565 | 65.7 | 11.6 | 3 | 2840 | 655 | 23.0 |
| $AUC_{inf}$/Dose |  | 3 | 99.7 | 7.47 | 7.50 | 3 | 188 | 21.9 | 11.6 | 3 | 284 | 65.5 | 23.0 |
| $AUC_{inf\ \%\ Extrapolated}$ | % | 3 | 0.591 | 0.238 | 40.2 | 3 | 0.379 | 0.346 | 91.4 | 3 | 1.59 | 2.05 | 129 |

TABLE 13-continued

Calculated PK parameters for each mAb administered i.v.

| | | | | | | | | | | | | | |
|---|---|---|---|---|---|---|---|---|---|---|---|---|---|
| $t_{1/2}$ | day | 3 | 3.11 | 0.498 | 16.0 | 3 | 4.12 | 1.41 | 34.3 | 3 | 8.11 | 4.43 | 54.6 |
| CL | mL/day/kg | 3 | 10.1 | 0.789 | 7.84 | 3 | 5.36 | 0.612 | 11.4 | 3 | 3.65 | 0.847 | 23.2 |

| | | Subject mAb REGN9933 1 mg/kg | | | | Subject mAb REGN9933 3 mg/kg | | | | Subject mAb REGN9933 10 mg/kg | | | |
|---|---|---|---|---|---|---|---|---|---|---|---|---|---|
| Parameter | Unit | N | Mean | SD | CV % | N | Mean | SD | CV % | N | Mean | SD | CV % |
| $C_{max}$ | µg/mL | 3 | 27.5 | 1.02 | 3.72 | 3 | 81.1 | 9.96 | 12.3 | 3 | 284 | 7.23 | 2.54 |
| $C_{max}$/Dose | (µg/mL)/(mg/kg) | 3 | 27.5 | 1.02 | 3.72 | 3 | 27.0 | 3.32 | 12.3 | 3 | 28.4 | 0.723 | 2.54 |
| $AUC_{inf}$ | | 3 | 123 | 13.2 | 10.7 | 3 | 553 | 173 | 31.3 | 3 | 3070 | 674 | 21.9 |
| $AUC_{inf}$/Dose | | 3 | 123 | 13.2 | 10.7 | 3 | 184 | 57.7 | 31.3 | 3 | 307 | 67.4 | 21.9 |
| $AUC_{inf\ \%\ Extrapolated}$ | % | 3 | 2.19 | 0.688 | 31.5 | 3 | 1.73 | 0.828 | 47.8 | 3 | 3.92 | 2.98 | 76.1 |
| $t_{1/2}$ | day | 3 | 9.31 | 0.909 | 9.77 | 3 | 8.92 | 1.25 | 14.1 | 3 | 12.2 | 3.31 | 27.1 |
| CL | mL/day/kg | 3 | 8.16 | 0.831 | 10.2 | 3 | 5.81 | 1.85 | 31.8 | 3 | 3.36 | 0.736 | 21.9 |

$C_{max}$ = Maximal concentration;
$C_{max}$/Dose = Dose-normalized $C_{max}$;
$AUC_{inf}$ = Exposure;
$AUC_{inf}$/Dose = Dose-normalized exposure;
$AUC_{inf\ \%\ Extrapolated}$ = Extrapolated percentage of exposure;
$t_{1/2}$ = half-life and
CL = Clearance

TABLE 14

Measured plasma concentration of total monkey FXI in animals dosed with comp mAb COMP3448

| | 1 mg/kg | | 3 mg/kg | | 10 mg/kg | |
|---|---|---|---|---|---|---|
| | Conc (mg/ml) | SEM | Conc (mg/ml) | SEM | Conc (mg/ml) | SEM |
| 0 min | 2.13 | 0.53 | 2.17 | 0.11 | 1.46 | 0.18 |
| 5 min | 1.38 | 0.25 | 1.62 | 0.19 | 1.23 | 0.28 |
| 6 hr | 1.77 | 0.39 | 1.74 | 0.11 | 1.34 | 0.34 |
| 1 d | 2.36 | 0.44 | 2.44 | 0.10 | 1.44 | 0.27 |
| 2 d | 2.70 | 0.35 | 2.49 | 0.05 | 1.66 | 0.35 |
| 3 d | 2.74 | 0.38 | 2.70 | 0.15 | 1.79 | 0.33 |
| 5 d | 2.77 | 0.16 | 2.60 | 0.36 | 1.96 | 0.36 |
| 7 d | 2.72 | 0.36 | 2.48 | 0.26 | 1.78 | 0.33 |
| 10 d | 2.60 | 0.40 | 2.54 | 0.14 | 1.90 | 0.33 |
| 14 d | 2.41 | 0.51 | 2.59 | 0.15 | 1.86 | 0.12 |
| 22 d | 2.28 | 0.27 | 2.57 | 0.30 | 2.10 | 0.39 |
| 29 d | 2.41 | 0.55 | 2.65 | 0.31 | 2.14 | 0.44 |
| 36 d | 2.04 | 0.37 | 2.07 | 0.14 | 2.19 | 0.51 |
| 43 d | 2.08 | 0.31 | 2.02 | 0.24 | 2.28 | 0.60 |
| 50 d | 1.95 | 0.36 | 2.23 | 0.39 | 2.72 | 0.60 |
| 57 d | 2.30 | 0.71 | 2.10 | 0.36 | 2.32 | 0.43 |

TABLE 15

Measured plasma concentration of total monkey FXI in animals dosed with subject anti-FXI mAb REGN9933

| | 1 mg/kg | | 3 mg/kg | | 10 mg/kg | |
|---|---|---|---|---|---|---|
| | Conc (mg/ml) | SEM | Conc (mg/ml) | SEM | Conc (mg/ml) | SEM |
| 0 min | 3.75 | 0.21 | 2.52 | 0.66 | 2.70 | 0.34 |
| 5 min | 3.19 | 0.17 | 2.53 | 0.78 | 2.35 | 0.20 |
| 6 hr | 3.81 | 0.10 | 2.55 | 0.79 | 2.49 | 0.33 |
| 1 d | 4.24 | 0.16 | 3.65 | 0.86 | 3.22 | 0.24 |
| 2 d | 4.41 | 0.14 | 4.00 | 0.93 | 3.50 | 0.33 |
| 3 d | 4.40 | 0.07 | 4.12 | 1.16 | 4.05 | 0.35 |
| 5 d | 4.65 | 0.15 | 4.15 | 1.05 | 4.04 | 0.45 |
| 7 d | 4.67 | 0.10 | 4.22 | 1.27 | 3.80 | 0.64 |
| 10 d | 4.03 | 0.31 | 3.60 | 0.88 | 3.78 | 0.69 |
| 14 d | 4.24 | 0.21 | 3.86 | 0.95 | 4.41 | 0.67 |
| 22 d | 4.11 | 0.22 | 3.54 | 0.65 | 3.92 | 0.54 |
| 29 d | 4.19 | 0.21 | 4.15 | 0.60 | 4.74 | 0.85 |
| 36 d | 4.12 | 0.06 | 3.25 | 0.29 | 4.57 | 0.58 |
| 43 d | 4.19 | 0.35 | 2.98 | 0.43 | 4.63 | 0.53 |
| 50 d | 3.91 | 0.48 | 3.21 | 0.40 | 5.20 | 0.71 |
| 57 d | 3.65 | 0.25 | 2.97 | 0.15 | 5.15 | 1.32 |

TABLE 16

Measured fold change in aPTT in animals dosed with comp mAb COMP3448

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 2.02 | 0.07 | 1.95 | 0.02 | 2.36 | 0.06 |
| 6 hr | 1.81 | 0.06 | 2.00 | 0.08 | 2.15 | 0.16 |
| 1 d | 1.87 | 0.08 | 1.92 | 0.07 | 2.21 | 0.16 |
| 2 d | 1.75 | 0.11 | 1.81 | 0.10 | 2.23 | 0.13 |
| 3 d | 1.74 | 0.04 | 1.87 | 0.07 | 2.28 | 0.16 |
| 5 d | 1.55 | 0.11 | 1.88 | 0.04 | 2.25 | 0.18 |
| 7 d | 1.25 | 0.10 | 1.86 | 0.08 | 2.32 | 0.16 |
| 10 d | 1.11 | 0.06 | 1.88 | 0.07 | 2.30 | 0.15 |
| 14 d | 1.06 | 0.03 | 1.84 | 0.04 | 2.33 | 0.13 |
| 22 d | 1.10 | 0.05 | 1.31 | 0.07 | 2.26 | 0.07 |
| 29 d | 1.06 | 0.03 | 1.02 | 0.01 | 2.16 | 0.13 |
| 36 d | 1.07 | 0.04 | 1.00 | 0.04 | 2.19 | 0.17 |
| 43 d | 1.07 | 0.04 | 1.00 | 0.01 | 1.71 | 0.12 |
| 50 d | 1.05 | 0.04 | 1.02 | 0.01 | 1.41 | 0.26 |
| 57 d | 1.01 | 0.04 | 1.01 | 0.02 | 1.36 | 0.21 |

TABLE 17

Measured fold change in aPTT in animals dosed with subject anti-FXI mAb REGN9933

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 1.84 | 0.04 | 2.03 | 0.10 | 2.04 | 0.12 |
| 6 hr | 1.80 | 0.03 | 1.92 | 0.10 | 2.01 | 0.12 |
| 1 d | 1.75 | 0.04 | 1.89 | 0.10 | 1.93 | 0.12 |
| 2 d | 1.63 | 0.06 | 1.92 | 0.10 | 1.92 | 0.11 |
| 3 d | 1.60 | 0.04 | 1.87 | 0.10 | 1.89 | 0.10 |
| 5 d | 1.28 | 0.06 | 1.87 | 0.08 | 1.98 | 0.09 |
| 7 d | 1.08 | 0.08 | 1.97 | 0.12 | 2.00 | 0.12 |
| 10 d | 1.07 | 0.09 | 1.76 | 0.09 | 1.97 | 0.11 |
| 14 d | 1.04 | 0.04 | 1.56 | 0.18 | 1.93 | 0.14 |
| 22 d | 1.03 | 0.04 | 1.29 | 0.14 | 1.83 | 0.09 |
| 29 d | 1.02 | 0.03 | 1.08 | 0.04 | 1.83 | 0.09 |
| 36 d | 1.04 | 0.04 | 1.05 | 0.01 | 1.54 | 0.09 |
| 43 d | 1.04 | 0.02 | 1.05 | 0.03 | 1.33 | 0.18 |
| 50 d | 1.03 | 0.04 | 1.06 | 0.04 | 1.11 | 0.10 |
| 57 d | 1.01 | 0.02 | 1.07 | 0.03 | 1.00 | 0.03 |

TABLE 18

Measured fold change in PT in animals dosed with comp mAb COMP3448

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 0.95 | 0.08 | 1.01 | 0.02 | 1.07 | 0.01 |
| 6 hr | 0.93 | 0.09 | 1.03 | 0.01 | 1.03 | 0.04 |
| 1 d | 0.93 | 0.08 | 1.02 | 0.03 | 1.02 | 0.05 |
| 2 d | 0.92 | 0.08 | 0.99 | 0.03 | 1.03 | 0.06 |
| 3 d | 0.90 | 0.07 | 1.00 | 0.01 | 1.02 | 0.06 |
| 5 d | 0.91 | 0.07 | 0.98 | 0.02 | 1.03 | 0.04 |
| 7 d | 0.92 | 0.08 | 1.00 | 0.00 | 1.07 | 0.05 |
| 10 d | 0.96 | 0.07 | 1.01 | 0.01 | 1.12 | 0.06 |
| 14 d | 0.94 | 0.07 | 1.02 | 0.02 | 1.09 | 0.07 |
| 22 d | 0.95 | 0.09 | 1.01 | 0.03 | 1.12 | 0.04 |
| 29 d | 0.95 | 0.08 | 1.03 | 0.02 | 1.10 | 0.07 |
| 36 d | 0.93 | 0.07 | 1.08 | 0.02 | 1.07 | 0.03 |
| 43 d | 0.92 | 0.08 | 1.03 | 0.02 | 1.07 | 0.03 |
| 50 d | 0.92 | 0.08 | 1.06 | 0.02 | 1.04 | 0.03 |
| 57 d | 0.91 | 0.07 | 1.03 | 0.02 | 1.05 | 0.04 |

TABLE 19

Measured fold change in PT in animals dosed with subject anti-FXI mAb REGN9933

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 1.04 | 0.01 | 1.04 | 0.02 | 1.00 | 0.02 |
| 6 hr | 1.04 | 0.02 | 1.03 | 0.00 | 1.00 | 0.02 |
| 1 d | 1.05 | 0.03 | 1.01 | 0.02 | 0.98 | 0.01 |
| 2 d | 0.98 | 0.02 | 0.98 | 0.02 | 0.96 | 0.02 |
| 3 d | 0.99 | 0.02 | 0.99 | 0.02 | 0.94 | 0.01 |
| 5 d | 0.98 | 0.03 | 0.99 | 0.01 | 0.97 | 0.01 |
| 7 d | 1.08 | 0.03 | 1.21 | 0.10 | 1.02 | 0.04 |
| 10 d | 1.04 | 0.04 | 1.03 | 0.01 | 0.98 | 0.06 |
| 14 d | 1.04 | 0.03 | 1.02 | 0.01 | 0.97 | 0.05 |
| 22 d | 1.04 | 0.03 | 1.05 | 0.01 | 0.97 | 0.02 |
| 29 d | 1.03 | 0.02 | 1.10 | 0.02 | 0.99 | 0.03 |
| 36 d | 1.04 | 0.02 | 1.07 | 0.02 | 0.99 | 0.03 |
| 43 d | 1.05 | 0.02 | 1.04 | 0.01 | 1.00 | 0.03 |
| 50 d | 1.06 | 0.02 | 1.06 | 0.01 | 1.00 | 0.01 |
| 57 d | 1.02 | 0.00 | 1.11 | 0.15 | 0.98 | 0.02 |

TABLE 20

Measured fold change in lag time induced by ellagic acid in animals dosed with comp mAb COMP3448

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 1.93 | 0.52 | 2.07 | 0.74 | 2.60 | 0.53 |
| 6 hr | 2.00 | 0.20 | 2.50 | 0.38 | 3.00 | 1.10 |
| 1 d | 1.97 | 0.38 | 2.47 | 0.20 | 2.40 | 0.06 |
| 2 d | 1.70 | 1.00 | 2.60 | 0.00 | 2.97 | 0.82 |
| 3 d | 2.25 | 0.25 | 3.77 | 1.04 | 3.77 | 1.17 |
| 5 d | 1.83 | 0.35 | 2.93 | 0.41 | 2.73 | 0.43 |
| 7 d | 1.20 | 0.10 | 2.33 | 0.38 | 3.53 | 0.80 |
| 10 d | 1.00 | 0.15 | 2.23 | 0.48 | 3.37 | 0.62 |
| 14 d | 0.97 | 0.09 | 2.77 | 0.52 | 3.57 | 1.03 |
| 22 d | 0.87 | 0.09 | 1.60 | 0.17 | 2.63 | 0.84 |
| 29 d | 0.83 | 0.03 | 1.13 | 0.12 | 2.87 | 0.62 |
| 36 d | 0.87 | 0.07 | 0.93 | 0.12 | 3.10 | 0.75 |
| 43 d | 0.93 | 0.03 | 1.03 | 0.09 | 2.40 | 0.81 |
| 50 d | 0.90 | 0.06 | 1.00 | 0.00 | 1.80 | 0.85 |
| 57 d | 0.83 | 0.07 | 1.10 | 0.12 | 1.63 | 0.74 |

TABLE 21

Measured fold change in lag time induced by ellagic acid in animals dosed with subject anti-FXI mAb REGN9933

| | 1 mg/kg | | 3 mg/kg | | 10 mg/kg | |
|---|---|---|---|---|---|---|
| | Fold change | SEM | Fold change | SEM | Fold change | SEM |
| 0 min | 1.000 | 0.000 | 1.000 | 0.000 | 1.000 | 0.000 |
| 5 min | 2.400 | 0.361 | 3.067 | 0.498 | 3.100 | 0.300 |
| 6 hr | 2.700 | 0.656 | 2.367 | 0.348 | 3.400 | 0.200 |
| 1 d | 3.067 | 0.463 | 2.767 | 0.285 | 3.033 | 0.318 |
| 2 d | 2.600 | 0.000 | 2.967 | 0.033 | 3.067 | 0.067 |
| 3 d | 2.400 | 0.306 | 3.500 | 0.289 | 3.267 | 0.384 |
| 5 d | 1.467 | 0.167 | 3.533 | 0.176 | 4.300 | 0.737 |
| 7 d | 1.500 | 0.000 | 3.300 | 0.173 | 3.300 | 0.400 |
| 10 d | 1.333 | 0.145 | 2.767 | 0.448 | 2.700 | 0.346 |
| 14 d | 1.200 | 0.058 | 2.933 | 0.817 | 3.667 | 0.260 |
| 22 d | 1.050 | 0.050 | 1.967 | 0.581 | 2.733 | 0.491 |
| 29 d | 1.033 | 0.067 | 1.300 | 0.200 | 3.567 | 0.353 |
| 36 d | 0.967 | 0.088 | 1.067 | 0.219 | 2.100 | 0.200 |
| 43 d | 0.967 | 0.145 | 1.400 | 0.400 | 2.533 | 0.441 |
| 50 d | 1.067 | 0.067 | 1.267 | 0.291 | 2.300 | 0.569 |
| 57 d | 0.967 | 0.033 | 1.500 | 0.500 | 1.533 | 0.145 |

TABLE 22

Measured fold change in lag time induced by tissue factor in animals dosed with comp mAb COMP3448

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 0.93 | 0.03 | 0.93 | 0.07 | 0.93 | 0.07 |
| 6 hr | 0.90 | 0.00 | 0.97 | 0.03 | 1.00 | 0.00 |
| 1 d | 0.87 | 0.03 | 1.00 | 0.06 | 0.90 | 0.06 |
| 2 d | 0.90 | 0.10 | 1.00 | 0.00 | 0.87 | 0.03 |
| 3 d | 0.95 | 0.05 | 1.13 | 0.03 | 1.00 | 0.06 |
| 5 d | 0.97 | 0.07 | 1.07 | 0.09 | 1.03 | 0.03 |
| 7 d | 0.87 | 0.03 | 1.07 | 0.07 | 1.03 | 0.07 |
| 10 d | 0.97 | 0.03 | 0.93 | 0.03 | 1.00 | 0.06 |
| 14 d | 1.00 | 0.10 | 0.97 | 0.03 | 1.00 | 0.06 |
| 22 d | 0.87 | 0.09 | 1.03 | 0.03 | 1.03 | 0.07 |
| 29 d | 0.93 | 0.03 | 0.97 | 0.03 | 1.10 | 0.06 |
| 36 d | 1.00 | 0.06 | 0.97 | 0.03 | 1.07 | 0.03 |
| 43 d | 0.97 | 0.03 | 0.97 | 0.03 | 1.03 | 0.03 |
| 50 d | 0.97 | 0.03 | 0.97 | 0.03 | 1.03 | 0.03 |
| 57 d | 1.07 | 0.09 | 0.97 | 0.03 | 1.07 | 0.03 |

TABLE 23

Measured fold change in lag time induced by tissue factor in animals dosed with subject anti-FXI mAb REGN9933

| | 1 mg/kg | | 3 mg/kg | | 10 mg/kg | |
|---|---|---|---|---|---|---|
| | Fold change | SEM | Fold change | SEM | Fold change | SEM |
| 0 min | 1.00 | 0.00 | 1.00 | 0.00 | 1.00 | 0.00 |
| 5 min | 0.97 | 0.03 | 0.90 | 0.06 | 0.95 | 0.05 |
| 6 hr | 0.97 | 0.12 | 0.90 | 0.06 | 0.97 | 0.03 |
| 1 d | 0.93 | 0.07 | 0.83 | 0.03 | 0.87 | 0.03 |
| 2 d | 1.00 | 0.10 | 0.83 | 0.03 | 0.83 | 0.09 |
| 3 d | 0.93 | 0.07 | 0.90 | 0.06 | 1.00 | 0.10 |
| 5 d | 1.13 | 0.13 | 0.97 | 0.03 | 0.93 | 0.09 |
| 7 d | 0.93 | 0.09 | 0.93 | 0.03 | 0.90 | 0.06 |
| 10 d | 1.00 | 0.06 | 0.93 | 0.03 | 0.97 | 0.09 |
| 14 d | 1.03 | 0.03 | 0.90 | 0.00 | 1.00 | 0.10 |
| 22 d | 1.10 | 0.10 | 0.97 | 0.03 | 1.00 | 0.06 |
| 29 d | 1.03 | 0.03 | 0.93 | 0.07 | 0.97 | 0.03 |
| 36 d | 0.93 | 0.03 | 0.93 | 0.03 | 0.90 | 0.06 |
| 43 d | 0.93 | 0.03 | 1.00 | 0.10 | 1.03 | 0.07 |
| 50 d | 1.03 | 0.03 | 0.93 | 0.03 | 1.10 | 0.10 |
| 57 d | 0.97 | 0.03 | 1.00 | 0.10 | 1.03 | 0.07 |

TABLE 24

Measured percentage change in peak thrombin generation induced by ellagic acid in animals dosed with comp mAb COMP3448

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 37.33 | 15.86 | 36.00 | 19.14 | 28.67 | 9.21 |
| 6 hr | 19.50 | 3.50 | 14.33 | 1.45 | 26.00 | 12.00 |
| 1 d | 22.67 | 6.12 | 16.00 | 2.08 | 20.00 | 2.65 |
| 2 d | 47.00 | 30.00 | 13.00 | 0.00 | 20.67 | 7.31 |
| 3 d | 27.00 | 6.00 | 9.67 | 1.86 | 12.33 | 3.18 |
| 5 d | 30.67 | 3.84 | 10.67 | 0.88 | 22.33 | 5.46 |
| 7 d | 84.33 | 9.77 | 21.67 | 6.06 | 15.67 | 4.37 |
| 10 d | 110.00 | 15.52 | 19.00 | 1.53 | 16.67 | 2.73 |
| 14 d | 101.00 | 10.00 | 14.33 | 2.33 | 18.33 | 5.36 |
| 22 d | 108.00 | 7.57 | 57.67 | 17.80 | 40.00 | 15.31 |
| 29 d | 124.00 | 26.00 | 96.33 | 3.76 | 30.67 | 6.12 |
| 36 d | 108.67 | 13.69 | 97.33 | 8.01 | 26.67 | 9.61 |
| 43 d | 98.67 | 7.31 | 100.67 | 2.73 | 48.67 | 18.66 |
| 50 d | 102.33 | 4.48 | 99.00 | 5.51 | 80.67 | 31.76 |
| 57 d | 115.00 | 14.11 | 96.33 | 2.33 | 82.00 | 28.01 |

TABLE 25

Measured percentage change in peak thrombin generation induced by ellagic acid in animals dosed with subject anti-FXI mAb REGN9933

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 22.00 | 4.62 | 18.33 | 7.36 | 17.00 | 9.00 |
| 6 hr | 16.33 | 2.85 | 26.00 | 10.82 | 16.33 | 4.26 |
| 1 d | 14.00 | 1.53 | 12.33 | 1.20 | 15.67 | 2.96 |
| 2 d | 24.50 | 4.50 | 17.00 | 4.93 | 18.33 | 6.84 |
| 3 d | 20.00 | 2.52 | 12.00 | 2.08 | 17.67 | 3.18 |
| 5 d | 65.00 | 11.02 | 11.33 | 2.91 | 10.33 | 2.19 |
| 7 d | 70.00 | 0.00 | 14.67 | 5.21 | 16.67 | 4.10 |
| 10 d | 90.33 | 1.20 | 26.67 | 9.77 | 21.33 | 3.67 |
| 14 d | 91.33 | 3.38 | 32.00 | 22.07 | 16.33 | 2.40 |
| 22 d | 94.00 | 1.00 | 59.00 | 18.77 | 28.67 | 10.73 |
| 29 d | 106.33 | 6.17 | 91.00 | 7.37 | 22.67 | 7.80 |
| 36 d | 102.33 | 6.64 | 94.33 | 1.76 | 36.67 | 6.69 |
| 43 d | 103.67 | 7.88 | 97.00 | 2.00 | 44.00 | 11.06 |
| 50 d | 107.33 | 4.48 | 98.33 | 5.36 | 68.67 | 11.46 |
| 57 d | 101.67 | 13.64 | 96.50 | 0.50 | 81.33 | 7.45 |

TABLE 26

Measured percentage change in peak thrombin generation induced by tissue factor in animals dosed with comp mAb COMP3448

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 99.67 | 20.54 | 127.67 | 33.51 | 102.67 | 15.45 |
| 6 hr | 106.00 | 14.00 | 72.00 | 12.42 | 89.50 | 34.50 |
| 1 d | 83.33 | 17.63 | 89.00 | 15.95 | 82.00 | 4.51 |
| 2 d | 93.50 | 41.50 | 121.00 | 0.00 | 81.33 | 16.42 |
| 3 d | 103.50 | 24.50 | 63.67 | 3.18 | 71.00 | 14.57 |
| 5 d | 86.33 | 22.70 | 66.33 | 13.12 | 82.67 | 9.94 |
| 7 d | 114.00 | 27.79 | 108.00 | 42.02 | 64.00 | 12.01 |
| 10 d | 121.00 | 31.19 | 107.00 | 17.78 | 76.00 | 9.64 |
| 14 d | 113.00 | 29.57 | 88.33 | 8.97 | 86.33 | 18.22 |
| 22 d | 140.67 | 28.37 | 128.33 | 40.40 | 116.67 | 33.63 |
| 29 d | 137.67 | 30.68 | 121.00 | 2.52 | 104.33 | 23.75 |
| 36 d | 120.67 | 31.95 | 149.33 | 31.87 | 89.00 | 18.56 |
| 43 d | 100.67 | 23.95 | 123.00 | 5.51 | 99.67 | 22.05 |
| 50 d | 120.33 | 30.02 | 140.67 | 20.10 | 118.67 | 27.43 |
| 57 d | 141.00 | 38.30 | 126.33 | 5.67 | 103.00 | 17.79 |

TABLE 27

Measured percentage change in peak thrombin generation induced by tissue factor in animals dosed with subject anti-FXI mAb REGN9933

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 90.67 | 12.73 | 72.67 | 21.22 | 87.50 | 1.50 |
| 6 hr | 73.33 | 18.41 | 99.33 | 39.50 | 89.67 | 9.91 |
| 1 d | 67.67 | 9.56 | 69.33 | 2.91 | 105.33 | 10.67 |
| 2 d | 109.50 | 38.50 | 80.33 | 15.21 | 108.33 | 14.67 |
| 3 d | 73.33 | 6.57 | 67.33 | 4.67 | 110.33 | 22.52 |
| 5 d | 67.67 | 20.80 | 44.00 | 7.09 | 64.00 | 11.50 |
| 7 d | 119.67 | 24.74 | 57.67 | 12.47 | 103.67 | 17.42 |
| 10 d | 94.33 | 12.68 | 95.33 | 25.98 | 118.67 | 15.17 |
| 14 d | 125.00 | 11.15 | 78.00 | 22.74 | 113.00 | 23.69 |
| 22 d | 135.50 | 6.50 | 101.67 | 31.26 | 126.33 | 10.53 |
| 29 d | 155.67 | 11.10 | 125.33 | 13.92 | 120.00 | 23.86 |
| 36 d | 126.00 | 22.12 | 121.33 | 37.60 | 144.00 | 4.93 |
| 43 d | 123.50 | 6.98 | 135.50 | 38.50 | 99.67 | 3.18 |
| 50 d | 142.67 | 18.44 | 144.33 | 44.14 | 135.33 | 24.04 |
| 57 d | 143.33 | 10.49 | 112.00 | 38.00 | 130.67 | 17.15 |

TABLE 28

Measured percentage change in total thrombin generation induced by ellagic acid in animals dosed with comp mAb COMP3448

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 56.33 | 13.38 | 54.00 | 16.82 | 58.00 | 13.61 |
| 6 hr | 34.00 | 4.00 | 31.33 | 1.67 | 47.00 | 5.00 |
| 1 d | 39.33 | 8.41 | 33.00 | 4.04 | 46.67 | 9.96 |
| 2 d | 62.50 | 25.50 | 26.00 | 0.00 | 45.33 | 14.08 |
| 3 d | 47.00 | 10.00 | 21.00 | 3.79 | 32.00 | 5.69 |
| 5 d | 48.00 | 3.46 | 22.33 | 2.33 | 49.33 | 9.96 |
| 7 d | 94.67 | 9.53 | 40.00 | 9.85 | 36.33 | 5.78 |
| 10 d | 103.67 | 5.49 | 38.00 | 2.89 | 42.67 | 7.13 |
| 14 d | 93.67 | 3.71 | 30.67 | 6.17 | 43.67 | 9.94 |
| 22 d | 98.00 | 7.51 | 77.00 | 19.76 | 65.67 | 18.68 |
| 29 d | 104.67 | 13.72 | 94.67 | 5.21 | 58.67 | 1.20 |
| 36 d | 102.67 | 9.56 | 95.33 | 7.22 | 51.33 | 13.17 |
| 43 d | 92.67 | 6.12 | 98.33 | 4.37 | 70.00 | 17.62 |
| 50 d | 95.67 | 2.96 | 98.33 | 1.67 | 82.67 | 18.32 |
| 57 d | 106.33 | 14.44 | 98.67 | 4.98 | 90.67 | 11.33 |

TABLE 29

Measured percentage change in total thrombin generation induced by ellagic acid in animals dosed with subject anti-FXI mAb REGN9933

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 41.33 | 6.57 | 37.33 | 16.59 | 39.00 | 16.00 |
| 6 hr | 30.67 | 2.19 | 46.67 | 15.25 | 37.00 | 8.08 |
| 1 d | 28.33 | 2.40 | 29.33 | 6.49 | 36.67 | 7.06 |
| 2 d | 41.33 | 4.00 | 38.00 | 14.57 | 39.00 | 13.11 |
| 3 d | 36.67 | 5.36 | 27.33 | 6.89 | 41.33 | 8.11 |
| 5 d | 77.00 | 4.36 | 25.67 | 10.14 | 23.33 | 4.41 |
| 7 d | 83.00 | 0.00 | 33.33 | 14.88 | 38.67 | 5.33 |
| 10 d | 88.00 | 5.51 | 48.33 | 17.29 | 46.00 | 5.13 |
| 14 d | 88.67 | 3.53 | 44.33 | 20.04 | 40.33 | 5.55 |
| 22 d | 96.00 | 3.00 | 71.67 | 9.96 | 55.67 | 16.71 |
| 29 d | 99.33 | 3.33 | 90.33 | 3.53 | 44.00 | 10.82 |
| 36 d | 92.33 | 2.33 | 90.00 | 4.51 | 61.33 | 9.06 |
| 43 d | 95.00 | 5.51 | 89.00 | 1.00 | 71.00 | 12.66 |
| 50 d | 98.33 | 4.26 | 91.67 | 3.53 | 89.00 | 5.51 |
| 57 d | 92.00 | 7.55 | 90.50 | 3.50 | 93.67 | 3.67 |

TABLE 30

Measured percentage change in total thrombin generation induced by tissue factor in animals dosed with comp mAb COMP3448

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 97.33 | 12.33 | 117.67 | 18.11 | 106.67 | 10.35 |
| 6 hr | 116.00 | 4.00 | 83.33 | 10.65 | 92.00 | 16.00 |
| 1 d | 84.00 | 12.12 | 93.67 | 13.62 | 89.00 | 3.06 |
| 2 d | 86.00 | 22.00 | 123.00 | 0.00 | 94.00 | 9.87 |
| 3 d | 100.00 | 26.00 | 80.00 | 5.29 | 84.00 | 8.14 |
| 5 d | 86.67 | 16.18 | 79.33 | 15.93 | 89.33 | 4.98 |
| 7 d | 103.67 | 17.37 | 106.67 | 29.04 | 78.67 | 5.36 |
| 10 d | 121.67 | 31.21 | 114.67 | 13.72 | 91.33 | 6.64 |
| 14 d | 110.00 | 25.36 | 96.33 | 6.69 | 102.00 | 13.01 |
| 22 d | 120.33 | 17.29 | 118.67 | 27.76 | 109.00 | 18.45 |
| 29 d | 127.67 | 22.93 | 115.00 | 2.65 | 107.00 | 15.04 |
| 36 d | 113.33 | 22.93 | 131.00 | 16.04 | 99.33 | 10.91 |
| 43 d | 102.00 | 18.77 | 118.00 | 1.15 | 103.00 | 13.80 |
| 50 d | 116.00 | 19.08 | 132.33 | 14.50 | 114.67 | 14.90 |
| 57 d | 135.00 | 28.68 | 127.67 | 4.18 | 116.67 | 14.17 |

TABLE 31

Measured percentage change in total thrombin generation induced by tissue factor in animals dosed with subject anti-FXI mAb REGN9933

| | 1 mg/kg | | 3 mg/kg | | 10 mg/kg | |
|---|---|---|---|---|---|---|
| | % change | SEM | % change | SEM | % change | SEM |
| 0 min | 100.00 | 0.00 | 100.00 | 0.00 | 100.00 | 0.00 |
| 5 min | 106.67 | 10.49 | 79.33 | 17.42 | 97.00 | 5.00 |
| 6 hr | 86.67 | 12.72 | 101.67 | 28.26 | 97.67 | 6.94 |
| 1 d | 80.00 | 5.51 | 84.67 | 4.48 | 112.00 | 8.54 |
| 2 d | 115.00 | 33.00 | 90.33 | 14.68 | 107.33 | 11.26 |
| 3 d | 85.33 | 5.24 | 84.00 | 4.04 | 113.33 | 16.59 |
| 5 d | 74.33 | 15.86 | 54.67 | 9.35 | 71.00 | 9.50 |
| 7 d | 84.00 | 0.00 | 72.00 | 13.89 | 114.00 | 15.50 |
| 10 d | 108.67 | 15.06 | 102.33 | 23.33 | 128.67 | 18.50 |
| 14 d | 130.00 | 7.81 | 90.33 | 19.70 | 122.33 | 17.75 |
| 22 d | 135.00 | 11.00 | 102.67 | 24.54 | 123.33 | 4.10 |
| 29 d | 148.00 | 4.51 | 117.33 | 10.11 | 119.00 | 20.79 |
| 36 d | 120.00 | 14.42 | 117.33 | 28.01 | 126.33 | 1.67 |
| 43 d | 118.33 | 5.24 | 125.50 | 33.50 | 106.67 | 6.89 |
| 50 d | 148.67 | 11.17 | 128.67 | 29.63 | 132.67 | 21.50 |
| 57 d | 137.00 | 4.00 | 108.00 | 32.00 | 121.67 | 14.99 |

Example 9: Primary Pharmacodynamics 9.1: In Vitro Pharmacology

A series of studies were performed to evaluate efficacy and safety of REGN9933 using in vitro assays. The goals of the in vitro studies included: (a) Determination of REGN9933 binding affinity and specificity to FXI from human and non-human species and from human FXIa; (b) Characterization of REGN9933-mediated blockade of the intrinsic and extrinsic coagulation pathways in plasma from human and cynomolgus monkey donors; (c) Evaluation of subject mAb REGN9933-FXI and subject mAb REGN9933-FXIa immune complexes for binding to C1q; and (d) Evaluation of the potential risk for an IgG4P antibody, such as REGN9933, to induce peripheral blood mononuclear cells (PBMC) proliferation and cytokine release.

The binding interaction between REGN9933 and human, cynomolgus monkey, rabbit, and mouse FXI or human FXIa was assessed using surface plasmon resonance (SPR)-based assays. In these assays, REGN9933 bound with subnanomolar affinity to human FXI and FXIa and cynomolgus monkey FXI. REGN9933 also bound weakly to rabbit FXI but did not bind mouse FXI (Example 9.1.1).

The capacity of REGN9933 to block coagulation pathways in pooled plasma from either human or cynomolgus monkey donors was assessed in vitro using clotting assays and thrombin generation assays (TGAs). In these assays, REGN9933 exerted concentration-dependent effects on the intrinsic coagulation pathway in human pooled plasma and had subtle effects on the extrinsic pathway. REGN9933 also exerted concentration-dependent effects on the intrinsic, but not extrinsic, coagulation pathway in cynomolgus monkey pooled plasma (Example 9.1.2.1).

REGN9933 is unlikely to form immune complexes capable of binding C1q because it contains a hinge-stabilized, IgG4-derived heavy chain fragment crystallizable (Fc) constant domain (termed IgG4P), and IgG4 does not bind as well as IgG1 to C1q (Patel, 2015). Nevertheless, an enzyme immunosorbent assay (EIA) was performed to evaluate the potential for binding of REGN9933-FXI and REGN9933-FXIa complexes to C1q. In this assay, REGN9933-FXI and REGN9933-FXIa complexes did not demonstrate positive binding to C1q (Example 9.1.2.2).

Results from cell-based in vitro experiments demonstrate that IgG4P antibodies that do not specifically target immune cell-surface molecules, such as REGN9933, have a low potential to induce cytokine release or proliferation of PBMC (Example 9.1.3).

In Vitro Functional Characterization of Subject mAb
9.1.1: Determination of Kinetic and Equilibrium Binding Parameters for the Interaction of the Subject mAb Interaction with FXI from Human, Cynomolgus Monkey, Rabbit, and Mouse and FXIa from Human In this study, SPR technology was used to determine the binding affinity of REGN9933 for human FXI and FXIa proteins derived from plasma and for recombinant human, cynomolgus monkey, rabbit, and mouse FXI proteins produced with a C-terminal myc-myc-hexahistidine (mmH)-tag. Human FXI (E19-V625) shares 96%, 86% and 79% amino acid sequence identity with cynomolgus monkey, rabbit, and mouse FXI, respectively. At 25° C. and pH 7.4, varying concentrations of soluble FXI or FXIa proteins were injected over surface-captured REGN9933, followed by a dissociation phase. The kinetic binding parameters for human, cynomolgus monkey, and mouse proteins were determined using a 1:1 binding model with mass transport limitation; binding affinity for rabbit protein was determined using a 1:1 steady-state binding model.

In tests using plasma-derived human proteins, REGN9933 bound human FXI (hFXI) and FXIa (hFXIa) with equilibrium dissociation constants (KD) of 14.4 and 141 pM, respectively (data not shown).

In tests using generated proteins produced with mmH-tags, the subject anti-FXI mAb REGN9933 bound recombinant human (hFXI.mmH) and cynomolgus monkey (*Macaca fascicularis*) (MfFXI.mmH) FXI with KD values of 144 and 104 pM, respectively, and showed weak but detectable binding to recombinant rabbit FXI (rbFXI.mmH) with a KD value of 171 nM. The subject anti-FXI mAb REGN9933 did not show detectable binding to recombinant mouse FXI (mFXI.mmH) up to the highest concentration tested (50 nM) (data not shown).

9.1.2.1: In Vitro Evaluation of the Capacity of the Subject Anti-FXI Antibody Drug Substance to Block Coagulation Pathways in Pooled Human or Cynomolgus Monkey Plasma In this study, the capacity of REGN9933 to block coagulation pathways in pooled plasma from either human or cynomolgus monkey donors was assessed in vitro using clotting assays and TGAs. In these assays, coagulation was induced in plasma by either EA or TF to measure the effects of REGN9933 on the intrinsic or extrinsic coagulation pathways, respectively.

A summary of the results for the clotting assays and TGAs using human and cynomolgus monkey plasma are provided in Table 32.

TABLE 32

Summary of Subject Anti-FXI mAb REGN9933 Effects on the Intrinsic and Extrinsic Coagulation Pathways in Human and Cynomolgus Monkey Plasma

| | | Maximum Change Relative to Baseline (no-antibody control)[a] | | | |
|---|---|---|---|---|---|
| | | Human Plasma | | Monkey Plasma | |
| Assay | Parameter | Intrinsic Pathway (Induced w/EA) | Extrinsic Pathway (Induced w/TF) | Intrinsic Pathway (Induced w/EA) | Extrinsic Pathway (Induced w/TF)[b] |
| Clotting Assay | Fold Increase in Clotting Time (aPTT w/EA; PT w/TF) | 2.7 | 1.0 | 2.1 | 1.0 |
| TGA | Fold Increase in Lag Time | 4.9 | 1.0 | 2.2 | 0.9 |
| | % Peak Thrombin | 8 | 86 | 43 | 107 |
| | % ETP | 28 | 89 | 66 | 111 |

Figure 8B:
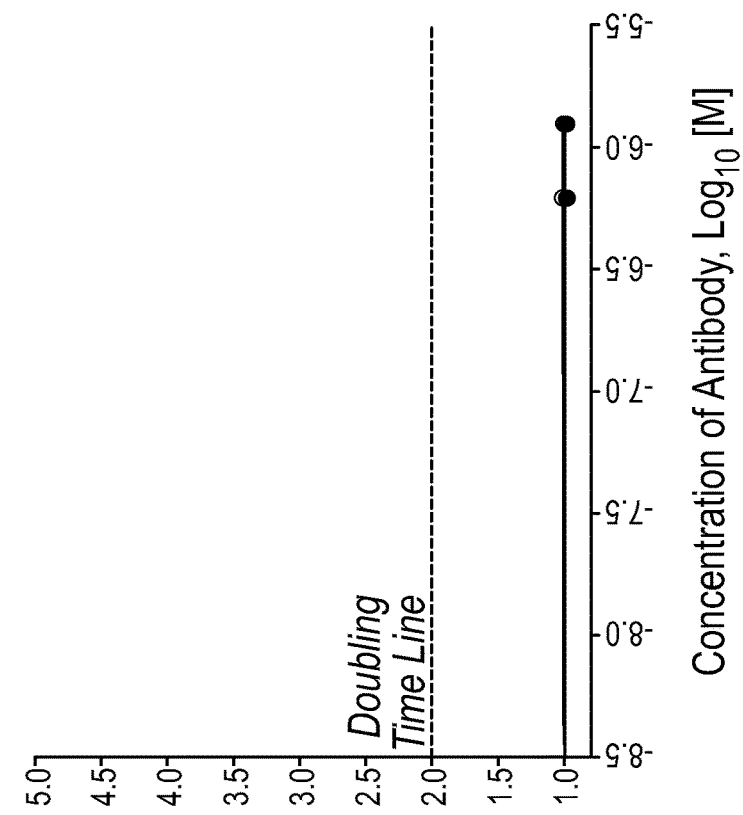
FIG. 8B depicts a line graph showing fold change in prothrombin time (PT) as a function of log concentration of antibody. In the PT clotting assay, human donor plasma was incubated with either REGN9933 or an IgG4P isotype control at 600 nM and 1200 nM followed by the addition of tissue factor (TF), a specific activator of the extrinsic coagulation pathway.
Figure 8A:
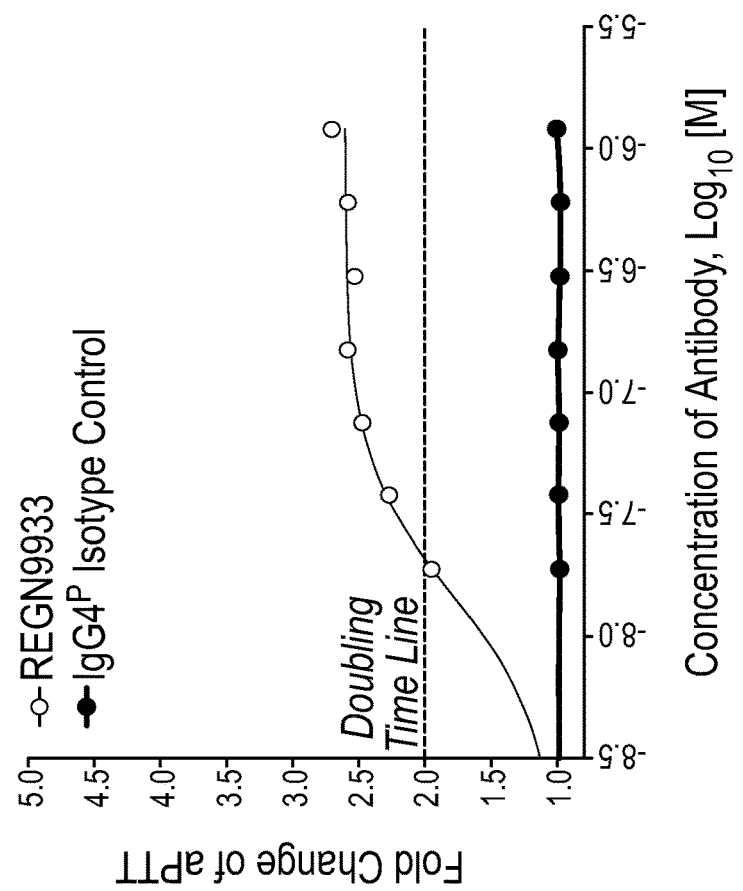
FIG. 8A depicts a line graph showing fold change in activated partial thromboplastin time (aPTT) as a function of log concentration of antibody. The dark shade depicts an isotype control. The light shade depicts the subject antibody, REGN9933, that binds FXI A2. In the aPTT clotting assay, human donor plasma was incubated with 2-fold serial dilutions of either REGN9933 or an IgG4P isotype control 19 nM to 1200 nM followed by the addition of ellagic acid (EA), a specific activator of the intrinsic coagulation pathway.

[a]Maximum change across the antibody concentrations tested (Clotting assays: 19 nM to 1.2 µM; TGAs: 16 nM to 500 nM)
[b]Concentration-dependent changes were not observed in either the clotting assays or the TGAs.
Abbreviations: aPTT, activated partial thromboplastin time; EA, ellagic acid; ETP, endogenous thrombin potential; PT, prothrombin time; TF, tissue factor; TGA, thrombin generation assay In clotting assays, the subject anti-FXI mAb REGN9933 increased aPTT relative to baseline (no antibody) in a concentration-dependent manner; increases of up to 2.7- and 2.1-fold in human (FIG. 8A) and cynomolgus monkey (data not shown) plasma, respectively, were observed at the range of antibody concentrations tested (19 nM to 1.2 µM). The doubling of aPTT relative to baseline was estimated to occur at 25 nM and 1.1 µM in human and cynomolgus monkey plasma, respectively. No change in PT relative to baseline was observed in either human or cynomolgus monkey plasma at the maximum antibody concentration tested (1.2 µM) (FIG. 8B).

Figure 9A:
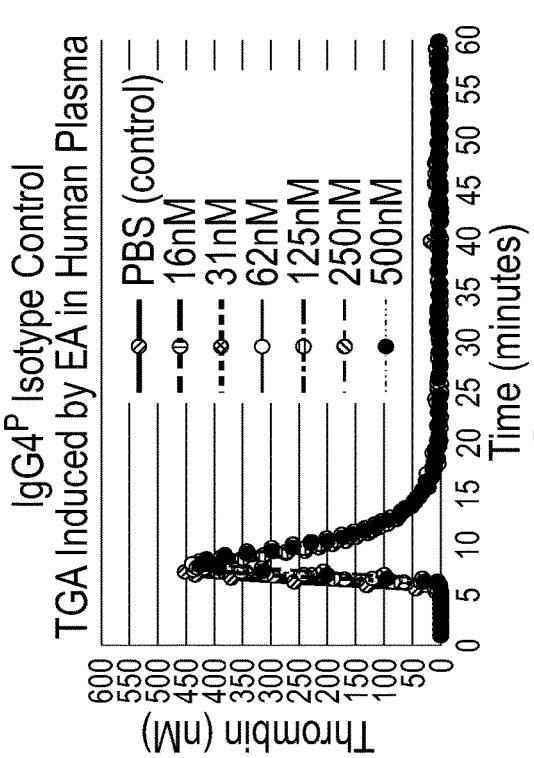
FIG. 9A depicts a line graph showing ellagic acid (EA) mediated thrombin activity as a function of concentration of subject antibody that binds FXI A2 over time.
Figure 9B:
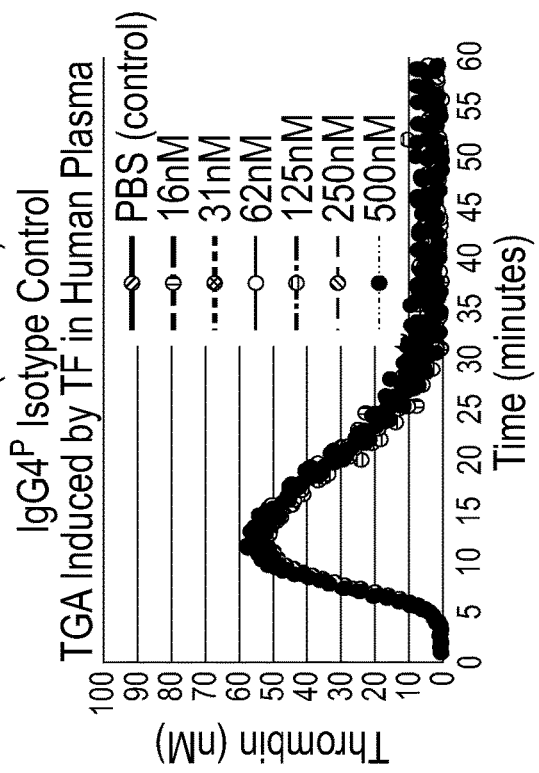
FIG. 9B depicts a line graph showing EA mediated thrombin activity as a function of concentration of isotype control antibody over time.
Figure 9C:
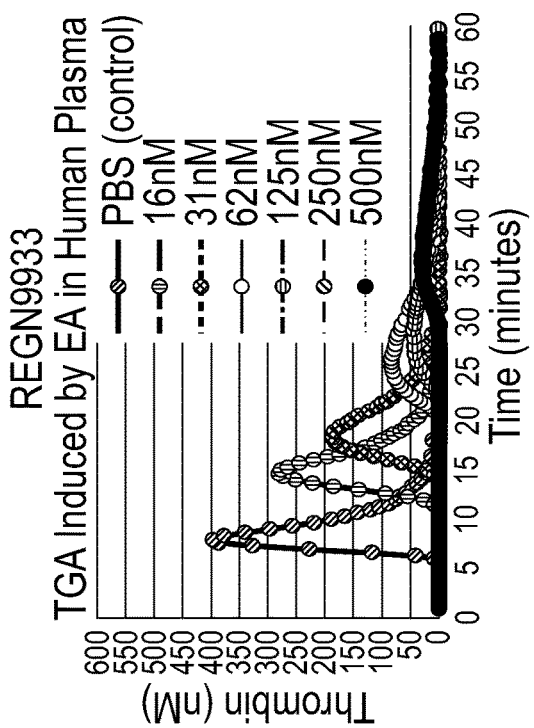
FIG. 9C depicts a line graph showing tissue factor (TF) mediated thrombin activity as a function of concentration of subject antibody, REGN9933, that binds FXI A2 over time.
Figure 9D:
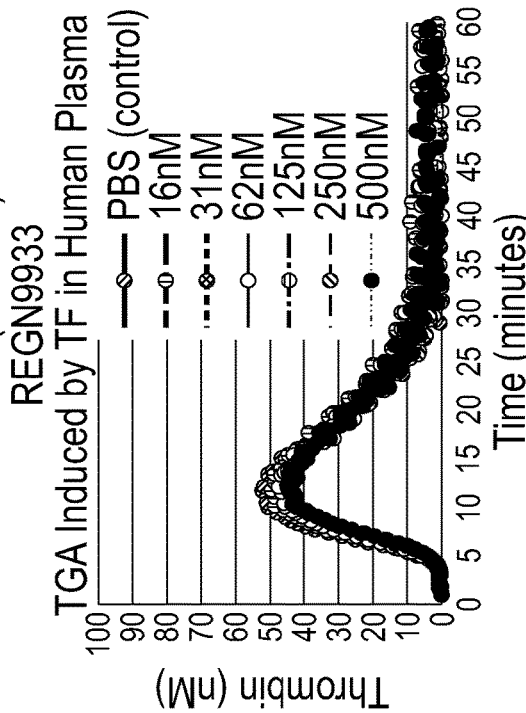
FIG. 9D depicts a line graph showing TF mediated thrombin activity as a function of concentration of isotype control antibody over time. Human donor plasma was incubated with 2-fold serial dilutions of either the subject mAb or an IgG4P isotype control 16 nM to 500 nM followed by the addition of (FIGS. 9A and 9B) ellagic acid (EA), a specific activator of the intrinsic coagulation pathway or (FIGS. 9B and 9C) tissue factor (TF), a specific activator of the extrinsic coagulation pathway. The measured real-time thrombin concentration values were plotted against time to yield a thrombogram profile for each antibody concentration tested as well as a no-antibody control (i.e., PBS).

In TGAs where thrombin generation was induced by EA via the intrinsic pathway in human plasma, the subject anti-FXI mAb REGN9933 increased the lag time for thrombin generation up to 4.9-fold relative to baseline (no antibody), reduced peak thrombin levels down to 8% of baseline, and reduced endogenous thrombin potential down to 28% of baseline (FIGS. 9A and 9B). The subject anti-FXI mAb REGN9933 exerted these effects in a concentration-dependent manner with maximal effects achieved at concentrations of ≥250 nM (FIG. 9A). When thrombin generation was induced by TF via the extrinsic pathway, the subject anti-FXI mAb REGN9933 slightly reduced peak thrombin levels down to 86% of baseline and reduced endogenous thrombin potential down to 89% of baseline (FIGS. 9C and 9D). The subject anti-FXI mAb REGN9933 exerted these effects in a concentration-dependent manner with maximal effects achieved at concentrations of ≥125 nM (FIG. 9C). No concentration-dependent increases in lag time for thrombin generation were observed with the subject anti-FXI mAb REGN9933 up to the maximum antibody concentration tested (500 nM) (FIG. 9C).

In TGAs where thrombin generation was induced by EA via the intrinsic pathway in cynomolgus monkey plasma, the subject anti-FXI mAb REGN9933 increased the lag time for thrombin generation up to 2.2-fold relative to baseline (no antibody), reduced peak thrombin levels down to 43% of baseline, and reduced endogenous thrombin potential down to 66% of baseline (data not shown). The subject anti-FXI mAb REGN9933 exerted these effects in a concentration-dependent manner with maximal effects achieved at concentrations of ≥62 nM. When thrombin generation was induced by TF via the extrinsic pathway, no concentration-dependent increases in lag time for thrombin generation or decreases in peak thrombin or endogenous thrombin potential were observed with the subject anti-FXI mAb REGN9933 up to the maximum antibody concentration tested (500 nM) (data not shown).

9.1.2.2: Evaluation of the Subject mAb REGN9933-FXI and—FXIa Immune Complexes for Binding to C1q.

Circulating immune complexes (CIC) are formed by multimerization of antibody with soluble antigen. Deposition of CIC within tissues and consequent inflammatory responses can lead to tissue damage at the site of deposition. Large immune complexes can also activate complement component C1q in serum (Rojko, 2014). REGN9933 is unlikely to form immune complexes capable of binding C1q because it contains a hinge-stabilized, IgG4-derived heavy chain Fc constant domain (termed IgG4$^P$), and IgG4 does not bind as well as IgG1 to C1q (Patel, 2015). Nevertheless, an EIA was performed to evaluate the potential for binding of the subject mAb-FXI and the subject mAb-FXIa complexes to C1q.

In this study, REGN9933 was incubated with human FXI or FXIa protein and added to plate-adsorbed C1q, followed by detection using anti-human IgG.

The subject mAb REGN9933-FXI and the subject mAb REGN9933-FXIa complexes did not demonstrate levels of binding considered positive per the assay kit's specifications (data not shown). In contrast, C1q binding was detected for a positive control complex, heat-aggregated human gamma globulin (HAGG).

9.1.3: In Vitro Characterization of Proliferation and Cytokine Release Following Treatment of Human Peripheral Blood Mononuclear Cells with a Non-Immune-Cell-Surface-Binding IgG4$^P$ Isotype Control Antibody The subject anti-FXI mAb REGN9933 is an IgG4$^P$ antibody that does not target immune cell-surface molecules. The ability of such non-binding IgG4$^P$ induce cytokine release or proliferation in human PBMC was assessed using the IgG4$^P$ isotype control antibody [REGN1945].

The IgG4$^P$ isotype control antibody [REGN1945] did not induce PBMC cytokine release or proliferation in an in-house study (data not shown) that was performed in accordance with established methods that detect PBMC proliferation and cytokine release induced by a superagonist anti-CD28 antibody (TeGenero TGN1412) (Findlay, 2010) (Vessillier, 2015). In this assay, the accumulation of IFN-γ, IL-2, TNF-α, IL-10, IL-6, IL-13, IL-4, and IL-12p70 was evaluated following incubation of PBMC with the test antibody. An IgG4$^P$ anti-CD28 superagonist antibody [REGN2329] with primary sequence identical to TGN1412 (with the exception of a S228P substitution), and a stimulatory anti-CD3 antibody (OKT3) served as positive controls. The IgG4$^P$ isotype control antibody [REGN1945], at concentrations ranging from 0.4 to 10 µg/mL, had no effect on PBMC proliferation (data not shown) or cytokine release (data not shown) under any test condition. In contrast, the anti-CD28 positive control antibody mediated significant proliferation of PBMC and significant cytokine release, while the anti-CD3 positive control antibody mediated significant cytokine release.

In summary, an IgG4$^P$ antibody that does not specifically target immune cell-surface molecules did not induce cytokine release from or proliferation of PBMC in standard in vitro assays. This study indicates that IgG4$^P$ antibodies that do not specifically target immune cell-surface molecules have low potential to induce cytokine release syndrome in humans.

9.1.4: Discussion

The subject m-Ab REGN9933 is a human IgG4-based mAb that binds FXI/FXIa and selectively inhibits the intrinsic coagulation pathway with minor effects on the extrinsic coagulation pathway in human plasma. The subject m-Ab REGN9933 is being developed for the prevention and treatment of thromboembolic diseases. A series of nonclinical studies were performed to evaluate efficacy and safety of the subject m-Ab REGN9933 using in vitro assays and in vivo models.

SPR studies showed that the subject m-Ab REGN9933 bound specifically to human FXI and FXIa as well as to cynomolgus monkey FXI with KD values in the picomolar range. The subject m-Ab REGN9933 also bound weakly to rabbit FXI with a high nanomolar KD value, whereas no binding to mouse FXI was detected. In vitro clotting time assays and TGAs using pooled plasma from human or cynomolgus monkey donors showed that the subject m-Ab REGN9933 blocked intrinsic coagulation pathway activity with a concentration-dependent effect on duration, but not magnitude. Subtle effects on extrinsic coagulation pathway activity in human plasma and no effects on extrinsic coagulation pathway activity in cynomolgus monkey plasma were observed. Together, these in vitro binding and activity studies demonstrated that the subject m-Ab REGN9933 is capable of binding FXI and blocking intrinsic coagulation pathway activity in human and monkey plasma, thereby supporting the use of the cynomolgus monkey as a relevant species for pharmacology and/or toxicology studies with the subject m-Ab REGN9933.

In an in vitro EIA, subject m-Ab REGN9933-FXI and subject m-Ab REGN9933-FXIa complexes did not demonstrate positive levels of binding to C1q, suggesting that the subject m-Ab REGN9933 has a low potential to induce immune complex-mediated inflammatory responses.

9.2: In Vivo Pharmacology

Subject m-Ab REGN9933-mediated blockade of the coagulation pathway in cynomolgus monkeys was assessed in a pilot PK/PD study evaluating a single IV dose of 1, 3, or 10 mg/kg of the subject m-Ab REGN9933 (Example 9.2.1) and a study evaluating a single dose of 0.5, 5, or 30 mg/kg the subject m-Ab REGN9933 via IV route or 30 mg/kg of the subject m-Ab REGN9933 via SC route (Example 9.2.2).

REGN9933-mediated blockade of the coagulation pathway was assessed in clotting assays and TGAs using plasma from cynomolgus monkeys that received a single IV dose of 1, 3, or 10 mg/kg of the subject m-Ab REGN9933 (Example 9.2.1) and in TGAs using plasma from cynomolgus monkeys that received a single dose of 0.5, 5, or 30 mg/kg of the subject m-Ab REGN9933 via intravenous (IV) route or 30 mg/kg of the subject m-Ab REGN9933 via subcutaneous (SC) route (Example 9.2.2). In the clotting assays performed in each of the aforementioned studies, REGN9933 exerted PD effects on the intrinsic coagulation pathway (i.e., prolonged activated partial thromboplastin time [aPTT] relative to baseline) with no effects on the extrinsic coagulation pathway (i.e., no effect on prothrombin time [PT] relative to baseline). In TGAs performed, the subject m-Ab REGN9933 exerted PD effects on the intrinsic coagulation pathway (i.e., prolonged lag time of thrombin generation, reduced peak thrombin levels, and reduced endogenous thrombin potential induced by ellagic acid [EA] relative to baseline) with minimal effects on the extrinsic coagulation pathway (i.e., no effect on lag time of thrombin generation and subtly reduced peak thrombin levels and endogenous thrombin potential induced by tissue factor [TF] relative to baseline). In both studies, the duration of the effects on the intrinsic coagulation pathway (observed in the clotting assays and TGAs), was dose-dependent whereas the subtle effects on the extrinsic coagulation pathway (observed in the TGAs) were not dose-dependent. The effects on the intrinsic coagulation pathway were likely driven by increased the subject m-Ab REGN9933 concentrations rather than reduced concentrations of FXI.

9.2.1: Ex Vivo Assessment of Single Doses of 1, 3, or 10 mg/kg the Subject mAb IV on Coagulation Pathway Activity in Cynomolgus Monkeys (R3448 PK 19085)

Characterization of the subject m-Ab REGN9933-mediated blockade of the coagulation pathway in cynomolgus monkeys was assessed as part of a single-dose PK study (data not shown). Female cynomolgus monkeys were administered a single IV slow bolus injection of vehicle (control) or the subject m-Ab REGN9933 at doses of 1, 3, or 10 mg/kg (n=3 per group) and monitored for 8 weeks post dose. Blood samples were collected from all animals pre dose and at 5 minutes, 6 hours, Day 2, Day 3, Day 4, Day 6, Day 8, Day 11, Day 15, Day 22, Day 29, Day 36, Day 43, Day 50, and Day 57 post dose. Pre-dose measurements served as the baseline for each animal Concentrations of total subject m-Ab REGN9933 (all drug, independent of the presence of target) in serum and total FXI (subject m-Ab REGN9933-bound and free) in plasma were determined by enzyme-linked immunosorbent assay (ELISA). Various PD analyses were performed using plasma samples, which included the measurement of the effects of the subject m-Ab REGN9933 on the coagulation pathway using clotting assays and TGAs. In these assays, coagulation was induced in plasma samples by either EA or TF to measure the effects of the subject m-Ab REGN9933 on the intrinsic or extrinsic coagulation pathways, respectively. Total FXI concentrations as well as measurements from the clotting assays and TGAs were normalized to baseline (i.e., pre-dose measurements), and expressed as changes relative to baseline.

Figures 10A, 10B:
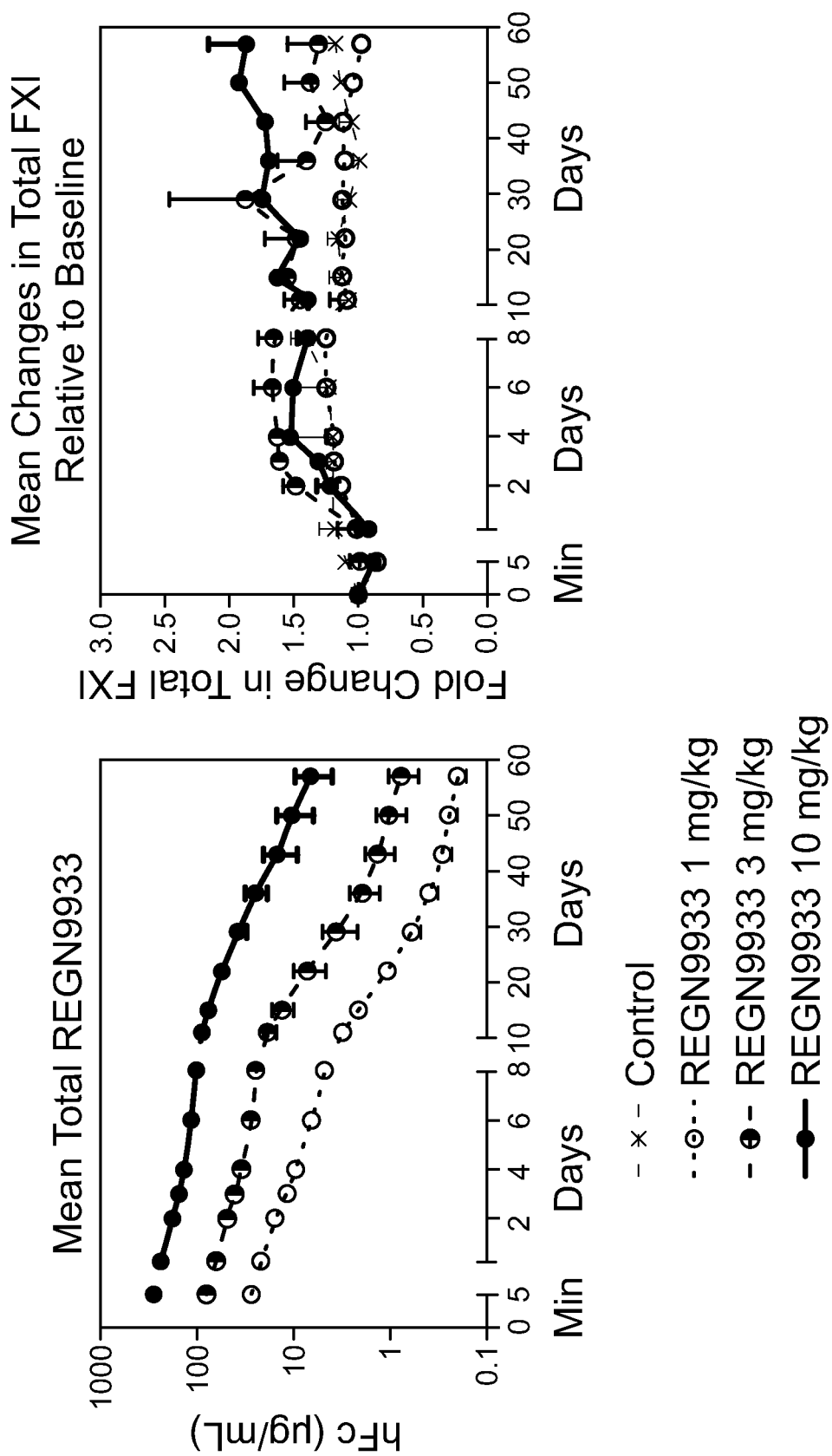
FIGS. 10A-10B: REGN9933 is associated with increases in total FXI levels in plasma. Female cynomolgus monkeys were administered a single intravenous (IV) slow bolus injection of vehicle (control, n=3), 1 mg/kg of REGN9933 (n=3), 3 mg/kg of REGN9933 (n=3), or 10 mg/kg of REGN9933 (n=3) and monitored for 8 weeks post dose. Blood samples were collected from all animals pre dose and at 5 minutes, 6 hours, Day 2, Day 3, Day 4, Day 6, Day 8, Day 11, Day 15, Day 22, Day 29, Day 36, Day 43, Day 50, and Day 57 post dose. Pre-dose measurements served as the baseline for each animal (FIGS. 10A and 10B).

9.2.1.1: Evaluation of the Effect of Subject mAb REGN9933 on Total FXI Levels in Plasma Concentration-time profiles of total subject m-Ab REGN9933 were characterized by an initial brief distribution phase followed by a brief linear beta elimination phase and a terminal target-mediated elimination phase. Peak subject m-Ab REGN9933 concentrations increased in a dose-proportional manner while dose-normalized subject m-Ab REGN9933 exposures indicated a greater than dose-proportional increase in exposure across the dose groups (FIG. 10A).

Increases in total FXI relative to baseline were observed with subject m-Ab REGN9933 doses≥3 mg/kg. Statistically significant increases in total FXI relative to baseline were observed for only the 10 mg/kg subject m-Ab REGN9933 group as compared to the control group (FIG. 10B). These increases were associated with greater than dose-proportional increases in exposure to total subject m-Ab REGN9933 across the dose groups. The subject m-Ab REGN9933 was not associated with a decrease in concentrations of total FXI in plasma, likely due to stabilization of FXI in circulation by binding with the subject m-Ab REGN9933.

Figures 11A, 11B:
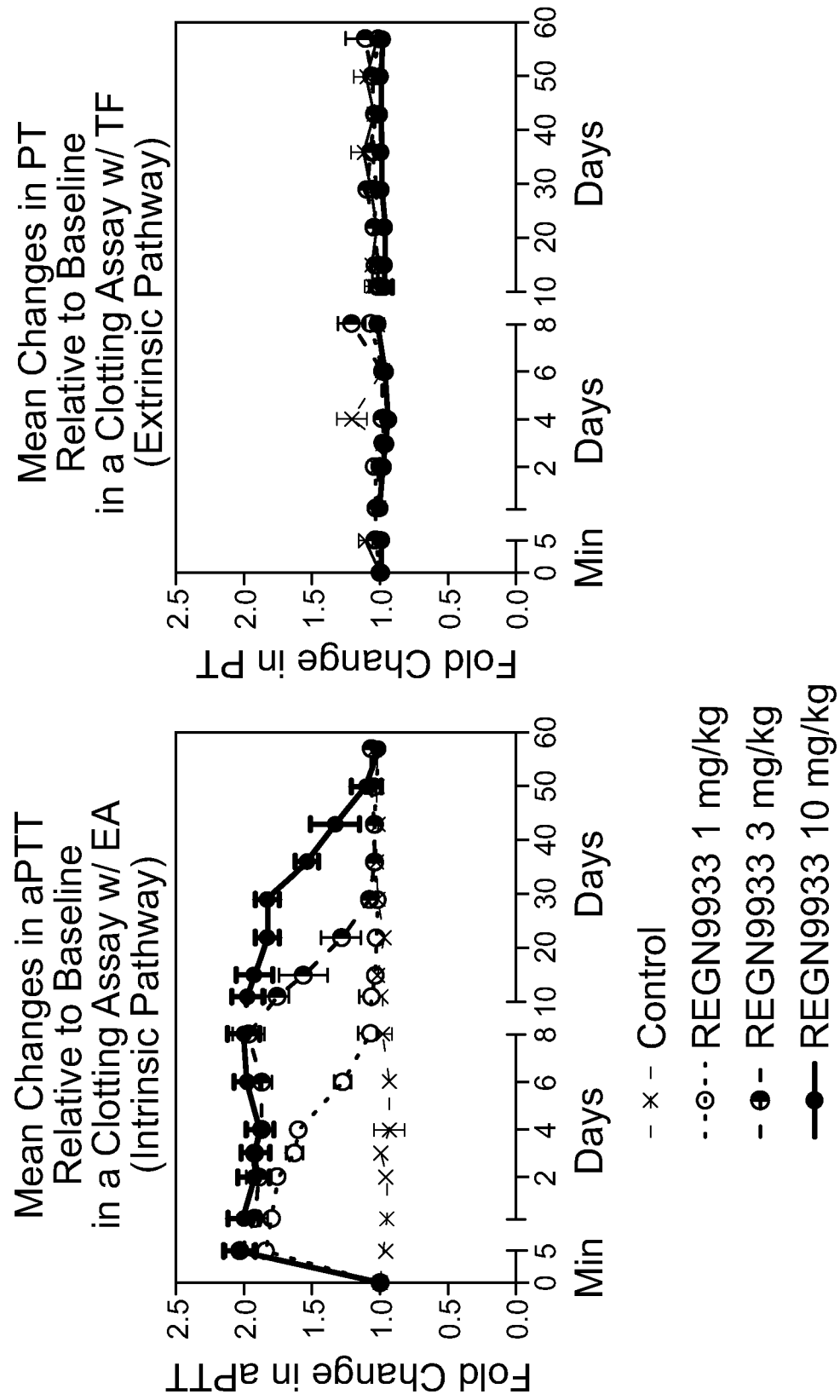
FIGS. 11A-11B: REGN9933 prolongs aPTT, but not PT, With a dose-dependent effect on duration. Female cynomolgus monkeys were administered a single intravenous (IV) slow bolus injection of vehicle (control, n=3), 1 mg/kg of REGN9933 (n=3), 3 mg/kg REGN9933 (n=3), or 10 mg/kg of REGN9933 (n=3) and monitored for 8 weeks post dose. Blood samples were collected from all animals pre dose and at 5 minutes, 6 hours, Day 2, Day 3, Day 4, Day 6, Day 8, Day 11, Day 15, Day 22, Day 29, Day 36, Day 43, Day 50, and Day 57 post dose. Pre-dose measurements served as the baseline for each animal (FIGS. 11A and 11B).

9.2.1.2: Evaluation of the Effect of the Subject m-Ab REGN9933 on aPTT and PT in Plasma The subject m-Ab REGN9933 prolonged activated partial thromboplastin time (aPTT), an indicator of intrinsic pathway activity, relative to baseline at all dose levels tested, with a dose-dependent effect on duration of activity. No effect on prothrombin time (PT), an indicator of extrinsic pathway activity, relative to baseline was observed with the subject m-Ab REGN9933 at any dose level tested (FIG. 11B).

9.2.1.3: Evaluation of the Effect of REGN9933 on Thrombin Generation in Plasma

Figures 12A, 12B:
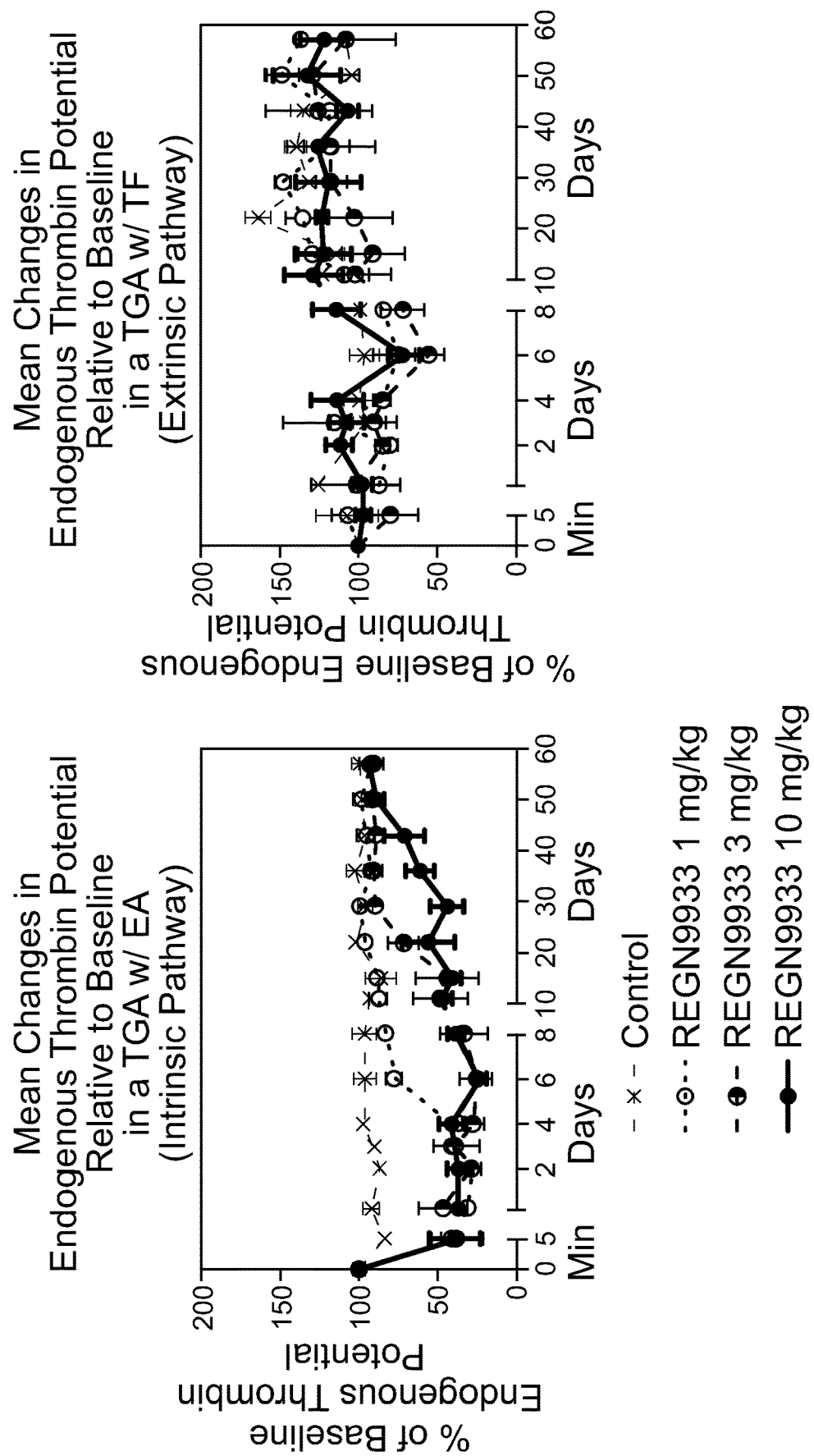
FIGS. 12A-12B REGN9933 reduces endogenous thrombin pPotential of the intrinsic and extrinsic coagulation pathways, with a dose-dependent effect on duration of activity in the intrinsic pathway. Female cynomolgus monkeys were administered a single intravenous (IV) slow bolus injection of vehicle (control, n=3), 1 mg/kg of REGN9933 (n=3), 3 mg/kg of REGN9933 (n=3), or 10 mg/kg of REGN9933 (n=3) and monitored for 8 weeks post dose. Blood samples were collected from all animals pre dose and at 5 minutes, 6 hours, Day 2, Day 3, Day 4, Day 6, Day 8, Day 11, Day 15, Day 22, Day 29, Day 36, Day 43, Day 50, and Day 57 post dose. Pre-dose measurements served as the baseline for each animal. Thrombin generation assays (TGAs) were performed with plasma samples using ellagic acid (EA) and tissue factor (TF) as activators of the intrinsic and extrinsic coagulation pathways, respectively (FIGS. 12A and 12B).

In a TGA induced with EA (TGA-EA), the subject m-Ab REGN9933 prolonged the lag time of thrombin generation (data not shown), reduced peak thrombin levels (data not shown), and reduced endogenous thrombin potential (FIG. 12A) mediated by the intrinsic pathway, relative to baseline, at all dose levels tested, with a dose-dependent effect on the duration of activity. In a TGA induced with TF (TGA-TF), no effect on the lag time of thrombin generation mediated by the extrinsic pathway, relative to baseline, was observed with the subject m-Ab REGN9933 at any dose level tested (data not shown). The subject m-Ab REGN9933 doses reduced peak thrombin levels (data not shown) and endogenous thrombin potential (FIG. 12B) mediated by the extrinsic pathway, relative to baseline, at all dose levels tested. However, the effects of the subject m-Ab REGN9933 on the extrinsic pathway were smaller in magnitude compared to the effects on the intrinsic pathway, and neither the magnitude nor the duration of the effects on the extrinsic pathway appeared to be dose-dependent.

Statistically significant effects on the intrinsic coagulation pathway relative to baseline, measured in the TGA, were observed up to Day 6, Day 11, and Day 50 in the 1, 3, and 10 mg/kg subject m-Ab REGN9933 groups, respectively, compared to the control group (data not shown). All parameters returned to baseline or close to baseline levels by the end of the 8-week study.

9.2.2: Ex Vivo Assessment of Single Doses of 0.5, 5, or 30 mg/kg of the Subject m-Ab REGN9933 IV or 30 mg/kg of the Subject m-Ab REGN9933 SC on Coagulation Pathway Activity in Cynomolgus Monkeys A PK/PD study in female cynomolgus monkeys was performed (data not shown). Ex vivo assays were performed to evaluate the effects of the subject m-Ab REGN9933 on coagulation using blood samples collected over a 10-week monitoring period. The subject m-Ab REGN9933 was given as a single dose to the animals at 0.5, 5, or 30 mg/kg (n=5 per group) IV or 30 mg/kg (n=5 per group) SC.

9.2.2.1: Evaluation of the Effect of the Subject m-Ab REGN9933 on Total FXI Levels in Plasma Concentration-time profiles of total subject m-Ab REGN9933 were characterized by an initial brief distribution phase followed by a brief linear beta elimination phase, a terminal target-mediated elimination phase, and a post target-mediated elimination phase (data not shown). Peak subject m-Ab REGN9933 concentrations increased in a dose-proportional manner (data not shown). Greater than dose-proportional increases in dose-normalized subject m-Ab REGN9933 exposures were observed across the dose groups, consistent with nonlinear kinetics that is more pronounced at low doses and concentrations of the subject m-Ab REGN9933 (data not shown). These findings are consistent with the observed decrease in clearance with increasing dose and associated concentrations. Following administration of the subject m-Ab REGN9933, concentrations of soluble FXI in plasma increased 1.0 to 1.9-fold across all dose groups (IV and SC) compared to baseline levels, indicating that there was a drug effect relative to baseline. However, there was no correlation with the subject m-Ab REGN9933 concentrations in serum (data not shown).

9.2.2: Evaluation of the Effect of the Subject m-Ab REGN9933 on aPTT and PT in Plasma Ex vivo clotting-time assays were performed using plasma from blood samples collected over time to determine the effect of the subject m-Ab REGN9933 administration on aPTT, an indicator of intrinsic pathway activity, and on PT, an indicator of extrinsic pathway activity. Blood sample collections prior to Day 3 were performed with the incorrect anticoagulant, ethylenediaminetetraacetic acid (EDTA), while sample collections from Day 3 to Day 71 were performed with the preferred anticoagulant, sodium citrate, which interferes less with the performance of coagulation assays. Therefore, only values generated for blood samples from Day 3 to Day 71 were plotted, and, instead of the study-specific pre-dose measurement in coagulation assays, combined values from this and the previous PK/PD study in cynomolgus monkeys (data not shown) were used to determine a historical baseline for aPTT and PT.

The subject m-Ab REGN9933 prolonged mean aPTT with 1.5- to 2.1-fold increases relative to historical baseline with a dose-dependent effect on duration of activity, but with similar magnitude across all tested dosing groups (data not shown). While the first occurrence of a ≥1.5-fold increase in aPTT relative to historical baseline was observed on Day 3 for all dose levels, this effect was observed for an increasing duration of 1, 19, or 54 days at increasing dose levels of 0.5 mg/kg (IV), 5 mg/kg (IV), and 30 mg/kg (IV) of the subject m-Ab REGN9933, respectively. Additionally, a ≥1.5-fold increase in aPTT relative to historical baseline was observed for 47 days following dosing with 30 mg/kg (SC) of the subject m-Ab REGN9933. Across all dosing groups, the maximum mean effect was a 2.1-fold increase in aPTT prolongation.

No effect on PT relative to historical baseline was observed with the subject m-Ab REGN9933 at any dose level tested (data not shown).

9.2.3: Discussion

The subject m-Ab REGN9933-mediated blockade of the coagulation pathway was assessed in clotting assays and TGAs using plasma from cynomolgus monkeys that received a single IV dose of 1, 3, or 10 mg/kg of the subject m-Ab REGN9933 and in TGAs using plasma from cynomolgus monkeys that received a single dose of 0.5, 5, or 30 mg/kg of the subject m-Ab REGN9933 via IV or 30 mg/kg of the subject m-Ab REGN9933 via SC. In the clotting assays performed in each of the aforementioned studies, the subject m-Ab REGN9933 blocked the intrinsic coagulation pathway with a dose-dependent effect on duration, but not magnitude; no effects on the extrinsic coagulation pathway were observed. In TGAs performed, of the subject m-Ab REGN9933 blocked the intrinsic coagulation pathway with a dose-dependent effect on duration, but not magnitude; minimal effects on the extrinsic coagulation pathway were observed.

Example 10: Safety Pharmacology

Safety pharmacology endpoints were integrated into a GLP repeat-dose toxicology study conducted in cynomolgus monkeys (data not shown). At doses up to 100 mg/kg/week (SC or IV), the highest dose administered, there were no test article-related cardiovascular (heart rate, blood pressure, and electrocardiography), respiratory (breaths/minute and pulse oximetry), or central nervous system changes evident.

We claim:

1. An isolated antibody, or antigen-binding fragment thereof, that binds to the apple 2 (A2) domain of coagulation factor XI (FXI), wherein the antibody, or antigen-binding fragment thereof, comprises a heavy chain variable region (HCVR) comprising a heavy chain complementarity determining region (HCDR) 1, HCDR2, and HCDR3, and a light chain variable region (LCVR) comprising a light chain complementarity determining region (LCDR) 1, LCDR2, and LCDR3, wherein
  (a) the HCDR1 comprises the amino acid sequence of SEQ ID NO: 5;
  (b) the HCDR2 comprises the amino acid sequence of SEQ ID NO: 7;
  (c) the HCDR3 comprises the amino acid sequence of SEQ ID NO: 9;
  (d) the LCDR1 comprises the amino acid sequence of SEQ ID NO: 15;
  (e) the LCDR2 comprises the amino acid sequence of SEQ ID NO: 17; and
  (f) the LCDR3 comprises the amino acid sequence of SEQ ID NO: 19; or
wherein
  (a) the HCDR1 comprises the amino acid sequence of SEQ ID NO: 33;
  (b) the HCDR2 comprises the amino acid sequence of SEQ ID NO: 35;
  (c) the HCDR3 comprises the amino acid sequence of SEQ ID NO: 37;
  (d) the LCDR1 comprises the amino acid sequence of SEQ ID NO: 15;
  (e) the LCDR2 comprises the amino acid sequence of SEQ ID NO: 17; and
  (f) the LCDR3 comprises the amino acid sequence of SEQ ID NO: 19.

2. The isolated antibody, or antigen-binding fragment thereof, of claim 1, wherein the HCVR comprises an amino acid sequence having at least 90% identity to SEQ ID NO: 3, and wherein the LCVR comprises an amino acid sequence having at least 90% identity to SEQ ID NO: 13, or
  wherein the HCVR comprises an amino acid sequence having at least 90% identity to SEQ ID NO: 31, and wherein the LCVR comprises an amino acid sequence having at least 90% identity to SEQ ID NO: 13.

3. The isolated antibody, or antigen-binding fragment thereof, of claim 2, wherein the HCVR comprises the amino acid sequence of SEQ ID NO: 3, and wherein the LCVR comprises the amino acid sequence of SEQ ID NO: 13, or
  wherein the HCVR comprises the amino acid sequence of SEQ ID NO: 31, and wherein the LCVR comprises the amino acid sequence of SEQ ID NO: 13.

4. The isolated antibody, or antigen-binding fragment thereof, of claim 1, wherein the antibody, or antigen-binding fragment thereof, comprises a heavy chain variable region (HCVR) comprising an amino acid sequence having at least 95% identity to SEQ ID NO: 3 and a light chain variable region (LCVR) comprising an amino acid sequence having at least 95% identity to SEQ ID NO: 13, or a heavy chain variable region (HCVR) comprising an amino acid sequence having at least 95% identity to SEQ ID NO: 31 and a light chain variable region (LCVR) comprising an amino acid sequence having at least 95% identity to SEQ ID NO: 13.

5. The isolated antibody, or antigen-binding fragment thereof, of claim 4, wherein the HCVR comprises the amino acid sequence of SEQ ID NO: 3, and wherein the LCVR comprises the amino acid sequence of SEQ ID NO: 13, or
  wherein the HCVR comprises the amino acid sequence of SEQ ID NO: 31, and wherein the LCVR comprises the amino acid sequence of SEQ ID NO: 13.

6. The isolated antibody or antigen-binding fragment of claim 1, wherein the antibody, or antigen-binding fragment thereof, binds human FXI with a KD of less than about 1,000 pM as measured by surface plasmon resonance at 25° C. or 37° C.

7. The isolated antibody or antigen-binding fragment of claim 6, wherein the antibody, or antigen-binding fragment thereof, binds human FXI with a KD selected from the group consisting of less than 800 pM, less than 500 pM, less than 100 pM, and less than 50 pM as measured by surface plasmon resonance at 25° C. or 37° C.

8. The isolated antibody or antigen-binding fragment of claim 1, wherein the antibody, or antigen-binding fragment thereof, binds human FXI with a dissociative half-life (t½) selected from the group consisting of greater than 10 minutes, greater than 60 minutes, greater than 500 minutes, and greater than 1,000 minutes as measured by surface plasmon resonance at 25° C. or 37° C.

9. The isolated antibody or antigen-binding fragment of claim 1, wherein the antibody, or antigen-binding fragment thereof, inhibits activation of human coagulation factor X (FX) with an IC50 of less than 10 nM.

10. The isolated antibody or antigen-binding fragment of claim 1, wherein the antibody, or antigen-binding fragment thereof, inhibits activation of human coagulation factor X (FX) with an IC50 of less than 40 pM.

11. The isolated antibody or antigen-binding fragment of claim 1, wherein the antibody, or antigen-binding fragment thereof, increases by at least two-fold activated partial thromboplastin time (aPTT).

12. The isolated antibody or antigen-binding fragment of claim 11, wherein the antibody, or antigen-binding fragment thereof, does not increase prothrombin time (PT).

13. The isolated antibody or antigen-binding fragment of claim 1, wherein the antibody, or antigen-binding fragment thereof, inhibits FXIa-mediated thrombin activity by at least 5%, by at least 10%, by at least 15%, or by 5%-15%.

14. The isolated antibody or antigen-binding fragment of claim 1, wherein the antibody, or antigen-binding fragment thereof, prolongs aPTT by at least two-fold in human plasma at a concentration ≤100 nM, ≤75 nM, or ≤50 nM.

15. The isolated antibody or antigen-binding fragment of claim 14, wherein the antibody, or antigen-binding fragment thereof, does not prolong PT.

16. The isolated antibody, or antigen-binding fragment thereof, of claim 1, wherein the antibody, or antigen-binding fragment thereof, inhibits thrombin production or activation via the intrinsic coagulation pathway in human plasma at a concentration of at least 10 nM, at least 25 nM, or at least 50 nM without affecting thrombin production or activation via the extrinsic coagulation pathway.

17. A pharmaceutical composition comprising the antibody, or antigen-binding fragment thereof, of claim 1, and a pharmaceutically acceptable carrier or diluent.

18. An isolated nucleic acid molecule comprising a polynucleotide sequence that encodes the antibody, or antigen-binding fragment thereof, according to claim 1.

19. A vector comprising the nucleic acid molecule of claim 18.

20. A cell comprising the nucleic acid molecule of claim 18.

* * * * *

SEQUENCE LISTING

```
Sequence total quantity: 38
SEQ ID NO: 1            moltype = AA  length = 450
FEATURE                 Location/Qualifiers
source                  1..450
                        mol_type = protein
                        organism = Homo sapiens
SEQUENCE: 1
EVQLVESGGG LVQPGGSLRL SCAASGFTFS NYAMNWVRQA PGKGLDWVSF IRSGGDTTYY   60
ADSVKGRFTI SRDNSKNTLY LQMNSLRAED TAVYYCAKVH PYTWDYGDAF DIWGQGTMVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFLGG  240
PSVFLFPPKP KDTLMISRTP EVTCVVVDVS QEDPEVQFNW YVDGVEVHNA KTKPREEQFN  300
```

```
STYRVVSVLT VLHQDWLNGK EYKCKVSNKG LPSSIEKTIS KAKGQPREPQ VYTLPPSQEE   360
MTKNQVSLTC LVKGFYPSDI AVEWESNGQP ENNYKTTPPV LDSDGSFFLY SRLTVDKSRW   420
QEGNVFSCSV MHEALHNHYT QKSLSLSLGK                                   450

SEQ ID NO: 2           moltype = DNA   length = 1353
FEATURE                Location/Qualifiers
source                 1..1353
                       mol_type = genomic DNA
                       organism = Homo sapiens
SEQUENCE: 2
gaggtgcagc tggtggagtc tgggggaggc ttggtacagc ctgggggtc cctgagactc    60
tcctgtgcag cctctggatt cacctttagc aactatgcca tgaactgggt ccgccaggct   120
ccagggaagg ggctggactg ggtctcattt attcgtagtg gtggtgatac acatactat   180
gcagactccg tgaagggccg gttcaccatc tccagagaca attccaagaa cacgctgtat   240
ctgcagatga acagcctgag agccgaggac acggccgtat attactgtgc gaaggttcat   300
ccatatacct gggattacgg tgatgctttt gatatctggg gccaggggac aatggtcacc   360
gtctcttcag cctccaccaa gggcccatcg gtcttcccc tggcgccctg ctccaggagc    420
acctccgaga gcacagccgc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acgaagacct acacctgcaa cgtagatcac aagcccagca acaccaaggt ggacaagaga   660
gttgagtcca aatatggtcc cccatgccca cctgcctgc cacctgagtt cctggggggga    720
ccatcagtct tcctgttccc cccaaaaccc aaggacactc tcatgatctc ccggacccct   780
gaggtcacgt gcgtggtggt ggacgtgagc caggaagacc ccgaggtcca gttcaactgg   840
tacgtggatg gcgtggaggt gcataatgcc aagacaaagc cgcgggagga gcagttcaac   900
agcacgtacc gtgtggtcag cgtcctcacc gtcctgcacc aggactggct gaacggcaag   960
gagtacaagt gcaaggtctc caacaaaggc ctcccgtcct ccatcgagaa aaccatctcc  1020
aaagccaaag gcagccccg agagccacag gtgtacaccc tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctca ccgtggacaa gagcaggtgg  1260
caggagggga atgtcttctc atgctccgtg atgcatgagg ctctgcacaa ccactacaca  1320
cagaagtccc tctccctgtc tctgggtaaa tga                              1353

SEQ ID NO: 3           moltype = AA    length = 123
FEATURE                Location/Qualifiers
source                 1..123
                       mol_type = protein
                       organism = Homo sapiens
SEQUENCE: 3
EVQLVESGGG LVQPGGSLRL SCAASGFTFS NYAMNWVRQA PGKGLDWVSF IRSGGDTTYY    60
ADSVKGRFTI SRDNSKNTLY LQMNSLRAED TAVYYCAKVH PYTWDYGDAF DIWGQGTMVT   120
VSS                                                                123

SEQ ID NO: 4           moltype = DNA   length = 369
FEATURE                Location/Qualifiers
source                 1..369
                       mol_type = genomic DNA
                       organism = Homo sapiens
SEQUENCE: 4
gaggtgcagc tggtggagtc tgggggaggc ttggtacagc ctgggggtc cctgagactc    60
tcctgtgcag cctctggatt cacctttagc aactatgcca tgaactgggt ccgccaggct   120
ccagggaagg ggctggactg ggtctcattt attcgtagtg gtggtgatac acatactat   180
gcagactccg tgaagggccg gttcaccatc tccagagaca attccaagaa cacgctgtat   240
ctgcagatga acagcctgag agccgaggac acggccgtat attactgtgc gaaggttcat   300
ccatatacct gggattacgg tgatgctttt gatatctggg gccaggggac aatggtcacc   360
gtctcttca                                                          369

SEQ ID NO: 5           moltype = AA    length = 8
FEATURE                Location/Qualifiers
source                 1..8
                       mol_type = protein
                       organism = Homo sapiens
SEQUENCE: 5
GFTFSNYA                                                             8

SEQ ID NO: 6           moltype = DNA   length = 24
FEATURE                Location/Qualifiers
source                 1..24
                       mol_type = genomic DNA
                       organism = Homo sapiens
SEQUENCE: 6
ggattcacct ttagcaacta tgcc                                          24

SEQ ID NO: 7           moltype = AA    length = 8
FEATURE                Location/Qualifiers
source                 1..8
                       mol_type = protein
                       organism = Homo sapiens
```

```
SEQUENCE: 7
IRSGGDTT                                                              8

SEQ ID NO: 8            moltype = DNA  length = 24
FEATURE                 Location/Qualifiers
source                  1..24
                        mol_type = genomic DNA
                        organism = Homo sapiens
SEQUENCE: 8
attcgtagtg gtggtgatac caca                                           24

SEQ ID NO: 9            moltype = AA   length = 16
FEATURE                 Location/Qualifiers
source                  1..16
                        mol_type = protein
                        organism = Homo sapiens
SEQUENCE: 9
AKVHPYTWDY GDAFDI                                                    16

SEQ ID NO: 10           moltype = DNA  length = 48
FEATURE                 Location/Qualifiers
source                  1..48
                        mol_type = genomic DNA
                        organism = Homo sapiens
SEQUENCE: 10
gcgaaggttc atccatatac ctgggattac ggtgatgctt ttgatatc                 48

SEQ ID NO: 11           moltype = AA   length = 215
FEATURE                 Location/Qualifiers
source                  1..215
                        mol_type = protein
                        organism = Homo sapiens
SEQUENCE: 11
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 12           moltype = DNA  length = 648
FEATURE                 Location/Qualifiers
source                  1..648
                        mol_type = genomic DNA
                        organism = Homo sapiens
SEQUENCE: 12
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccgat cacccttcggc   300
caagggacac gactggagat taaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttag                648

SEQ ID NO: 13           moltype = AA   length = 108
FEATURE                 Location/Qualifiers
source                  1..108
                        mol_type = protein
                        organism = Homo sapiens
SEQUENCE: 13
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 14           moltype = DNA  length = 324
FEATURE                 Location/Qualifiers
source                  1..324
                        mol_type = genomic DNA
                        organism = Homo sapiens
SEQUENCE: 14
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccgat cacccttcggc   300
caagggacac gactggagat taaa                                          324

SEQ ID NO: 15           moltype = AA   length = 6
```

| FEATURE | Location/Qualifiers |
|---|---|
| source | 1..6 |
| | mol_type = protein |
| | organism = Homo sapiens |

SEQUENCE: 15
QSISSY                                                                          6

| SEQ ID NO: 16 | moltype = DNA   length = 18 |
|---|---|
| FEATURE | Location/Qualifiers |
| source | 1..18 |
| | mol_type = genomic DNA |
| | organism = Homo sapiens |

SEQUENCE: 16
cagagcatta gcagctat                                                            18

| SEQ ID NO: 17 | moltype =    length = |
|---|---|

SEQUENCE: 17
000

| SEQ ID NO: 18 | moltype =    length = |
|---|---|

SEQUENCE: 18
000

| SEQ ID NO: 19 | moltype = AA   length = 10 |
|---|---|
| FEATURE | Location/Qualifiers |
| source | 1..10 |
| | mol_type = protein |
| | organism = Homo sapiens |

SEQUENCE: 19
QQSYSTPPIT                                                                     10

| SEQ ID NO: 20 | moltype = DNA   length = 30 |
|---|---|
| FEATURE | Location/Qualifiers |
| source | 1..30 |
| | mol_type = genomic DNA |
| | organism = Homo sapiens |

SEQUENCE: 20
caacagagtt acagtacccc tccgatcacc                                               30

| SEQ ID NO: 21 | moltype = AA   length = 625 |
|---|---|
| FEATURE | Location/Qualifiers |
| source | 1..625 |
| | mol_type = protein |
| | organism = Homo sapiens |

SEQUENCE: 21
MIFLYQVVHF ILFTSVSGEC VTQLLKDTCF EGGDITTVFT PSAKYCQVVC TYHPRCLLFT      60
FTAESPSEDP TRWFTCVLKD SVTETLPRVN RTAAISGYSF KQCSHQISAC NKDIYVDLDM     120
KGINYNSSVA KSAQECQERC TDDVHCHFFT YATRQFPSLE HRNICLLKHT QTGTPTRITK     180
LDKVVSGFSL KSCALSNLAC IRDIFPNTVF ADSNIDSVMA PDAFVCGRIC THHPGCLFFT     240
FFSQEWPKES QRNLCLLKTS ESGLPSTRIK KSKALSGFSL QSCRHSIPVF CHSSFYHDTD     300
FLGEELDIVA AKSHEACQKL CTNAVRCQFF TYTPAQASCN EGKGKCYLKL SSNGSPTKIL     360
HGRGGISGYT LRLCKMDNEC TTKIKPRIVG GTASVRGEWP WQVTLHTTSP TQRHLCGGSI     420
IGNQWILTAA HCFYGVESPK ILRVYSGILN QSEIKEDTSF FGVQEIIIHD QYKMAESGYD     480
IALLKLETTV NYTDSQRPIC LPSKGDRNVI YTDCWVTGWG YRKLRDKIQN TLQKAKIPLV     540
TNEECQKRYR GHKITHKMIC AGYREGGKDA CKGDSGGPLS CKHNEVWHLV GITSWGEGCA     600
QRERPGVYTN VVEYVDWILE KTQAV                                          625

| SEQ ID NO: 22 | moltype = AA   length = 635 |
|---|---|
| FEATURE | Location/Qualifiers |
| REGION | 1..635 |
| | note = Synthetic |
| source | 1..635 |
| | mol_type = protein |
| | organism = synthetic construct |

SEQUENCE: 22
ECVTQLLKDT CFEGGDITTV FTPSAKYCQV VCTYHPRCLL FTFTAESPSE DPTRWFTCVL      60
KDSVTETLPR VNRTAAISGY SFKQCSHQIS ACNKDIYVDL DMKGINYNSS VAKSAQECQE     120
RCTDDVHCHF FTYATRQFPS LEHRNICLLK HTQTGTPTRI TKLDKVVSGF SLKSCALSNL     180
ACIRDIFPNT VFADSNIDSV MAPDAFVCGR ICTHHPGCLF FTFFSQEWPK ESQRNLCLLK     240
TSESGLPSTR IKKSKALSGF SLQSCRHSIP VFCHSSFYHD TDFLGEELDI VAAKSHEACQ     300
KLCTNAVRCQ FFTYTPAQAS CNEGKGKCYL KLSSNGSPTK ILHGRGGISG YTLRLCKMDN     360
ECTTKIKPRI VGGTASVRGE WPWQVTLHTT SPTQRHLCGG SIIGNQWILT AAHCFYGVES     420
PKILRVYSGI LNQSEIKEDT SFFGVQEIII HDQYKMAESG YDIALLKLET TVNYTDSQRP     480
ICLPSKGDRN VIYTDCWVTG WGYRKLRDKI QNTLQKAKIP LVTNEECQKR YRGHKITHKM     540
ICAGYREGGK DACKGDSGGP LSCKHNEVWH LVGITSWGEG CAQRERPGVY TNVVEYVDWI     600
LEKTQAVEQK LISEEDLGGE QKLISEEDLH HHHH                                635

| SEQ ID NO: 23 | moltype = AA   length = 634 |
|---|---|
| FEATURE | Location/Qualifiers |

```
REGION                      1..634
                            note = Synthetic
source                      1..634
                            mol_type = protein
                            organism = synthetic construct
SEQUENCE: 23
GCLTQLYENA FFRGGDVASM YTPNAQYCQM RCTFHPRCLL FSFLPASSIN DMEKRFGCFL    60
KDSVTGTLPK VHRTGAVSGH SLKQCHQISA CNKDIYVDLD MKGINYNSSV AKSAQECQER   120
CTDDVHCHFF TYATRQFPSL EHRNICLLKH TQTGTPTRIT KLDKVVSGFS LKSCALSNLA   180
CIRDIFPNTV FADSNIDSVM APDAFVCGRI CTHHPGCLFF TFFSQEWPKE SQRNLCLLKT   240
SESGLPSTRI KKSKALSGFS LQSCRHSIPV FCHSSFYHDT DFLGEELDIV AAKSHEACQK   300
LCTNAVRCQF FTYTPAQASC NEGKGKCYLK LSSNGSPTKI LHGRGGISGY TLRLCKMDNE   360
CTTKIKPRIV GGTASVRGEW PWQVTLHTTS PTQRHLCGGS IIGNQWILTA AHCFYGVESP   420
KILRVYSGIL NQSEIKEDTS FFGVQEIIIH DQYKMAESGY DIALLKLETT VNYTDSQRPI   480
CLPSKGDRNV IYTDCWVTGW GYRKLRDKIQ NTLQKAKIPL VTNEECQKRY RGHKITHKMI   540
CAGYREGGKD ACKGDSGGPL SCKHNEVWHL VGITSWGEGC AQRERPGVYT NVVEYVDWIL   600
EKTQAVEQKL ISEEDLGGEQ KLISEEDLHH HHHH                               634

SEQ ID NO: 24               moltype = AA  length = 633
FEATURE                     Location/Qualifiers
REGION                      1..633
                            note = Synthetic
source                      1..633
                            mol_type = protein
                            organism = synthetic construct
SEQUENCE: 24
ECVTQLLKDT CFEGGDITTV FTPSAKYCQV VCTYHPRCLL FTFTAESPSE DPTRWFTCVL    60
KDSVTETLPR VNRTAAISGY SFKQCSHQIS CHRDIYKGVD MRGVNFNVSK VSSVEECQKR   120
CTNNIRCQFF SYATQTFHKA EYRNNCLLKY SPGGTPTAIK VLSNVESGFS LKPCLSNLAC   180
IRDIFPNTVF ADSNIDSVMA PDAFVCGRIC THHPGCLFFF FFSQEWPKES QRNLCLLKTS   240
ESGLPSTRIK KSKALSGFSL QSCRHSIPVC HSSFYHDTD FLGEELDIVA AKSHEACQKL    300
CTNAVRCQFF TYTPAQASCN EGKGKCYLKL SSNGSPTKIL HGRGGISGYT LRLCKMDNEC   360
TTKIKPRIVG GTASVRGEWP WQVTLHTTSP TQRHLCGGSI IGNQWILTAA HCFYGVESPK   420
ILRVYSGILN QSEIKEDTSF FGVQEIIIHD QYKMAESGYD IALLKLETTV NYTDSQRPIC   480
LPSKGDRNVI YTDCWVTGWG YRKLRDKIQN TLQKAKIPLV TNEECQKRYR GHKITHKMIC   540
AGYREGGKDA CKGDSGGPLS CKHNEVWHLV GITSWGEGCA QRERPGVYTN VVEYVDWILE   600
KTQAVEQKLI SEEDLGGEQK LISEEDLHHH HHH                                633

SEQ ID NO: 25               moltype = AA  length = 633
FEATURE                     Location/Qualifiers
REGION                      1..633
                            note = Synthetic
source                      1..633
                            mol_type = protein
                            organism = synthetic construct
SEQUENCE: 25
ECVTQLLKDT CFEGGDITTV FTPSAKYCQV VCTYHPRCLL FTFTAESPSE DPTRWFTCVL    60
KDSVTETLPR VNRTAAISGY SFKQCSHQIS ACNKDIYVDL DMKGINYNSS VAKSAQECQE   120
RCTDDVHCHF FTYATRQFPS LEHRNICLLK HTQTGTPTRI TKLDKVVSGF SLKSCALSNL   180
CHMNIFQHLA FSDVDVARVL TPDAFVCRTI CTYHPNCLFF TFYTNVWKIE SQRNVCLLKT   240
SESGLPSSST PQENTISGYS LLTCHSIPVF CHSSFYHDTD FLGEELDIVA AKSHEACQKL   300
CTNAVRCQFF TYTPAQASCN EGKGKCYLKL SSNGSPTKIL HGRGGISGYT LRLCKMDNEC   360
TTKIKPRIVG GTASVRGEWP WQVTLHTTSP TQRHLCGGSI IGNQWILTAA HCFYGVESPK   420
ILRVYSGILN QSEIKEDTSF FGVQEIIIHD QYKMAESGYD IALLKLETTV NYTDSQRPIC   480
LPSKGDRNVI YTDCWVTGWG YRKLRDKIQN TLQKAKIPLV TNEECQKRYR GHKITHKMIC   540
AGYREGGKDA CKGDSGGPLS CKHNEVWHLV GITSWGEGCA QRERPGVYTN VVEYVDWILE   600
KTQAVEQKLI SEEDLGGEQK LISEEDLHHH HHH                                633

SEQ ID NO: 26               moltype = AA  length = 633
FEATURE                     Location/Qualifiers
REGION                      1..633
                            note = Synthetic
source                      1..633
                            mol_type = protein
                            organism = synthetic construct
SEQUENCE: 26
ECVTQLLKDT CFEGGDITTV FTPSAKYCQV VCTYHPRCLL FTFTAESPSE DPTRWFTCVL    60
KDSVTETLPR VNRTAAISGY SFKQCSHQIS ACNKDIYVDL DMKGINYNSS VAKSAQECQE   120
RCTDDVHCHF FTYATRQFPS LEHRNICLLK HTQTGTPTRI TKLDKVVSGF SLKSCALSNL   180
ACIRDIFPNT VFADSNIDSV MAPDAFVCGR ICTHHPGCLF FTFFSQEWPK ESQRNLCLLK   240
TSESGLPSTR IKKSKALSGF SLQSCRHSIP VCHSKIYPGV DFGGEELNVT FVKGVNVCQE   300
TCTKMIRCQF FTYSLLPEDC KEEKGKCFLR LSMDGSPTRI AYGTQGSSGY SLRLCMDNEC   360
TTKIKPRIVG GTASVRGEWP WQVTLHTTSP TQRHLCGGSI IGNQWILTAA HCFYGVESPK   420
ILRVYSGILN QSEIKEDTSF FGVQEIIIHD QYKMAESGYD IALLKLETTV NYTDSQRPIC   480
LPSKGDRNVI YTDCWVTGWG YRKLRDKIQN TLQKAKIPLV TNEECQKRYR GHKITHKMIC   540
AGYREGGKDA CKGDSGGPLS CKHNEVWHLV GITSWGEGCA QRERPGVYTN VVEYVDWILE   600
KTQAVEQKLI SEEDLGGEQK LISEEDLHHH HHH                                633

SEQ ID NO: 27               moltype = AA  length = 647
```

```
FEATURE              Location/Qualifiers
REGION               1..647
                     note = Synthetic
source               1..647
                     mol_type = protein
                     organism = synthetic construct
SEQUENCE: 27
GCLTQLYENA FFRGGDVASM YTPNAQYCQM RCTFHPRCLL FSFLPASSIN DMEKRFGCFL    60
KDSVTGTLPK VHRTGAVSGH SLKQCGHQIS ACHRDIYKGV DMRGVNFNVS KVSSVEECQK   120
RCTNNIRCQF FSYATQTFHK AEYRNNCLLK YSPGGTPTAI KVLSNVESGF SLKPCALSEI   180
GCHMNIFQHL AFSDVDVARV LTPDAFVCRT ICTYHPNCLF FTFYTNVWKI ESQRNVCLLK   240
TSESGTPSSS TPQENTISGY SLLTCKRTLP EPCHSKIYPG VDFGGEELNV TFVKGVNVCQ   300
ETCTKMIRCQ FFTYSLLPED CKEEKCKCFL RLSMDGSPTR IAYGTQGSSG YSLRLCNTGD   360
NSVCTTKTST RIVGGTNSSW GEWPWQVSLQ VKLTAQRHLC GGSLIGHQWV LTAAHCFDGL   420
PLQDVWRIYS GILNLSDITK DTPFSQIKEI IIHQNYKVSE GNHDIALIKL QAPLNYTEFQ   480
KPICLPSKGD TSTIYTNCWV TGWGFSKEKG EIQNILQKVN IPLVTNEECQ KRYQDYKITQ   540
RMVCAGYKEG GKDACKGDSG GPLVCKHNGM WRLVGITSWG EGCARREQPG VYTKVAEYMD   600
WILEKTQSSD GKAQMQSPAE QKLISEEDLG GEQKLISEED LHHHHHH               647

SEQ ID NO: 28        moltype = AA  length = 638
FEATURE              Location/Qualifiers
source               1..638
                     mol_type = protein
                     organism = Homo sapiens
SEQUENCE: 28
MILFKQATYF ISLFATVSCG CLTQLYENAF FRGGDVASMY TPNAQYCQMR CTFHPRCLLF    60
SFLPASSIND MEKRFGCFLK DSVTGTLPKV HRTGAVSGHS LKQCGHQISA CHRDIYKGVD   120
MRGVNFNVSK VSSVEECQKR CTNNIRCQFF SYATQTFHKA EYRNNCLLKY SPGGTPTAIK   180
VLSNVESGFS LKPCALSEIG CHMNIFQHLA FSDVDVARVL TPDAFVCRTI CTYHPNCLFF   240
TFYTNVWKIE SQRNVCLLKT SESGTPSSST PQENTISGYS LLTCKRTLPE PCHSKIYPGV   300
DFGGEELNVT FVKGVNVCQE TCTKMIRCQF FTYSLLPEDC KEEKCKCFLR LSMDGSPTRI   360
AYGTQGSSGY SLRLCNTGDN SVCTTKTSTR IVGGTNSSWG EWPWQVSLQV KLTAQRHLCG   420
GSLIGHQWVL TAAHCFDGLP LQDVWRIYSG ILNLSDITKD TPFSQIKEII IHQNYKVSEG   480
NHDIALIKLQ APLNYTEFQK PICLPSKGDT STIYTNCWVT GWGFSKEKGE IQNILQKVNI   540
PLVTNEECQK RYQDYKITQR MVCAGYKEGG KDACKGDSGG PLVCKHNGMW RLVGITSWGE   600
GCARREQPGV YTKVAEYMDW ILEKTQSSDG KAQMQSPA                        638

SEQ ID NO: 29        moltype = AA  length = 448
FEATURE              Location/Qualifiers
source               1..448
                     mol_type = protein
                     organism = Homo sapiens
SEQUENCE: 29
QVQLVESGGG VVQPGRSLRL SCAASGFTFS SYNMHWVRQA PGKGLEWVAI FLSYDGSNKY    60
YADSVKGRFT ISRDNSRDML YLQMNSLRAE DTAVYYCAKS EILVVPTLDY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGK                                   448

SEQ ID NO: 30        moltype = DNA  length = 1347
FEATURE              Location/Qualifiers
source               1..1347
                     mol_type = genomic DNA
                     organism = Homo sapiens
SEQUENCE: 30
caggtgcagc tggtggagtc tgggggaggc gtggtccagc ctgggaggtc cctgagactc    60
tcctgtgcag cctctggatt cacccttcag agctataaca tgcactgggt ccgccaggct   120
ccaggcaagg ggctggagtg ggtggcaatt ttttatcat atgatggaag taataaatac   180
tatgcagact ccgtgaaggg ccgattcacc atctccagag acaattccag ggacatgctg   240
tatctgcaaa tgaacagcct gagagctgag gacacggctg tctattactg tgcgaaatcg   300
gaaattttag tagtaccaac tcttgactac tgggggcagg gaaccctggt caccgtctcc   360
tcagcctcca ccaagggccc atcggtcttc cccctggcgc cctgctccag gagcacctcc   420
gagagcacag ccgccctggg ctgcctggtc aaggactact ccccgaacc ggtgacggtg    480
tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtccccatg cccacccctg ccagcacctg agttcctggg gggaccatca   720
gtcttcctgt tccccccaaa acccaaggac actctcatga tctcccggac ccctgaggtc   780
acgtgcgtgg tggtggacgt gagccaggaa gaccccgagg tccagttcaa ctggtacgtg   840
gatggcgtgg aggtgcataa tgccaagaca aagccgcggg aggagcagtt caacagcacg   900
taccgtgtgg tcagcgtcct caccgtcctg caccaggact ggctgaacgg caaggagtac   960
aagtgcaagg tctccaacaa aggcctcccg tcctccatcg agaaaaccat ctccaaagcc   1020
aaagggcagc cccgagagcc acaggtgtac accctgcccc catccaggga ggagatgacc   1080
aagaaccagg tcagcctgac ctgcctggtc aaaggcttct accccagcga catcgccgtg   1140
gagtgggaga gcaatgggca gccggagaac aactacaaga ccacgcctcc cgtgctggac   1200
tccgacggct ccttcttcct ctacagcagg ctcaccgtgg acaagagcag gtggcaggag   1260
```

```
gggaatgtct tctcatgctc cgtgatgcat gaggctctgc acaaccacta cacacagaag  1320
tccctctccc tgtctctggg taaatga                                      1347

SEQ ID NO: 31          moltype = AA  length = 121
FEATURE                Location/Qualifiers
source                 1..121
                       mol_type = protein
                       organism = Homo sapiens
SEQUENCE: 31
QVQLVESGGG VVQPGRSLRL SCAASGFTFS SYNMHWVRQA PGKGLEWVAI FLSYDGSNKY  60
YADSVKGRFT ISRDNSRDML YLQMNSLRAE DTAVYYCAKS EILVVPTLDY WGQGTLVTVS  120
S                                                                 121

SEQ ID NO: 32          moltype = DNA  length = 363
FEATURE                Location/Qualifiers
source                 1..363
                       mol_type = genomic DNA
                       organism = Homo sapiens
SEQUENCE: 32
caggtgcagc tggtggagtc tgggggaggc gtggtccagc ctgggaggtc cctgagactc  60
tcctgtgcag cctctggatt caccttcagt agctataaca tgcactgggt ccgccaggct  120
ccaggcaagg ggctggagtg ggtggcaatt tttttatcat atgatggaag taataaatac  180
tatgcagact ccgtgaaggg ccgattcacc atctccagag acaattccag ggacatgctg  240
tatctgcaaa tgaacagcct gagagctgag gacacggctg tctattactg tgcgaaatcg  300
gaaattttag tagtaccaac tcttgactac tggggccagg gaaccctggt caccgtctcc  360
tca                                                               363

SEQ ID NO: 33          moltype = AA  length = 8
FEATURE                Location/Qualifiers
source                 1..8
                       mol_type = protein
                       organism = Homo sapiens
SEQUENCE: 33
GFTFSSYN                                                          8

SEQ ID NO: 34          moltype = DNA  length = 24
FEATURE                Location/Qualifiers
source                 1..24
                       mol_type = genomic DNA
                       organism = Homo sapiens
SEQUENCE: 34
ggattcacct tcagtagcta taac                                        24

SEQ ID NO: 35          moltype = AA  length = 9
FEATURE                Location/Qualifiers
source                 1..9
                       mol_type = protein
                       organism = Homo sapiens
SEQUENCE: 35
FLSYDGSNK                                                         9

SEQ ID NO: 36          moltype = DNA  length = 27
FEATURE                Location/Qualifiers
source                 1..27
                       mol_type = genomic DNA
                       organism = Homo sapiens
SEQUENCE: 36
tttttatcat atgatggaag taataaa                                     27

SEQ ID NO: 37          moltype = AA  length = 13
FEATURE                Location/Qualifiers
source                 1..13
                       mol_type = protein
                       organism = Homo sapiens
SEQUENCE: 37
AKSEILVVPT LDY                                                    13

SEQ ID NO: 38          moltype = DNA  length = 39
FEATURE                Location/Qualifiers
source                 1..39
                       mol_type = genomic DNA
                       organism = Homo sapiens
SEQUENCE: 38
gcgaaatcgg aaattttagt agtaccaact cttgactac                        39
```

UNITED STATES PATENT AND TRADEMARK OFFICE
CERTIFICATE OF CORRECTION

| | | |
|---|---|---|
| PATENT NO. | : 12,304,969 B2 | Page 1 of 1 |
| APPLICATION NO. | : 18/048644 | |
| DATED | : May 20, 2025 | |
| INVENTOR(S) | : Dan Chalothorn, Lori C. Morton and KehDih Lai | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 69 days.

Signed and Sealed this
Sixteenth Day of December, 2025

John A. Squires
*Director of the United States Patent and Trademark Office*